United States Patent
Al-Murrani et al.

(10) Patent No.: US 9,566,333 B2
(45) Date of Patent: Feb. 14, 2017

(54) COMPOSITIONS AND METHODS FOR DIAGNOSING AND TREATING HYPERTHYROIDISM IN COMPANION ANIMALS

(71) Applicant: HILL'S PET NUTRITION, INC., Topeka, KS (US)

(72) Inventors: Samer Al-Murrani, Topeka, KS (US); Jeffrey Brockman, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 14/366,667

(22) PCT Filed: Dec. 6, 2012

(86) PCT No.: PCT/US2012/068060
§ 371 (c)(1),
(2) Date: Jun. 18, 2014

(87) PCT Pub. No.: WO2013/095935
PCT Pub. Date: Jun. 27, 2013

(65) Prior Publication Data
US 2015/0023968 A1   Jan. 22, 2015

Related U.S. Application Data

(60) Provisional application No. 61/577,373, filed on Dec. 19, 2011.

(51) Int. Cl.
| | |
|---|---|
| *C12N 5/02* | (2006.01) |
| *C12N 15/12* | (2006.01) |
| *C12N 15/63* | (2006.01) |
| *A61K 39/395* | (2006.01) |
| *C07K 14/705* | (2006.01) |
| *C12Q 1/68* | (2006.01) |
| *A61K 47/48* | (2006.01) |
| *A61K 49/00* | (2006.01) |
| *C07K 14/47* | (2006.01) |
| *C07K 16/18* | (2006.01) |
| *C12N 15/113* | (2010.01) |
| *G06F 19/28* | (2011.01) |
| *A61K 39/00* | (2006.01) |

(52) U.S. Cl.
CPC ......... *A61K 39/3955* (2013.01); *A23K 20/153* (2016.05); *A23K 50/40* (2016.05); *A61K 47/48* (2013.01); *A61K 49/00* (2013.01); *C07K 14/473* (2013.01); *C07K 14/705* (2013.01); *C07K 16/18* (2013.01); *C12N 15/113* (2013.01); *C12Q 1/6883* (2013.01); *G06F 19/28* (2013.01); *A61K 2039/505* (2013.01); *C07K 2317/24* (2013.01); *C07K 2317/54* (2013.01); *C07K 2317/55* (2013.01); *C07K 2317/76* (2013.01); *C12N 2310/14* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,437,975 | A | 3/1984 | Gillespie et al. |
| 4,988,617 | A | 1/1991 | Landegren et al. |
| 5,143,854 | A | 9/1992 | Pirrung et al. |
| 5,242,794 | A | 9/1993 | Whiteley et al. |
| 5,409,818 | A | 4/1995 | Davey et al. |
| 5,413,909 | A | 5/1995 | Bassam et al. |
| 5,494,810 | A | 2/1996 | Barany et al. |
| 5,541,061 | A | 7/1996 | Fodor et al. |
| 5,547,839 | A | 8/1996 | Dower et al. |
| 5,554,517 | A | 9/1996 | Davey et al. |
| 5,578,832 | A | 11/1996 | Trulson et al. |
| 5,631,734 | A | 5/1997 | Stern et al. |
| 5,800,992 | A | 9/1998 | Fodor et al. |
| 5,834,758 | A | 11/1998 | Trulson et al. |

(Continued)

FOREIGN PATENT DOCUMENTS

| | | |
|---|---|---|
| WO | WO88/10315 | 12/1988 |
| WO | WO90/06995 | 6/1990 |

(Continued)

OTHER PUBLICATIONS

Altschul et al., 1990, "Basic logal alignment search tool,"J. Mol. Biol. 215(3):403-410.

Altschul et al., 1997, "Gapped BLAST and PSI-BLAST: A new generation of protein database search programs," Nucleic Acids Research 25(17):3389-3402.

Life Link, "Sodium selenate", Life Link, Internet article cited in PCT/US2004/019853 as being retrieved from the Internet on Oct. 13, 2004 (XP002301317); http://www.lifelinknet.com/siteResources/ProductPages/Sodium-Selenate.asp.

(Continued)

*Primary Examiner* — Michael Pak

(57) ABSTRACT

An isolated DNA molecule comprising a fragment of the gene encoding the feline NIS is disclosed as well as methods of use thereof. Also provided are methods for rational diet design of food composition suitable for administration to feline companion animals afflicted with hyperthyroidism, comprising (a) accessing at least one database that comprises a first data set relating functional gene profile of a biofluid or tissue sample from an animal to physiological condition of the animal, where the functional gene profile is that of the feline NIS gene; (b) accessing at least one database that comprises a second data set relating effects of bioactive dietary components on the functional gene profile; (c) using an algorithm drawing on these data sets, processing input data defining physiological condition to derive a nutritional formula promoting wellness of a feline companion animal afflicted with hyperthyroidism; and (d) preparing a food composition based on the nutritional formula.

13 Claims, No Drawings

(56) References Cited

U.S. PATENT DOCUMENTS

| | | |
|---|---|---|
| 5,856,092 A | 1/1999 | Dale et al. |
| 5,858,659 A | 1/1999 | Sapolsky et al. |
| 5,861,245 A | 1/1999 | McClelland et al. |
| 5,871,928 A | 2/1999 | Fodor et al. |
| 5,874,219 A | 2/1999 | Rava et al. |
| 5,902,723 A | 5/1999 | Dower et al. |
| 5,936,324 A | 8/1999 | Montagu |
| 5,981,956 A | 11/1999 | Stern |
| 6,013,449 A | 1/2000 | Hacia et al. |
| 6,020,135 A | 2/2000 | Levine et al. |
| 6,025,601 A | 2/2000 | Trulson et al. |
| 6,033,860 A | 3/2000 | Lockhart et al. |
| 6,040,138 A | 3/2000 | Lockhart et al. |
| 6,045,996 A | 4/2000 | Cronin et al. |
| 6,063,603 A | 5/2000 | Davey et al. |
| 6,090,555 A | 7/2000 | Fiekowsky et al. |
| 6,141,096 A | 10/2000 | Stern et al. |
| 6,156,501 A | 12/2000 | McGall et al. |
| 6,177,248 B1 | 1/2001 | Oliner et al. |
| 6,185,030 B1 | 2/2001 | Overbeck |
| 6,197,506 B1 | 3/2001 | Fodor et al. |
| 6,201,639 B1 | 3/2001 | Overbeck |
| 6,218,803 B1 | 4/2001 | Montagu et al. |
| 6,225,625 B1 | 5/2001 | Pirrung et al. |
| 6,284,460 B1 | 9/2001 | Fodor et al. |
| 6,300,063 B1 | 10/2001 | Lipshutz et al. |
| 6,300,070 B1 | 10/2001 | Boles et al. |
| 6,309,822 B1 | 10/2001 | Fodor et al. |
| 6,333,179 B1 | 12/2001 | Matsuzaki et al. |
| 6,344,316 B1 | 2/2002 | Lockhart et al. |
| 6,361,947 B1 | 3/2002 | Dong et al. |
| 6,368,799 B1 | 4/2002 | Chee |
| 6,386,749 B1 | 5/2002 | Watts et al. |
| 6,391,592 B1 | 5/2002 | Su et al. |
| 6,391,623 B1 | 5/2002 | Besemer et al. |
| 6,410,276 B1 | 6/2002 | Burg et al. |
| 6,582,938 B1 | 6/2003 | Su et al. |
| 6,872,529 B2 | 3/2005 | Su |
| 7,320,863 B2 | 1/2008 | Carrasco et al. |
| 8,759,258 B2 | 6/2014 | Al-Murrani et al. |
| 8,993,001 B2 | 3/2015 | Wedekind et al. |
| 2001/0096235 | 5/2003 | Dong |
| 2003/0082543 A1 | 5/2003 | Su et al. |
| 2004/0131658 A1 | 7/2004 | Kaput |
| 2004/0185475 A1 | 9/2004 | Cao et al. |
| 2005/0058691 A1 | 3/2005 | Wedekind et al. |
| 2005/0064016 A1 | 3/2005 | Wedekind et al. |
| 2006/0056909 A1 | 3/2006 | Chen |
| 2006/0062859 A1 | 3/2006 | Blum et al. |
| 2006/0199155 A1 | 9/2006 | Mosher |
| 2006/0200320 A1 | 9/2006 | Al-Murrani |
| 2007/0118295 A1 | 5/2007 | Al-Murrani |
| 2009/0183943 A1 | 7/2009 | Leistner et al. |
| 2009/0226540 A1 | 9/2009 | Wedekind et al. |
| 2009/0269416 A1 | 10/2009 | Wedekind et al. |
| 2010/0068304 A1 | 3/2010 | Wedekind et al. |
| 2010/0137404 A1 | 6/2010 | Yamka et al. |
| 2010/0151062 A1 | 6/2010 | Stefanon |
| 2010/0153016 A1 | 6/2010 | Stefanon et al. |
| 2010/0323979 A1* | 12/2010 | Weis-Amon ........... A61K 31/00 514/34 |
| 2011/0178005 A1 | 7/2011 | Yamka et al. |
| 2011/0183006 A1 | 7/2011 | Yamka et al. |
| 2011/0189161 A1 | 8/2011 | Blum et al. |
| 2011/0189303 A1 | 8/2011 | Yamka et al. |

FOREIGN PATENT DOCUMENTS

| | | |
|---|---|---|
| WO | WO99/47964 | 9/1999 |
| WO | WO2004112499 | 12/2004 |
| WO | WO 2011/035239 | 3/2011 |
| WO | WO2012174294 | 12/2012 |

OTHER PUBLICATIONS

Association of American Feed Control Officials (AAFCO), "AAFCO Cat Food Nutrient Profiles Based on Dry Matter," Official Publication, pp. 132-133 (2002).

Association of American Feed Control Officials (AAFCO), "AAFCO Cat Tood Nutrient Profiles Based on Dry Matter," Official Publication, pp. 134-135 (2004).

Behrend, 1999, "Medical Therapy of Feline Hyperthyroidism," Compendium on Continuing Education for the Practicing Veterinarian 21(3):234-244.

Belikov, 1993, Pharmaceutical Chemistry, Moscow: Vysshaya Shkola, pp. 43-47.

Brewer, 1982, "Nutrition of the Cat", J. Am. Vet. Med. Assoc. 180(10):1179-1182.

Brown et al., 1992, "Thyroid Growth Immunoglobulins in Feline Hyperthyroidism", Thyroid, 2(2):125-130.

Buffington, 1994, "Nutritional Requirements and Feeding Recommendations," The Cat: Diseases and Clinical Management, 2nd Ed., pp. 133-151.

Chervyakov, 1977, Drugs in Veterinary, Moscow: Kolos, p. 217.

Court et al., 2002, "Identification and concentration of soy isoflavones in commercial cat foods," Am. J. Vet. Res. 63(2):181-185.

Divi et al., 1997, "Anti-Thyroid isoflavones from Soybean—Isolation, Characterization, and Mechanisms of Action,"Biochemical Pharmacology 54(10):1087-1096.

Doerge et al., 2002, "Goitrogenic and Estrogenic Activity of Soy Isoflavones," Environmental Health Perspectives 110(3):349-353.

Dong et al., 2001, "Flexible use of high-density oligonucleotide arrays for single-nucleotide polymorphism discovery and validation," Genome Research 11:1418-1424.

Edinboro et al., 2004, "Epidemiologic study of relationships between consumption of commercial canned food and risk of hyperthyroidism in cats," J. Amer. Vet. Med. Assoc. 224(6):879-886.

Fan et al., 2005, "A class of models for analyzing GeneChip gene expression analysis array data," BMC Genomics 16:6-16.

Ferguson, 1994, "Update on Diagnosis of Canine Hypothyroidism," Vet. Clin. North Amer. Small Anim. Pract. 24(3):515-539.

Foster et al., 2001, "Selenium status of cats in four regions of the world and comparison with reported incidence of hyperthyroidism in cats in those regions," Amer. J. Veterinary Research 62(6):934-937.

Fox et al., 1999, "Electrocardiographic and Radiographic Changes in Cats with Hyperthyroidism: Comparison of Population Evaluated During 1992-1993 vs. 1979-1982," J. Anim. Hosp. Assoc. 35(1):27-31.

Fradkin et al., 1983, "Iodine-induced Thyrotoxicosis," Medicine 62(1):1-20.

Gaitan et al., 1989, "Antithyroid and goitrogenic effects of millet: role of C-glycosylflavones," J. Clin. Endocrinol. Metab. 68(4):707-714.

Gerber et al., 1994, "Etiopathology of Feline Toxic Nodular Goiter," Vet. Clin. N. Am. Small Anim. Pract. Thyroid Disorders 24(3):541-565.

Giuliani et al., 2008, "The flavonoid quercetin regulates growth and gene expression in rat FRTL 5 thyroid cells," Endocrinology 149(1):84-92.

Hand, ed., 2000, Small Animal Clinical Nutrition, 4th ed., pp. 863-868.

Hoffmann et al., 2003, "Transdermal Methimazole Treatment in Cats with Hyperthyroidism" J. Feline Med. Surg. 5(2):77-82.

Holzworth et al., 1980, "Hyperthyroidism in the Cat: Ten Cases", J. Amer. Vet. Med. Assoc. 176(4):345-353.

Johnson et al., 1992, "Iodine content of commercially-prepared cat foods," NZ Vet. J. 40:18-20.

Karlin et al., 1990, "Methods for assessing the statistical significance of molecular sequence features by using general scoring schemes," Proc. Natl. Acad. Sci. USA 87:2264-2268.

Kass et al., 1999, "Evaluation of Environmental, Nutritional and Host Factors in Cats with Hvperthyroidism," J. Vet. Intern. Med. 13:323:329.

(56) References Cited

OTHER PUBLICATIONS

Kato et al., 2005, "A perspective on DNA microarray technology in food and nutritional science," Curr. Opin. Clin. Mat. Metab. Care 8(5):516-522.
Kogai et al., 1997, "Regulation by thyroid-stimulating hormone of sodium/iodide symporter gene expression and protein levels in FRTL-5 cells," Endocrinology 138(6):2227-2232.
Kyle et al., 1994, "Serum free thyroxine levels in cats maintained on diets relatively high or low in iodine," NZ Vet. J. 42:101-103.
Labuc et al., 1986, "Feline hyperthyroidism—A short review," Australian Veterinary Practitioner 16(3):139-142.
Landegren et al., 1988, "A ligase-mediated gene detection technique," Science 241:1077-1081.
Laurberg et al., 2001, "Environmental Iodine Intake Affects the Type of Nonmalignant Thyroid Disease," Thyroid 11:457-469.
Laurberg et al., 1991, "High incidence of multinodular toxic goiter in the elderly population in low iodine intake area vs. high incidence of Graves' disease in the young in a high iodine intake area: comparative surveys of thyrotoxicosis epidemiology in East-Jutland Denmark and Iceland," J. Internal Med. 229:415-420.
Levander, 1986, "Selenium," in Trace Elements in Human and Animal Nutrition, Mertz, W. ed. Orlando, FL: Academic Press Inc., pp. 209-279.
Loginova, 2003, Introduction to Pharmaceutical Chemistry, Misk: BGU, p. 216.
Luo et al., 1991, "The Novel Effects of Selenium on Animals," China Feedstuff, pp. 20-23 (with English translation).
Martin et al., 2000, "Evaluation of dietary and environmental risk factors for hyperthyroidism in cats," J. Am. Vet. Med. Assoc. 217(6):853-856.
Martins et al., 1989, "Natural course of iodine-induced thyrotoxicosis (Jodbasedow) in endemic goiter area: A 5 year follow-up," J. Endocrin. Invest. 12:239-244.
Mason et al., 1995, "Determination of Iodine in Urine, Using Epithermal Instrumental Neutron Activation Analysis (EINAA), at the University of Missouri Research Reactor (MURR)," J. Radioanalytical Nucl. Chem. 195(1):57-65.
McDowell, 1992, "Iodine," In: Minerals in Animal and Human Nutrition, San Diego: Academic Press, pp. 224-245.
Mian et al., 2001, "Sodium iodide symporter and pendrin expression in human thyroid tissues," Thyroid 11(9):825-830.
Mumma et al., 1986, "Toxic and protective constituents in pet foods," Am. J. Vet. Res. 47(7):1633-1637.
National Research Council Board on Agriculture, 1978, "No. 13: Nutrient requirements of cats, Revised 1978," National Academy of Sciences, Washington, D.C. pp. 10, 18-21, 25-27.
Nichols et al., 1998, "Longitudinal study of iodine in market milk and infant formula via epiboron neutron activation analysis," J. Radioanalytical Nucl. Chem. 236(1-2):65-69.
Pennington, 1990, "A review of iodine toxicity reports," J. Am. Dietetic Assoc. 90(11):1571-1581.
Peterson et al., 1993, "Comparison of the Disposition of Carbimazole and Methimazole in Clinically Normal Cats," Res. Vet. Sci. 54(3):351-355.
Peterson et al., 1983. "Feline Hyperthyroidism: Pretreatment Clinical and Laboratory Evaluation of 131 Cases," J. Amer. Vet. Med. Assoc. 1983(1):103-110.
Peterson et al., 1981, "Propylthiouracil in the Treatment of Feline Hyperthyroidism," J. Am. Vet. Med. Assoc. 179:485-487.
Peterson et al., 1980, "Spontaneous Feline Hyperthyroidism in," (Abstract) Program of the 62nd Annual Meeting of the Endocrine Society, No. 516, 203.
Peterson et al., 1979, "Spontaneous Hyperthyroidism in the Cat," (Abstract) Proceedings of the American College of Veterinary Internal Medicine, p. 108.
Peterson et al., 1994, "The cat: diseases and clinical management", R.G. Sherding, ed., New York, Churchill Livingstone, 2nd Ed., pp. 1416-1452.
Peterson et al., 1988, "Methimazole Treatment of 262 Cats with Hyperthyroidism," J. Vet. Int. Med. 2(3):150-157.

Ranz et al., 2002, "Estimation of iodine status in cats," J. Nutrition 132(6):1751S-1753S.
Robbins et al., 1984, *Pathologic Basis of Disease*, 3rd ed., pp. 1203-1204.
Royal Canin Veterinary Diet, 2004, http://www/walthamusa.com/Learning%20Center/pdf/LP21.pdf.
Scarlett et al., 1988, "Feline Hyperthyroidism: A Descriptive and Case-Control Study," Preventive Vet. Med. 6:295-309.
Schrauzer, 2000, "Selenomethionine: A Review of Its Nutritional Significance, metabolism and Toxicity," J. Nutrition 130(7):1653-1656.
Selmi-Ruby, 2000, "Sus scrofa mRNA for Sodium Iodide Symporter, short form," GenBank [online], Accession No. AJ276292, Dec. 3, 2000.
Selmi-Ruby et al., 2003, "The porcine sodium/iodide symporter gene exhibits an uncommon expression pattern related to the use of alternative splice sites not present in the human or murine species," Endocrinology 144(3):1074-1085
Simcock et al., 2010 "The role of selenium in companion animal health and nutrition," Institute of Food, Nutrition and Human Health, Massey University, Palmerton North, New Zealand, pp. 511-520.
Slater et al., 2001, "Long-Term Health and Predictors of Survival for Hyperthyroid Cats Treated with Iodine 131," J. Vet. Intern. Med. 15(1):47-51.
Smith, 1993, "Changes and challenges in feline nutrition," J. Am. Vet. Med. Assoc. 203(10):1395-1400.
Son et al., 2001, "Lack of Effect of Soy Isoflavone on Thyroid Hyperplasia in Rats Receiving an Iodine-deficient Diet," Jpn. J. Cancer Res. 92:103-108.
Spate et al., 1995, "Determination of iodine in Human Nails Via Epithermal Neutron Activation Analysis," J. Radioanalytical and Nuclear Chemistry, Articles 195(1):21-30.
Spielbauer et al., 2005, "Impact of microarray technology in nutrition and food research," Mol. Nutr. Food Research 49(10):908-917.
Takeshita et al., 1997, "TRAM-1, A novel 160-kDa thyroid hormone eceptor activator molecule, exhibits distinct properties from steroid receptor coactivator-1," J. Biological Chemistry 272(44):27629-27634.
Tarttelin et al., 1994, "Dietary Iodine Level and Thyroid Function in the Cat," American Institute of Nutrition. J. Nutrition 124(12):2577S-2578S.
Tarttelin et al., 1992, "Serum free thyroxine levels respond inversely to changes in level of dietary iodine in the domestic cat," New Zealand Veterinary J. 40:66-68.
Thyrotoxicosis and Hypothyroidism: Evaluation and Management Guidelines of the Amer. Assoc. of Clinical Endocrinologists, SMM Endokrinologiya, 2002, p. 26, http://www.airmed.com/au/standart/10.pdf.
Trepanier et al., 2003, "Efficacy and safety of once versus twice daily administration of methimazole in cats with hyperthyroidism," J. Am. Vet. Med. Assoc. 222(7):954-958.
Trepanier et al., 2006, "Medical management of hyperthyroidism," Clinical Techniques in Small Animal Practice 21(1):22-28.
Wedekind et al., "Bioavailability of Selenium in Petfood Ingredients," (Abstract), Annual Meeting of Professional Research Scientists on Experimental Biology, New Orleans, Louisiana, USA (Apr. 6-9, 1997).
Wedekind et al., 2000, "Current AAFCO and NRC Recommendations for Selenium (Se) Are Too Low for Kittens," (Abstract) FASEB J. 14(4):A295.
Wedekind et al., "Defining the Safe Lower and Upper Limit for Selenium (Se) in Adult Dogs," (Abstract), Annual Meeting of Professional Research Scientists on Experimental Biology, New Orleans, Louisiana, USA (Apr. 20-24, 2002).
Wedekind et al., 2003, "Determination of the selenium requirement in kittens," J. Anim. Physiol. Anim. Nutr. 87:315-323.
Wedekind et al., 2001, "Effect of Varying Selenium (Se) Intake on Thyroid Hormone Metabolism in Dogs," (Abstract) FASEB J. 15(5):A953.

(56) References Cited

OTHER PUBLICATIONS

Wedekind et al., 2000, "Selenium in Pet Foods—Is Bioavailability an Issue?" Proceedings, Purina Nutrition Forum: Supplement to Compendium on Continuing Education for the Practicing Veterinarian 22(9A):17-22.
Wedekind et al., 2004, "The selenium requirement of the puppy," J. Anim. Physiol. Anim. Nutr. 88(9-10):340-347.
Yang et al., 1983, "Endemic selenium intoxication of humans in China", Am. J. Clin. Nutr. 37(5):872-881.
Yang et al., 1989, "Studies of Safe Maximal Daily Dietary Se-intake in a Seleniferous Area in China. Part II: Relation Between Se-Intake and the Manifestation of Clinical Signs and Certain Biochemical Alterations in Blood and Urine," J. Trace Elem. Electrolytes Health Dis. 3(3):123-130.
Yen et al., 1996, "Vitamin D receptors repress basal transcription and exert dominant negative activity on triiodothyronine-mediated transcriptional activity," J. Biological Chemistry 271(18):10910-10916.
Yu et al., 2002, "A Low-Selenium Diet Increases Thyroxine and Decreases 3,5,3'Triiodothyronine in the Plasma of Kittens," J. Anim. Physiol. a. Anim. Nutr. 86(1-2):36-41.
"007_021_H15 black bear brain library Ursus americanus cDNA 5', mRNA sequence.", XP002691234, retrieved from EBI accession No. EM_EST:GW310727, Database accession No. GW310727 sequence, Jan. 1, 2010.
"ENSEMBL ENSFCAP00000006965", Jul. 2, 2008, XP002691235, retrieved from EBI accession No. UNIPARC: UPI00017A1B71, Database accession No. UPI00017A1B71 sequence & "Feline solute carrier family 5 (sodium iodide symporter), member 5", Internet Citation, Apr. 1, 2011, p. 1, XP002683979, Retrieved from the internet: URL:http://apr2011.archive.ensembl.org/felis_catus/transcript/proteinsummary?db=core [retrieved on Sep. 24, 2012] the whole document.
Barringer et al. Gene 89:117 (1990).
Berger and Kimmel Methods in Enzymology, vol. 152, Guide to Molecular Cloning Techniques (Academic Press, Inc., San Diego, Calif., 1987).
Database Genbank [Online] NCBI; Nov. 6, 2012, "Predicted: Felis catus solute carrier family 5 (sodium iodide symporter), member 5 (SLC5A5), mRNA.", XP002691236, Database accession No. XM_003982101 the whole document.
Gao, X, et al: "Gene Expression Analysis of Feline thyroid tissue and blood from cats with evidence of mild or marked hyperthyroidism reveals potential molecular causes of the disease and identifies future routes for intervention", Research abstract program of the 2011 Acvim Forum Denver, Colorado, Jun. 15 18, 2011, vol. 25, No. 3, May 3, 2011, p. 678, XP002683978, DOI: 10.1111/J.1939-1676.2011.0726.S, Retrieved from the Internet: URL:http://onlinelibrary. Wiley.com/doi/10.111/j.1939-1676.2011.0726.x/pdf [retrieved on Sep. 24, 2012] abstract.
Guatelli et al., Proc. Nat. Acad. Sci. USA, 87, 1874 (1990).
Hein A.K. et al., BGX: a fully Bayesian integrated approach to the analysis of Affymetrix GeneChip data, Biostatistics, 2005, vol. 6: 349-373.
International Search Report and the Written Opinion issued in International Application PCT/US2012/68060 mailed Feb. 14, 2013. WO.
Irizarry et al., Summaries of Affymetrix GeneChip probe level data, Nucleic Acid Res., 2003, vol. 31(4): e15.
Irizarry R.A. et al., Exploration, normalization and summaries of high density oligonucleotide array probe level data, Biostatistics, 2003, vol. 4:249-264.
Kwoh et al., Proc. Natl. Acad. Sci. USA 86, 1173 (1989).
Li, C. Mo, 2001, Model-based analysis of oligonucleotide arrays: expression index computation and outlier detection, Proc. Acad. Sci. USA, vol. 98:31-36.
Maniatis et al. Molecular Cloning: A Laboratory Manual (2nd Ed. Cold Spring Harbor, N.Y, 1989).
Nielsen Curr. Opin. Biotechnol., 10:71-75 (1999).
Nielsen et al., Science 254:1497-1500 (1991).
Peterson, et al.: "Diagnostic tests for Hyperthyroidism in Cats", Clinical techniques in small animal practice, Sauders, Philadelphia, PA, US, vol. 21, No. 1, Feb. 1, 2006, pp. 2-9, XP028031584, ISSN: 1096-2867, DOI: 10.1053/J.CTSAP.2005.12.001, [retrieved on Feb. 1, 2006] the whole document.
Rafael. A. Irizarry, Benjamin M. Bolstad, Francois Collin, Leslie M. Cope, Bridget Hobbs and Terence P. Speed (2003), Summaries of Affymetrix GeneChip probe level data Nucleic Acids Research 31(4):e15.
Written Opinion of the International Preliminary Examining Authority issued in International Application PCT/US2012/68060 mailed Nov. 18, 2013. WO.
Wu and Wallace, Genomics 4, 560 (1989), Landegren et al., Science 241, 1077 (1988).
Young and Davis, P.N.A.S, 80: 1194 (1983).
Zhou, L. et al., An expression index for Affymetrix GeneChips based on the generalized logarithm, Bioinformatics, 2005, vol. 21(21): 3983-3989.
Wakeling et al., "Evaluaton of Predictors for the Diagnosis of Hyperthyroidism in Cats", pp. 1057-1065.
Pocar et al., "AhR-Agonist-induced Transcriptional Changes of Genes Involved in Thyroid Function in Primary Porcine Thyrocytes", Downioaded from http://loxaci.oxfordjournals.org/ at Japan Patent Office on Mar. 8, 2016, pp. 408-414.
Fickett, "Recognition of protein coding regions in DNA sequences", Nucleic Acids Research, 10/17, pp. 5303-5318, 1982.
Hutchinson et al., "The prediction of exons through an analysis of spliceable open reading frames ", Nucleic Acid Research, 20/13, pp. 3453-3462, 1992.

\* cited by examiner

COMPOSITIONS AND METHODS FOR DIAGNOSING AND TREATING HYPERTHYROIDISM IN COMPANION ANIMALS

CROSS-REFERENCE TO RELATED PATENT APPLICATIONS

The present application is a U.S. national stage entry under 35 U.S.C. §371 of Patent Cooperation Treaty Patent Application No. PCT/US2012/68060, filed Dec. 6, 2012, which claims priority from U.S. Provisional Patent Application No. 61/577,373, filed Dec. 19, 2011, the entirety of which is incorporated herein by reference.

FIELD

The present invention relates to an isolated DNA molecule encoding a portion of the feline NIS protein, as well as the use of that gene fragment in methods for design of animal food compositions suitable for administration to feline companion animals afflicted with hyperthyroidism, as well as compositions and methods for treating hyperthyroidism in feline companion animals.

SEQUENCE LISTING

The instant application contains a Sequence Listing which has been submitted via EFS-Web and is hereby incorporated by reference in its entirety. Said ASCII copy, created on Dec. 15, 2011, is named 9344P-00-HL_Sequence_Listing_ST25.txt and is 3 KB in size.

BACKGROUND

Hyperthyroidism is a relatively common endocrine disorder that is particularly prevalent in older cats. It is a serious health condition that results from the hyperplastic growth of thyroid tissue and the over-production of thyroid hormone. Typical hyperthyroidism treatments include chronic administration of an antithyroid medication, surgical removal of the thyroid, and/or radioactive iodine therapy. These treatments are expensive and have their limitations and side effects. For example, as most antithyroid medications are administered orally, compliance is often compromised. Surgery requires anesthesia and is not necessarily an option for older felines, particularly felines that suffer from other diseases as well. Radioactive iodine therapy is available only in facilities licensed to use radioactive materials, and requires hospitalization of the felines until their levels of radioactivity are safe.

Since the production of thyroid hormone requires dietary iodine, methods have been developed to treat hyperthyroidism in cats that involve feeding diets with restricted iodine content. It would be desirable to supplement such iodine-restricted diets with ingredients that reduce iodine uptake by the thyroid gland and with ingredients that inhibit synthesis of thyroid hormone.

SUMMARY

The present disclosure provides methods and reagents for identification of dietary ingredients that reduce iodine uptake by the thyroid gland and that inhibit synthesis of thyroid hormone. The methods disclosed herein involve the use of an isolated gene fragment, which encodes a portion of the feline sodium/iodine symporter protein (NIS protein), to develop gene expression profile data in the presence and absence of test materials. Using those methods it has been possible to identify materials that can be included in the diet of a feline afflicted with hyperthyroidism in order to treat that condition.

The present disclosure provides an isolated gene fragment encoding a portion of the feline sodium/iodine symporter protein (NIS protein) that has the nucleotide sequence of SEQ ID NO:1, and that encodes a peptide having the amino acid sequence of SEQ ID NO: 2.

Also provided herein are recombinant vectors and transformed cells comprising the isolated feline NIS gene fragment. The present disclosure also provides methods involving the use of such isolated DNA molecules to establish gene expression profiles for the feline NIS gene in healthy and afflicted animals and measurement of NIS gene expression profiles in the presence and absence of food ingredients and extracts thereof for those genes for the design of animal food compositions suitable for administration to feline companion animals afflicted with hyperthyroidism. The present disclosure also provides compositions and methods of treatment of hyperthyroidism in felines.

The present disclosure also provides a method for design of a pet food suitable for administration to a feline companion animal afflicted with hyperthyroidism, the method comprising: (a) accessing at least one first database that comprises a first data set relating a functional gene profile of a biofluid or tissue sample from an animal to physiological condition and optionally genotype of the animal, wherein the functional gene profile is that of the feline NIS gene, (b) accessing at least one second database that comprises a second data set relating effects of bioactive dietary components on the functional gene profile of step (a); (c) using a first algorithm drawing on the first and second data sets, processing input data defining physiological condition and optionally genotype of the subpopulation, e.g., felines afflicted with hyperthyroidism, to derive a nutritional formula useful for selecting and preparing a food composition for that animal subpopulation; and (d) preparing a food composition based on the nutritional formula; wherein that food composition is suitable for administration to a feline companion animal afflicted with hyperthyroidism.

In certain aspects of this embodiment, the first data set is derived from samples collected from a multiplicity of individual animals representative of a range of genotypes and physiological conditions that includes feline companion animals afflicted with hyperthyroidism. In one aspect, each such sample from an individual animal is associated with a provenance record that comprises zoographical data relevant to defining the genotype and physiological condition, at the time the sample is collected, of the individual animal. In another aspect of this embodiment, the zoographical data comprise one or more data items relating to genotype, selected from the group consisting of breed, breed(s) of parents, pedigree, sex, coat type, and evident hereditary conditions and disorders, particularly hyperthyroidism. In another aspect of this embodiment, the zoographical data comprise one or more data items relating to physiological condition, selected from the group consisting of age, weight, veterinary medical history, reproductive history, present wellness or disease state, appetite, physical activity level, mental acuity, behavioral abnormalities and disposition, and, in particular, the presence and degree of affliction with hyperthyroidism.

In a specific aspect of this method, the first data set comprises data relating to analysis of the sample with respect to one or more components selected from the group consisting of DNA, RNA, proteins, metabolites as biomarkers, while the second data set is derived from controlled experiments comprising exposing an animal model to different levels of one or more bioactive dietary components.

The present invention also relates to compositions and methods for diagnosing hyperthyroidism in felines as well as methods for identifying materials and formulating food compositions containing those materials that will be useful for treatment of hyperthyroidism in felines.

In another specific aspect of this method, the input data comprise zoographical data relevant to defining the genotype and physiological condition of feline companion animals afflicted with hyperthyroidism. In still another aspect of this method, the input data comprise analytical data from a biofluid or tissue sample obtained from feline companion animals not afflicted with hyperthyroidism. In other specific aspects of this method, the input data comprise analytical data from a biofluid or tissue sample obtained from feline companion animals afflicted with mild hyperthyroidism as well as from feline companion animals afflicted with severe hyperthyroidism.

The present disclosure is also directed to animal food compositions prepared by the above method for design of a pet food, illustrative examples of which are described herein below, which are useful for administration to feline companion animals afflicted with hyperthyroidism.

Accordingly, provided herein are methods for rational design of a diet for an animal afflicted with a disease or condition, comprising identification of bioactive dietary components useful in ameliorating the effects of a disease or condition with which the animal is afflicted. In a particular, illustrative aspect of this embodiment, the disease or condition is hyperthyroidism and the afflicted animal is a feline companion animal.

In one embodiment, the present disclosure provides a method of treatment of hyperthyroidism in a companion animal. In one aspect, this disclosure provides a method for treatment of hyperthyroidism in a feline companion animal.

In another embodiment, the present disclosure provides compositions useful in a method of treatment of hyperthyroidism in a companion animal. In one aspect, this disclosure provides compositions useful in a method for treatment of hyperthyroidism in a feline companion animal.

In particular aspects of these embodiments, the hyperthyroid companion animal that is in need of treatment is fed a pet food composition that comprises an effective amount of a bioactive dietary component, that is sufficient to suppress expression or activity of at least one polypeptide required for biosynthesis, transport, or activity of either or both of thyroxine and triiodothyronine, such as, but not limited to the activity of the feline NIS gene described herein.

In certain embodiments, the polypeptide inhibited by the bioactive dietary components is selected from the group consisting of thyroid peroxidase, sodium/iodide symporter (NIS), thyroid oxidase, intrathyroidal type I 5'-deiodinase, thyroid stimulating hormone receptor, pendrin, monocarboxylate transporter 8, and combinations thereof.

Also provided is a method for design of a diet suitable for treating a disease or condition in an animal.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

Additional and further embodiments and objects of the present disclosure will be readily apparent to those of ordinary skill in the art.

In another embodiment, the disclosure provides a method of treating hyperthyroidism in a feline in need thereof, comprising diagnosing the existence of hyperthyroidism, using, e.g., the methods disclosed above, and managing the condition, for example by diet alone or in combination with appropriate medication. In one aspect of this embodiment, the diet includes one or more components identified by the methods disclosed herein, which components are useful for reducing iodine uptake by the thyroid gland or for inhibiting synthesis of thyroid hormone, including, inter alia, components capable of depressing or inhibiting NIS gene expression or reducing or inhibiting NIS protein function.

In a further embodiment, the invention provides reagents, optionally labeled, useful in the detection of the level of expression of the NIS biomarker in a feline. Such reagents may include, e.g., antibodies, for example monoclonal antibodies, single chain antibodies, and functional antibody fragments, that selectively recognize the feline NIS protein, e.g., antibodies, for example monoclonal antibodies, single chain antibodies, and functional antibody fragments, that selectively recognize the peptide of SEQ ID NO:2. Other such reagents include aptamers, for example, nucleic acid or peptidic aptamers, that recognize, or that selectively recognize the feline NIS protein or the peptide of SEQ ID NO:2, as well as oligonucleotide probes capable of selectively hybridizing to the feline NIS gene or to the nucleotide sequence of SEQ ID NO:1.

In a further embodiment, the present disclosure provides a kit for the diagnosis, prognosis or monitoring of hyperthyroidism in a feline, comprising means for measuring expression of the feline NIS gene, in a biological sample from the feline, and instructions for using such means to measure expression the NIS gene in a biological sample from the feline and evaluating the presence of a process leading to a hyperthyroidism in a feline. The kit means measuring the one or more biomarkers in one or more nucleic acid probes capable of detecting gene expression of the NIS gene, which probes are capable of selectively hybridizing to the nucleic acid of SEQ ID NO:1 under stringent conditions.

In other aspects of these embodiments, the means for measuring the one or more biomarkers is one or more antibodies capable of detecting gene expression of the NIS gene by selectively recognizing the expressed NIS protein, or by selectively recognizing the peptide of SEQ ID NO:2. Such kits may be in an ELISA format comprising antibody capable of detecting the NIS protein, including an isolated, purified or recombinant NIS protein corresponding to the expressed protein or the peptide sequence of SEQ ID NO:2, and buffer.

In still other aspects of this embodiment, the means for measuring the NIS biomarker is one or more aptamers, e.g., as hereinbefore described, capable of detecting gene expression of the NIS protein or by recognizing the expressed NIS protein.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiments is merely exemplary in nature and is in no way intended to limit the invention, its application, or uses.

Definitions

As used herein and in the appended claims, the singular forms "a," "an," and "the" include plural references unless the context clearly dictates otherwise, e.g., reference to "a variant" includes a plurality of variants. Further, defined terms include variations of the terms used in the proper grammatical context, e.g., the term "specifically binds" includes "specific binding" and other forms of the term. Similarly, the words "comprise," "comprises," and "comprising" are to be interpreted inclusively rather than exclusively.

The term "antibody" means any immunoglobulin that binds to a specific antigen, including IgG, IgM, IgA, IgD, and IgE antibodies. The term includes polyclonal, monoclonal, monovalent, humanized, heteroconjugate, antibody compositions with polyepitopic specificity, chimeric, bispecific antibodies, diabodies, single-chain antibodies, and antibody fragments such as Fab, Fab', F(ab')$_2$, and Fv, or other antigen-binding fragments. Antibody specificity can be established using methods and assays known in the art, including but not limited to, competition assays and the use of phage-display systems. Accordingly, an antibody that specifically binds, e.g., the feline NIS protein, is an antibody with association/disassociation rates and/or binding affinity that are substantially greater for the peptide of SEQ ID NO:2 or a portion, subfragment, or peptide portion thereof, than for the homologous protein of another species, e.g., for the human NIS protein. In this context, the term "substantially" indicates that the subject association/disassociation rates and/or binding affinity differ by a factor of at least 1.1, 1.2, 1.5, 2, 5, 10, 50, 100, 1000, or 10,000 or more.

The term "array" means an ordered arrangement of at least two probes on a substrate. At least one of the probes is a control or standard and at least one of the probes is a diagnostic probe. The arrangement of from about two to about 40,000 probes on a substrate assures that the size and signal intensity of each labeled complex formed between a probe and a sample polynucleotide or polypeptide is individually distinguishable. The collection of molecules deposited on the array may be prepared either synthetically or biosynthetically. The array may take a variety of forms including libraries of soluble molecules, libraries of compounds tethered to resin beads, silica chips or other solid supports. The nucleic acid array may include libraries of nucleic acids which can be prepared by spotting nucleic acids in essentially any length (for example, from 1 to about 1,000 nucleotides in length) onto a substrate. A nucleic acid probe array preferably comprises nucleic acids bound to a substrate in known locations. In other embodiments, the system may include a solid support or substrate, such as a membrane, filter, microscope slide, microwell, sample tube, bead, bead array, or the like. The solid support may be made of various materials, including paper, cellulose, nylon, polystyrene, polycarbonate, plastics, glass, ceramic, stainless steel, or the like. The solid support may preferably have a rigid or semi-rigid surface, and may preferably be spherical (e.g., bead) or substantially planar (e.g., flat surface) with appropriate wells, raised regions, etched trenches, or the like. The solid support may also include a gel or matrix in which nucleic acids may be embedded.

The term "biomarkers" refers to genes and gene products encoded by a gene of the invention or a homolog thereof, especially a feline homolog thereof, wherein the gene has been determined to have been differentially expressed as a result of a disease, condition, disorder or the administration of a substance, drug, nutrient or dietary component or combinations thereof, and wherein such genes and gene products of the invention are identified, e.g., in SEQ ID NO: 1. A biomarker may be a polynucleotide, polypeptide, protein, RNA, including an RNA transcript or its translation product, DNA, cDNA, a metabolite of one or more of the foregoing molecules, or a useful variant of any one of the foregoing molecules, the differential expression of which is associated with feline hyperthyroidism, wherein the correlation of such differential expression in a sample taken from a test animal to a sample taken from a control animal can be used in the diagnosis, prognosis, monitoring or treatment of condition, disease or disorder in an animal in need thereof. In addition, a biomarker can be generally used to refer to any portion or segment of such gene or protein that can identify or correlate with the full-length gene or protein, for example, in an assay or other method of the invention. Biomarker expression can also be identified by detection of biomarker translation (i.e., detection of biomarker protein in a sample). Methods suitable for the detection of biomarker proteins include any suitable method for detecting and/or measuring proteins from a cell or cell extract. Such methods include, but are not limited to, immunoblot (e.g., Western blot), enzyme-linked immunosorbent assay (ELISA), radioimmunoassay (RIA), immunoprecipitation, immunohistochemistry and immunofluorescence. Particularly preferred methods for detection of proteins include any cell based assay, including immunohistochemistry and immunofluorescence assays. Such methods are well known in the art.

The term "comparably" as used to compare expression of a test sample to a control sample shall mean indicia of like character and quantity and shall include, without limitation, values within one standard deviation around the mean value to which said comparison is made and values encompassing differential expression between the test sample and control sample.

The terms "differentially expressed gene," "differential gene expression," "differential expression" or "differentially expressed" and their synonyms, which are used interchangeably, refer to a gene whose expression is activated to a higher or lower level in a subject suffering from a disease, condition, or disorder, or as a result of the being administered a substance, drug, nutrient or dietary component or combinations thereof, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, condition, or disorder, or as a result of being administered a substance, drug, nutrient or dietary component or combinations thereof, or between various stages of the same disease, condition, or disorder, or as a result of being administered different amounts of a substance, drug, nutrient or dietary component or combinations thereof. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about 2.0, 1.9, 1.8, 1.7, 1.6, 1.5, 1.4, 1.3, 1.25-fold, change in the amount of transcribed polynucleotides or translated protein in a sample.

The term "fold" when used as a measure of differential gene expression means an amount of gene expression in a feline that is a multiple or a fraction of gene expression compared to the amount of gene expression in a comparison feline, e.g., a feline afflicted with hyperthyroidism compared to an animal not demonstrating such a condition. For example, a gene that is expressed 2 times as much in the animal as in the comparison animal has a 2-fold differential gene expression and a gene that is expressed one-half as much in the animal as in the comparison animal also has a 2-fold differential gene expression.

The term "fragment" means (1) an oligonucleotide or polynucleotide sequence that is or that comprises a portion of a complete sequence and that has the same or similar activity for a particular use as the complete polynucleotide sequence or (2) a peptide or polypeptide sequence that is or that comprises a portion of a complete sequence and that has the same or similar activity for a particular use as the complete polypeptide sequence. Such fragments can comprise any number of nucleotides or amino acids deemed suitable for a particular use. Generally, oligonucleotide or polynucleotide fragments contain at least about 10, 15, 20, 25, 30, 35, 40, 45, 50, 60, 70, 80, 90, 100, 200, 400, 600, 800, or 1000 or more nucleotides and polypeptide fragments contain at least about 4, 6, 8, 10, 12, 14, 16, 18, 20, 22, 24, 26, 28, 30, 32, 34, 36, 38, 40, 42, 44, 46, 48, or 50 or more consecutive amino acids from the complete sequence. The term encompasses polynucleotides and polypeptides variants of the fragments. A polynucleotide, for example, can be broken up, or fragmented into, a plurality of segments.

Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "*Molecular Cloning: A Laboratory Manual*," 3rd Ed. Cold Spring Harbor Laboratory Press, Cold Spring Harbor, N.Y. (2001) ("Sambrook et al."), which is incorporated herein by reference for all purposes. These methods can be optimized to digest a nucleic acid into fragments of a selected size range. Useful size ranges may be from 25, 50, 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

The term "gene" or "genes" means a complete or partial segment of DNA involved in producing a polypeptide, including regions preceding and following the coding region (leader and trailer) and intervening sequences (introns) between individual coding segments (exons). The term encompasses any DNA sequence that hybridizes to the complement of gene coding sequences.

The term "homolog" means (1) a polynucleotide, including polynucleotides from the same or different animal species, having greater than 30%, 50%, 70%, 90%, 91%, 92%, 93%, 94%, 95%, 96%, 97%, 98% or 99% sequence similarity to a polynucleotide and having the same or substantially the same properties and performing the same or substantially the same function as the complete polynucleotide, or having the capability of specifically hybridizing to a polynucleotide under stringent conditions or (2) a polypeptide, including polypeptides from the same or different animal species, having greater than 30%, 50%, 70%, 90%, 91%, 92%, 93%, 94%, 95%, 96%, 97%, 98% or 99% sequence similarity to a polypeptide identified by the expression of polynucleotides and having the same or substantially the same properties and performing the same or substantially the same function as the complete polypeptide, or having the capability of specifically binding to a polypeptide identified by the expression of polynucleotides. Sequence similarity of two polypeptide sequences or of two polynucleotide sequences is determined using methods known to skilled artisans, e.g., the algorithm of Karlin and Altschul (*Proc. Natl. Acad. Sci. USA* 87:2264-2268 (1990)). Such an algorithm is incorporated into the NBLAST and XBLAST programs of Altschul et al. (*J. Mol. Biol.* 215:403-410 (1990)). To obtain gapped alignments for comparison purposes, Gapped Blast can be utilized as described in Altschul et al. (*Nucl. Acids Res.* 25: 3389-3402 (1997)). When utilizing BLAST and Gapped BLAST programs, the default parameters of the respective programs (e.g., XBLAST and NBLAST) are used. See http://www.ncbi.nlm.nih.gov.

The term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid." The proportion of the population of polynucleotides that forms stable hybrids is referred to herein as the "degree of hybridization."

Hybridization reactions can be performed in absolute or differential hybridization formats. In the absolute hybridization format, polynucleotides derived from one sample are hybridized to the probes in a nucleic acid array. Signals detected after the formation of hybridization complexes correlate to the polynucleotide levels in the sample. In the differential hybridization format, polynucleotides derived from two samples are labeled with different labeling moieties. A mixture of these differently labeled polynucleotides is added to a nucleic acid array. The nucleic acid array is then examined under conditions in which the emissions from the two different labels are individually detectable. In one embodiment, the fluorophores Cy3 and Cy5 (Amersham Pharmacia Biotech, Piscataway, N.J.) are used as the labeling moieties for the differential hybridization format.

Signals gathered from nucleic acid arrays can be analyzed using commercially available software, such as those provided by Affymetrix or Agilent Technologies. Controls, such as for scan sensitivity, probe labeling and cDNA or cRNA quantization, are preferably included in the hybridization experiments. Hybridization signals can be scaled or normalized before being subject to further analysis. For instance, hybridization signals for each individual probe can be normalized to take into account variations in hybridization intensities when more than one array is used under similar test conditions. Hybridization signals can also be normalized using the intensities derived from internal normalization controls contained on each array. In addition, genes with relatively consistent expression levels across the samples can be used to normalize the expression levels of other genes. In one embodiment, probes for certain maintenance genes are included in a nucleic acid array of the present invention. These genes are chosen because they show stable levels of expression across a diverse set of tissues. Hybridization signals can be normalized and/or scaled based on the expression levels of these maintenance genes.

The term "hybridization complex" means a complex that is formed between sample polynucleotides when the purines of one polynucleotide hydrogen bond with the pyrimidines of the complementary polynucleotide, e.g., 5'-A-G-T-C-3' base pairs with 3'-T-C-A-G-5'. The degree of complementarily and the use of nucleotide analogs affect the efficiency and stringency of hybridization reactions.

The term "hybridization probes" includes nucleic acids (such as oligonucleotides) capable of binding in a base-specific manner to a complementary strand of nucleic acid. Such probes include peptide nucleic acids, as described in Nielsen et al., Science 254:1497-1500 (1991), Nielsen Curr. Opin. Biotechnol., 10:71-75 (1999) and other nucleic acid analogs and nucleic acid mimetics. See U.S. Pat. No. 6,156, 501 filed Apr. 3, 1996.

"Nucleic acid sequence" means an oligonucleotide, nucleotide or polynucleotide, and fragments or portions thereof, and to DNA or RNA of genomic or synthetic origin which may be single- or double-stranded, and represent the sense or antisense strand.

The term "polynucleotide" or "oligonucleotide" means a polymer of nucleotides. The term encompasses DNA and RNA (including cDNA and mRNA) molecules, either single or double stranded and, if single stranded, its complementary sequence in either linear or circular form. The term also encompasses fragments, variants, homologs, and alleles, as appropriate for the sequences that have the same or substantially the same properties and perform the same or substantially the same function as the original sequence. The sequences may be fully complementary (no mismatches) when aligned or may have up to about a 30% sequence mismatch. For polynucleotides, the chain contains from about 20 to 10,000 from 50 to 8,000, from 100 to 5000, or from 150 to 3500 nucleotides. For oligonucleotides, the chain contains from about 2 to 100, from 3 to 80, from 4 to 60, from 5 to 40, or from 6 to 30 nucleotides. The exact size of a polynucleotide or oligonucleotide will depend on various factors and on the particular application and use of the polynucleotide or oligonucleotide. The term includes nucleotide polymers that are synthesized and that are isolated and purified from natural sources. The term "polynucleotide" is inclusive of "oligonucleotide."

The term "polypeptide," "peptide," or "protein" means a polymer of amino acids. The term encompasses naturally occurring and non-naturally occurring (synthetic) polymers and polymers in which artificial chemical mimetics are substituted for one or more amino acids. The term also encompasses fragments, variants, and homologs that have the same or substantially the same properties and perform the same or substantially the same function as the original sequence. The term encompasses polymers of any length, preferably polymers containing from about 2 to 1000, from 4 to 800, from 6 to 600, and from 8 to 400 amino acids. The term includes amino acid polymers that are synthesized and that are isolated and purified from natural sources. In some instances herein the terms "polypeptide," "peptide," or "protein" are used interchangeably.

The term "probe" means (1) an oligonucleotide or polynucleotide, either RNA or DNA, whether occurring naturally as in a purified restriction enzyme digest or produced synthetically, that is capable of annealing with or specifically hybridizing to a polynucleotide with sequences complementary to the probe or (2) a peptide or polypeptide capable of specifically binding a particular protein or protein fragment to the substantial exclusion of other proteins or protein fragments. An oligonucleotide or polynucleotide probe may be either single or double stranded. The exact length of the probe will depend upon many factors, including temperature, source, and use. For example, for diagnostic applications, depending on the complexity of the target sequence, an oligonucleotide probe typically contains about 10 to 100, 15 to 50, or 15 to 25 nucleotides. In certain diagnostic applications, a polynucleotide probe contains about 100-1000 nucleotides, 300-600 nucleotides, preferably about 300 nucleotides. The probes herein are selected to be "substantially" complementary to different strands of a particular target sequence. This means that the probes must be sufficiently complementary to specifically hybridize or anneal with their respective target sequences under a set of predetermined conditions. Therefore, the probe sequence need not reflect the exact complementary sequence of the target. For example, a noncomplementary nucleotide fragment may be attached to the 5' or 3' end of the probe, with the remainder of the probe sequence being complementary to the target sequence. Alternatively, noncomplementary bases or longer sequences can be interspersed into the probe provided that the probe sequence has sufficient complementarity with the sequence of the target polynucleotide to specifically anneal to the target polynucleotide. A peptide or polypeptide probe may be any molecule to which the protein or peptide specifically binds, including DNA (for DNA binding proteins), antibodies, cell membrane receptors, peptides, cofactors, lectins, sugars, polysaccharides, cells, cell membranes, organelles and organellar membranes.

The terms "sample" and "specimen" mean any animal tissue or fluid containing polynucleotides, including cells and other tissue containing DNA and RNA. Examples include: thyroid, blood, connective, epithelial, lymphoid, muscle, nervous, sputum, and the like. A sample may be solid or liquid and may contain DNA, RNA, cDNA, for example, bodily fluids such as blood or urine, cells, cell preparations or soluble fractions or media aliquots thereof, chromosomes, organelles, and the like.

The term "specifically bind" means a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

The term "specifically hybridize" means an association between two single stranded polynucleotides of sufficiently complementary sequence to permit such hybridization under predetermined conditions generally used in the art (sometimes termed "substantially complementary"). For example, the term may refer to hybridization of a polynucleotide probe with a substantially complementary sequence contained within a single stranded DNA or RNA molecule according to an aspect of the invention, to the substantial exclusion of hybridization of the polynucleotide probe with single stranded polynucleotides of non-complementary sequence.

The term "stringent conditions" means (1) hybridization in 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C., (2) hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 mg/ml), 0.1% SDS, and 10% dextran sulfate at 42° C.; with washes at 42° C. in 0.2×SSC and 0.1% SDS or washes with 0.015 M NaCl, 0.0015 M sodium citrate, 0.1% $Na_2SO_4$ at 50° C. or similar art-recognized procedures employing similar low ionic strength and high temperature washing agents and similar denaturing agents.

The term "useful variations" means (1) for a polynucleotide, the complements of the polynucleotide; the homologs of the polynucleotide and its complements; the variants of the polynucleotide, its complements, and its homologs; and the fragments of the polynucleotide, its complements, its homologs, and its variants and (2) for a polypeptide, the homologs of the polypeptide; the variants of the polypeptide and its homologs; and the fragments of the polynucleotide, its homologs, and its variants.

The term "variant" means (1) a polynucleotide sequence containing any substitution, variation, modification, replacement, deletion, or addition of one or more nucleotides from or to a polynucleotide sequence and that has the same or substantially the same properties and performs the same or substantially the same function as the original sequence and (2) a polypeptide sequence containing any substitution, variation, modification, replacement, deletion, or addition of one or more amino acids from or to a polypeptide sequence and that has the same or substantially the same properties and performs the same or substantially the same function as the original sequence. The term therefore includes single nucleotide polymorphisms (SNPs) and allelic variants and includes conservative and non-conservative amino acid substitutions in polypeptides. The term also encompasses chemical derivatization of a polynucleotide or polypeptide and substitution of nucleotides or amino acids with nucleotides or amino acids that do not occur naturally, as appropriate.

Unless otherwise specified, all percentages and amounts expressed herein and elsewhere in the specification should be understood to refer to percentages by dry weight. The amounts given are based on the active weight of the material.

As used herein, methods to "treat" an animal suffering from a disease, disorder, or condition is also meant to encompass methods to prevent or to cure, reverse, attenuate, alleviated, ameliorate, minimize, suppress, or halt the deleterious effects of the disease, disorder, or condition as well.

The compositions disclosed herein may comprise, consist essentially of, or consist of any of the components described herein.

The invention is not limited to the particular methodology, protocols, and reagents described herein because they may vary. Further, the terminology used herein is for the purpose of describing particular embodiments only and is not intended to limit the scope of the present invention.

Hyperthyroidism

Hyperthyroidism is characterized by hypermetabolism of the thyroid gland and excessive production of the thyroid hormones triiodothyronine ($T_3$) and tetraiodothyronine (thyroxine or $T_4$). Most of the $T_3$ and $T_4$ are bound to serum proteins. The portion of $T_3$ and $T_4$ partitioned into serum, and not associated with protein, is called free $T_3$ ($fT_3$) and $T_4$ ($fT_4$). One skilled in the art can accurately diagnose hyperthyroidism in a feline utilizing thyroid function tests, examining clinical signs, and by observing the animal's response to trial thyroid hormone administration. Thyroid function tests are known to those skilled in the art and include, for example, tests for determining the concentrations of total and free serum $T_3$ and $T_4$, tests for determining the concentration of thyroid stimulating hormone (TSH), and the sodium pertechnetate and $T_3$ suppression tests. See, for example, *Small Animal Nutrition*, pages 863-868 (2000). As noted above, treating hyperthyroidism as used herein encompasses ameliorating, suppressing, and eradicating hyperthyroidism.

As depicted in FIG. 1, biosynthesis of thyroxine (T4) is carried out in follicular cells of the thyroid gland. In this process, iodide is first transported across the basement membrane of follicular cells via the $Na^+/I^-$ (sodium/iodide) symporter and then moved across the apical membrane into the colloid of the follicle, via the pendrin transporter. The polypeptide, thyroglobulin (TG) is synthesized in the endoplasmic reticulum of the follicular cell and secreted into the colloid. Thyroid peroxidase (PTO) oxidizes iodide ($I^-$) to $I^0$, the more reactive species, which iodinates tyrosyl moieties of the thyroglobulin polypeptide in a hydrogen peroxide mediated reaction. It is believed that production of hydrogen peroxide is mediated by thyroid oxidase (ThOX). Reaction between phenolic residues of the iodinated tyrosyl moieties provides the dual-ring precursors of $T_4$ thyroxine and $T_3$ triiodothyronine. This latter reaction is also believed to be mediated by the thyroid peroxidase/$H_2O_2$ system, in which an iodinated tyrosyl phenolic ring is cleaved and joined to an iodinated tyrosine via an ether linkage.

Thyroid-stimulating hormone (TSH), released from the pituitary gland, binds to the thyroid-stimulating hormone receptor (TSHR), a transmembrane G-protein coupled receptor of the basolateral membrane of the cell, stimulating, inter alia, accumulation of cAMP, protein iodination, and endocytosis of the colloid. The endocytosed vesicles fuse with lysosomes in the cell, in which the thyroglobulin carrying the iodinated dual-ring precursors of $T_4$ thyroxine and $T_3$ triiodothyronine, is proteolytically degraded to release $T_4$ thyroxine and $T_3$ triiodothyronine

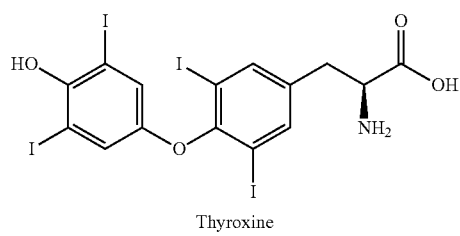

Thyroxine

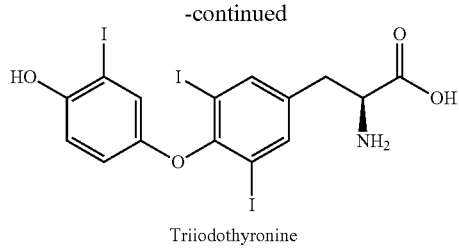

Triiodothyronine

Intrathyroidal 5'-deiodinase, is a selenium-containing enzyme that can convert $T_4$ thyroxine to the active hormone, $T_3$ triiodothyronine. It should also be noted that the thyroid gland actively traps iodine to ensure an adequate supply of the thyroid hormones.

The primary regulator of the synthesis of $T_4$ thyroxine and $T_3$ triiodothyronine is thyroid stimulating hormone (TSH), as noted above. This stimulatory activity is subject a feedback mechanism, through which the levels of TSH are suppressed by circulating $T_4$ thyroxine and $T_3$ triiodothyronine. Accordingly, one biological marker of hyperthyroidism (higher levels of circulating $T_4$ thyroxine and $T_3$ triiodothyronine) is a lower level of thyroid stimulating hormone (TSH). Chemiluminescent assays permit detection of TSH at levels at or below 0.05 U/mL, which levels are generally diagnostic of hyperthyroidism.

Triiodothyronine, $T_3$, acts on the majority of tissues in the body, increasing the basal metabolic rate, and, therefore, the body's consumption of oxygen and energy. One mechanism through which Triiodothyronine ($T_3$) acts is the stimulation of gene expression. For example, among its biological actions, triiodothyronine ($T_3$) binds a protein, thyroid hormone receptor activator molecule, and the complex so-formed is apparently involved in the stimulation of transcription of the gene encoding the thyroid hormone receptor (TR).

It has been observed, using the methods and reagents described herein, that in hyperthyroid animals, the expression and activity of a number of the above proteins and polypeptides is substantially elevated (see FIG. 1 and Table 1).

TABLE 1

| Transcript | Gene Name | Fold Increase In Hyperthyroid Cats |
|---|---|---|
| NIS | Sodium iodide symporter | 2.7 |
| TPO | Thyroid peroxidase | 1.9 |
| TSHR | Thyroid stimulating hormone receptor | 1.6 |
| IT | Pendrin iodine transporter | 1.4 |
| THOX | Thyroid oxidase | 1.4 |

As the data of Table 1 demonstrated, in hyperthyroid cats, expression of sodium/iodide transporter (NIS) is increased by a factor of 2.7, the activity of thyroid peroxidase (TPO) is increased by a factor of 1.9, the activity of thyroid stimulating hormone receptor (TSHR) is increased by a factor of 1.6, the activity of iodide transporter (IT; Pendrin) is increased by a factor of 1.4, and the activity of thyroid oxidase (ThOX) is increased by a factor of 1.4.

In view of the data of Table 1, for example, it can be inferred that genes, transcripts, proteins, and polypeptides identified as involved in a disease or condition in one genus or species are also involved in the comparable disease or condition in another genus or species. Support for such inferences are readily established by identifying the corresponding genes, transcripts, proteins, and polypeptides in the second species and measuring their levels of expression in normal and afflicted animals, using methods and materials well known in the art. Such tools include, but are not limited to genome analysis, and comparative genome analyses (e.g., human vs. feline), bioinformatics, proteome and transcriptome analyses of normal vs. afflicted animals. Homologous genes can be identified and isolated using hybridization methods and polymerase chain reaction (PCR) amplifications, and other methods and approaches known to those skilled in the art.

Identification of polypeptides involved in the etiology may be found in the literature or may involve, e.g., performing transcription and proteomic analyses on tissues of healthy animals as compared to tissues from animals afflicted with the target disease. Such analyses would indicate which proteins might be involved in the etiology of the target disease as well as whether an increase or decrease in expression could be correlated with the existence and severity of the disease or condition. Additional information would be available using, e.g., inbred animals (mice) that are afflicted, or genetically-engineered to be afflicted with the target disease or condition. In further aspects, identifying a polypeptide involved in the etiology underlying the target disease or condition, and determining whether an increase or a decrease in activity or expression of said identified polypeptide would ameliorate the target disease or condition, could be facilitated using cells cultures propagated from healthy tissue as well as the corresponding tissue from an afflicted animal. In such systems, the activity of a target protein in both healthy and afflicted tissue could be established by biochemical assays using methods generally known in the art or readily developed using reagents and procedures generally known in the art.

In practicing the present invention, many conventional techniques in molecular biology may be used, including the construction of recombinant vectors, expression systems, and transformed cells and cell lines comprising such recombinant vectors, expression systems containing and expressing, e.g, the feline NIS gene, the nuclear thyroid hormone receptor gene, and genes encoding reporter polypeptides, particularly those in operative association with a thyroid hormone response element. Illustrative reporter polypeptides include but are not limited to β-galactosidase, HcRed, DsRed, DsRed monomer, ZsGreen, AmCyan, ZsYellow, fire fly luciferase, lac Z, renilla luciferase, SEAP, enhanced green fluorescent protein (eGFP), d2EGFP, enhanced blue fluorescent protein (eBFP), enhanced yellow fluorescent protein (eYFP), and GFPuv, enhanced cyan fluorescent protein (eCFP), cyan, green yellow, red, and far red Reef Coral Fluorescent Protein, human alpha-1-antitrypsin (hAAT) and/or fragments, modifications or functional variants thereof.

In certain embodiments, determining "protein expression levels," "gene expression," or "gene expression levels" as used herein includes, but is not limited to, determining either corresponding RNA, protein, or peptide levels (or combinations thereof). The methods of the present disclosure are not limited to a particular method for determining protein, peptide, or RNA levels, all of which are well known in the art. Moreover, gene expression and gene expression levels can be assessed in any cell or tissue that is appropriate for expression of the gene of interest. In one embodiment, where appropriate, gene expression is assessed in blood cells. Other cell types include, but are not limited to, thyroid gland cells, muscle cells, nerve cells, glial cells, endothelial cells, skin cells, liver cells, kidney cells, and bone cells. The cells may be primary cells, i.e., taken directly from an animal, such as cells isolated from recently drawn blood or biopsied tissues. The cells may also be non-primary, i.e., an established cell line through passage or even an immortalized cell line, such that the methods determining gene expression levels can be performed on established animal cell lines, e.g., CHO cells, prior to administration of a composition to an animal.

Multivariate analysis of gene expression profiles of felines (cats) diagnosed as hyperthyroid as well as healthy, age-matched, non-hyperthyroid felines (cats) revealed that these two groups of animals could be distinguished based upon a set of differentially-expressed genes. Within this larger set were five genes involved in thyroid hormone biosynthesis that were expressed at higher levels in the hyperthyroid cats. Among these, the gene with the highest level of expression in thyroid tissue of hyperthyroid cats was the sodium iodide symporter (NIS).

The present disclosure therefore provides an isolated gene fragment encoding a portion of the feline sodium/iodine symporter protein (NIS protein) that has the nucleotide sequence of SEQ ID NO:1, and that encodes a peptide having the amino acid sequence of SEQ ID NO: 2.

Also provided herein are recombinant vectors and transformed cells comprising the isolated feline NIS gene fragment. The present disclosure also provides methods involving the use of such isolated DNA molecules to establish gene expression profiles for the feline NIS gene in healthy and afflicted animals and measurement of NIS gene expression profiles in the presence and absence of food ingredients and extracts thereof for those genes for the design of pet food compositions suitable for administration to feline companion animals afflicted with hyperthyroidism. The present disclosure also provides compositions and methods of treatment of hyperthyroidism in felines.

NIS Gene Expression in Hyperthyroid Felines and Methods Based Thereon

The methods of the present disclosure are based, in part, on the discovery that particular gene expression profiles in felines correlate with a change in such animal from a normal to a hyperthyroid condition. Correlation of a particular gene expression profile with the presence and severity of hyperthyroidism can be predicted, detected and diagnosed in a feline without rendering a conventional clinical diagnosis based on art-recognized clinical signs and symptoms.

In one embodiment, the present invention encompasses one or more genes or gene segments ("genes" as defined herein) that are differentially expressed in abnormal animals compared to normal animals. The invention is based upon the discovery of polynucleotides that are differentially expressed in abnormal animals compared to normal animals. The genes were identified by comparing the expression of genes in tissue samples taken from animals diagnosed as abnormal with genes in tissue samples from animals diagnosed as normal using Affymetrix GeneChip® technology.

The polynucleotides and genes are identified by measuring differences in gene expression from tissue samples taken from felines diagnosed as abnormal, i.e., hyperthyroid, with gene expression in tissue samples from felines diagnosed as normal. Changes in gene expression can be determined by any method known to skilled artisans. Generally, changes in gene expression are determined by measuring transcription (determining the amount of mRNA produced by a gene) or measuring translation (determining the amount of protein produced by a gene). The amount of RNA or protein produced by a gene can be determined using any method known to skilled artisans for quantifying polynucleotides and proteins.

Generally, mRNA expression is determined using polymerase chain reaction (PCR) (including, without limitation, reverse transcription-PCR(RT-PCR) and quantitative real-time PCR (qPCR)), short or long oligonucleotide arrays, cDNA arrays, EST sequencing, Northern blotting, SAGE, MPSS, MS, bead arrays and other hybridization methods. The RNA measured is typically in the form of mRNA or reverse transcribed mRNA.

Protein or polypeptide expression is determined using various colorimetric and spectroscopic assays and methods such as quantitative Western blots, ELISA, 2D-gels, gas or liquid chromatography, mass-spectroscopy.

Gene chips allow a large-scale study of biological processes and the measurement of activity within a cell at a certain point in time. Microarray analysis permits one to account for differences in phenotypes on a large-scale genetic basis. Actual measurement of gene expression products is a more accurate indicator of gene function than determining sequences per se. Microarray analysis is based upon quantifying the concentration of a gene's mRNA transcript in a cell at a given time. DNA is immobilized on a medium and labeled target mRNA is hybridized with probes on the array. Binding of the labeled mRNA to the probes is measured by laser analysis. The measurement is a count of photons emitted. The entire chip is scanned and digitally imaged. The image is processed to locate probes and to assign intensity measurements to each probe. In this manner up- and down-regulated genes may be determined. The analysis enables the skilled person to find groups of genes with similar expression profiles and to determine tissues with similar expression profiles. In this manner, genes that explain the observed differences in tissue samples can be identified.

Affymetrix Gene Chips typically employ probes of 25 bp and probe sets of 11 to 20 probes corresponding to a particular gene or EST. The chip is constructed with a perfect match and mismatch probe of 25 bp each, the former being perfectly complementary to a specific region of a gene and the latter having the $13^{th}$ bp substituted to make a mismatch. A probe summarization algorithm is used to determine background correction, normalization and probe summarization, which is the conversion of probe values to probe set expression values. RMA is one of the algorithms that may be used for this purpose. The algorithm performs the last two steps of analysis, normalization and summarization of probe-level intensity measurements. The perfect match values are, therefore, background corrected, normalized and summarized into a set of expression measurements.

The raw data are analyzed using GeneSpring version 7.0 (GS) software (Agilent Corporation) and validated using the R-Bioconductor (RB) freeware. Both software packages are used to compute probe intensities from the CEL files generated by the Affymetrix Instrument. The Present/Absent/Marginal calls per probe and P-values are computed using the R-Bioconductor and GeneSpring software separately.

Generally, differential gene expression in abnormal animals compared to normal animals is determined by measuring the expression of at least one gene. In certain embodiments, the expression of two or more differentially expressed genes is measured to provide a gene expression pattern or gene expression profile. In other embodiments, the expression of a plurality of differentially expressed genes is measured to provide additional information for a more significant gene expression pattern or profile.

In another aspect, the present disclosure provides a device suitable for detecting the expression of a plurality of genes differentially expressed in abnormal felines compared to normal felines. The device comprises a substrate having a plurality of the oligonucleotide or polynucleotide probes of the present invention affixed to the substrate at known locations. The device is essentially an immobilized version of the oligonucleotide or polynucleotide probes described herein. The device is useful for rapid and specific detection of genes and polynucleotides and their expression patterns and profiles. Typically, such probes are linked to a substrate or similar solid support and a sample containing one or more polynucleotides (e.g., a gene, a PCR product, a ligase chain reaction (LCR) product, a DNA sequence that has been synthesized using amplification techniques, or a mixture thereof) is exposed to the probes such that the sample polynucleotide(s) can hybridize to the probes. The probes, the sample polynucleotide(s), or both, are labeled, typically with a fluorophore or other tag such as streptavidin, and detected using methods known to skilled artisans. If the sample polynucleotide(s) is labeled, hybridization may be detected by detecting bound fluorescence. If the probes are labeled, hybridization is typically detected by label quenching. If both the probe and the sample polynucleotide(s) are labeled, hybridization is typically detected by monitoring a color shift resulting from proximity of the two bound labels. A variety of labeling strategies and labels are known to skilled artisans, particularly for fluorescent labels. Preferably, the probes are immobilized on substrates suitable for forming an array (known by several names including DNA microarray, gene chip, biochip, DNA chip, and gene array) comparable to those known in the art.

Methods for determining the amount or concentration of protein in a sample are known to skilled artisans. Such methods include radioimmunoassays, competitive-binding assays, Western blot analysis, and ELISA assays. For methods that use antibodies, polyclonal and monoclonal antibodies are suitable. Such antibodies may be immunologically specific for a protein, protein epitope, or protein fragment.

Some embodiments of the invention utilize antibodies for the detection and quantification of proteins produced by expression of the polynucleotides of the present invention. Although proteins may be detected by immunoprecipitation, affinity separation, Western blot analysis, protein arrays, and the like, a preferred method utilizes ELISA technology wherein the antibody is immobilized on a solid support and a target protein or peptide is exposed to the immobilized antibody. Either the probe, or the target, or both, can be labeled using known methods.

In a further aspect, the invention provides a method for detecting the differential expression of one or more genes differentially expressed in abnormal felines compared to normal felines in a sample. The method comprises (a) hybridizing a combination comprising a plurality of polynucleotide probes that are differentially expressed in abnormal felines compared to normal felines with polynucleotides in the sample to form one or more hybridization complexes; (b) optionally, hybridizing a combination comprising a plurality of polynucleotide probes that are differentially expressed in abnormal felines compared to normal felines with polynucleotides in a standard to form one or more hybridization complexes; (c) detecting the hybridization complexes from the sample and, optionally, the standard from step (b); and (d) comparing the hybridization complexes from the sample with the hybridization complexes from a standard, wherein a difference in the amount of hybridization complexes between the standard and sample indicate differential expression of genes differentially expressed in abnormal animals compared to normal animals in the sample.

Step (b) and part of step (c) are optional and are used if a relatively contemporaneous comparison of two or more test systems is to be conducted. However, in a preferred embodiment, the standard used for comparison is based upon data previously obtained using the method.

These probes are exposed to a sample to form hybridization complexes that are detected and compared with those of a standard. The differences between the hybridization complexes from the sample and standard indicate differential expression of polynucleotides and therefore genes differentially expressed in abnormal felines compared to normal felines in the sample. In certain embodiments, probes are made to specifically detect polynucleotides or fragments thereof produced by one or more of the genes or gene fragments identified by the present invention. Methods for detecting hybridization complexes are known to skilled artisans.

In another aspect, the invention provides a method for detecting the differential expression of genes differentially expressed in abnormal felines compared to normal felines in a sample. The method comprises (a) reacting a combination comprising a plurality of polypeptide probes with proteins in the sample under conditions that allow specific binding between the probes and the proteins to occur, wherein the proteins bound by the probes are differentially expressed in an abnormal feline compared to a normal feline; (b) optionally, reacting a combination comprising a plurality of polypeptide probes with proteins in a standard under conditions that allow specific binding between the probes and the proteins to occur, wherein the proteins bound by the probes are differentially expressed in an abnormal feline compared to a normal feline; (c) detecting specific binding in the sample and, optionally, the standard from step (b); and (d) comparing the specific binding in the sample with that of a standard, wherein differences between the specific binding in the standard and the sample indicate differential expression of genes differentially expressed in abnormal felines compared to normal felines in the sample.

These probes are exposed to a sample to form specific binding that is detected and compared with those of a standard. The differences between the specific binding from the sample and standard indicate differential expression of proteins and therefore genes differentially expressed in abnormal felines compared to normal felines, particularly abnormal-associated genes, in the sample. In a preferred embodiment, probes are made to specifically detect proteins or fragments thereof produced by one or more of the genes or gene fragments identified by the present invention.

In one embodiment, the method further comprises exposing the feline or sample to a test substance before reacting the polypeptides with the proteins. Then, the comparison is indicative of whether the test substance altered the expression of genes differentially expressed in abnormal felines compared to normal felines, particularly abnormal-associated genes, in the sample.

The invention thus provides, a method of diagnosing the existence and severity of hyperthyroidism in a feline comprising measuring the level of expression of the NIS biomarkers in a biological sample from the feline, wherein differences in expression of the NIS gene relative to a control value for expression in a sample from a normal animal indicates the existence and reflects the severity of hyperthyroidism, according to any of the following illustrative methods:

According to this method, the level of expression of the NIS biomarker is determined by measuring gene expression using either (i) a DNA microarray comprising one or more oligonucleotides complementary to mRNA or cDNA corresponding to the NIS gene, or (ii) a quantitative polymerase chain reaction with oligonucleotide primers for mRNA or cDNA corresponding to the NIS gene.

According to this method, the step of measuring gene expression of the NIS biomarker comprises (i) isolating RNA from the tissue sample, (ii) reverse transcribing the RNA to obtain the corresponding cDNA, (iii) isolating and fragmenting the cDNA thus obtained, (iv) contacting the cDNA fragments with a DNA microarray comprising one or more oligonucleotides complementary to cDNA corresponding to the one or more biomarkers to be measured, and (v) detecting hybridization between the cDNA fragments and the one or more oligonucleotides in the DNA microarray. In certain aspect of this embodiment, the hybridization between the cDNA fragments and the one or more oligonucleotides in the DNA microarray is under stringent conditions.

In another embodiment, the level of expression of the NIS biomarker is detected by an antibody to the expressed protein. In this embodiment, the NIS biomarker is detected by an immunoassay selected from a competitive binding assay, a non-competitive binding assay, a radioimmunoassay, an enzyme linked immunosorbent assay (ELISA), a sandwich assay, a precipitin reaction, a gel diffusion immunodiffusion assay, an agglutination assay, a fluorescent immunoassay, chemiluminescence immunoassay, immunoPCR immunoassay, a protein A or protein G immunoassay and an immunoelectrophoresis assay.

In one aspect of this embodiment, the foregoing method which is an enzyme-linked immunosorbent assay (ELISA), or a lateral flow immunochromatographic assay. In other aspects of this embodiment, the level of expression of the biomarker is detected by quantitative mass spectroscopy measuring the expressed protein in the biological sample, or the NIS biomarker is detected by an aptamer recognizing the expressed protein, where the aptamer can be an oligonucleotide or a peptide.

In certain aspects, the level of expression of the NIS biomarkers in the biological sample of a hyperthyroid animal, relative to a control value for expression in sample from a non-afflicted animal, is increased in an afflicted animal as compared to a non-afflicted animal, is increased by a factor of 1.25, 1.3, 1.4, 1.5, 1.6, 1.7, 1.8, 1.9, 2.0, 2.1, 2.2, 2.3, 2.4, 2.5, 2.6, 2.7, 2.8, 2.9, or 3 fold or greater. In other aspects, the level of expression of the NIS biomarkers in the biological sample of an afflicted animal is reduced, e.g., by a factor of 1.25, 1.3, 1.4, 1.5, 1.6, 1.7, 1.8, 1.9, 2.0, 2.1, 2.2, 2.3, 2.4, 2.5, 2.6, 2.7, 2.8, 2.9, or 3 fold or greater. In certain embodiment, the NIS biomarker is detected in vitro, in an appropriate cell culture model system.

In other aspects of these embodiments, the level of expression of the NIS biomarker in the biological sample is one or at least one standard deviation higher or lower than the mean expression of that biomarker in a normal sample. In still other aspects of these embodiments, the level of expression of the NIS biomarker in the biological sample is normalized relative to expression of one or more genes known to have relatively constant expression.

In another embodiment, the disclosure provides a method of treating, hyperthyroidism in a feline in need thereof, comprising diagnosing the existence of hyperthyroidism, using, e.g., the methods disclosed above, and managing the condition, for example by diet alone or in combination with appropriate medication. In one aspect of this embodiment, the diet includes one or more components identified by the methods disclosed herein, which components are useful for reducing iodine uptake by the thyroid gland or for inhibiting synthesis of thyroid hormone, including, inter alia, components capable of depressing or inhibiting NIS gene expression or reducing or inhibiting NIS protein function.

In a further embodiment, the invention provides reagents, optionally labeled, useful in the detection of the level of expression of the NIS biomarker in a feline. Such reagents may include, e.g., antibodies, for example monoclonal antibodies, single chain antibodies, and functional antibody fragments, that selectively recognize the feline NIS protein, e.g., antibodies, for example monoclonal antibodies, single chain antibodies, and functional antibody fragments, that selectively recognize the peptide of SEQ ID NO:2. Other such reagents include aptamers, for example nucleic acid or peptidic aptamers, that selectively recognize the feline NIS protein or the peptide of SEQ ID NO:2, as well as oligonucleotide probes capable of selectively hybridizing to the feline NIS gene or to the nucleotide sequence of SEQ ID NO:1.

In a further embodiment, the present disclosure provides a kit (Kit 1) for the diagnosis, prognosis or monitoring of hyperthyroidism in a feline, comprising means for measuring expression of the feline NIS gene, in a biological sample from the feline, and instructions for using such means to measure expression the NIS gene in a biological sample from the feline and evaluating the presence of a process leading to a hyperthyroidism in a feline. The kit means measuring the one or more biomarkers is one or more nucleic acid probes capable of detecting gene expression of the NIS gene, which probes are capable of selectively hybridizing to the nucleic acid of SEQ ID NO:1 under stringent conditions.

In other aspects of these embodiments, the means for measuring the one or more biomarkers is one or more antibodies capable of detecting gene expression of the NIS gene by selectively recognizing the expressed NIS protein, or by selectively recognizing the peptide of SEQ ID NO:2. Such kits may be in an ELISA format comprising antibody capable of detecting the NIS protein, including an isolated, purified or recombinant NIS protein corresponding to the expressed protein or the peptide sequence of SEQ ID NO:2, and buffer.

In still other aspects of this embodiment, the means for measuring the NIS biomarker is one or more aptamers, e.g., as hereinbefore described, capable of detecting gene expression of the NIS protein or by recognizing the expressed NIS protein.

In one embodiment, the present disclosure provides a method for diagnosing hyperthyroidism in a subject feline. This method comprises determining the level of the peptide of SEQ ID NO: 2 found in a biological sample of a feline to be tested for hyperthyroidism and then comparing that level to a reference level of that peptide established in healthy felines, i.e., those known not to be afflicted with hyperthyroidism. An increased level of the peptide of SEQ ID NO: 2 in the tested feline is diagnostic of hyperthyroidism, and the extent of that increase is indicative of the severity of the condition.

In certain aspects of this embodiment, the level of the peptide of SEQ ID NO:2 can be determined by methods described herein as well as according to those know in the art. In specific aspects of this embodiment, the determination of the level of the peptide of SEQ ID NO:2 is carried out using an antibody, an antibody fragment, or an aptamer as indicator. In particular aspects, the indicator is a monoclonal antibody while in others, it is an Fab fragment, an F(ab')2 fragment, an Fv fragment, or an aptamer.

In a further embodiment, the present disclosure provides a method of diagnosing hyperthyroidism in a subject feline, which comprises determining the level of a nucleic acid encoding the peptide of SEQ ID NO:2 in a biological sample of the subject feline, and then comparing that value to a reference level of that nucleic acid established in control felines without hyperthyroidism. According to this method, an increased level of the nucleic acid in the subject feline sample, as compared to the reference level, is diagnostic of hyperthyroidism in the subject feline. In certain aspects of this embodiment, the level of the nucleic acid is determined using methods comprising the use of quantitative RT-PCR. In another aspect of this embodiment, the level of the nucleic acid is determined using methods comprising the use of microarrays, including those in which the microarray comprises a plurality of isolated polynucleotides selected from the group consisting of RNA, DNA, cDNA, PCR products, or ESTs, in which the polynucleotide encodes at least a portion of the peptide of SEQ ID NO:2. In a specific aspect of this embodiment, the nucleic acid is RNA.

The present disclosure also provides a method for monitoring hyperthyroidism in an afflicted feline. This method comprises determining a first level of the peptide of SEQ ID NO: 2 in a biological sample from the subject feline at a first time point, followed by determining a second level of the peptide of SEQ ID NO: 2 in a biological sample from the subject feline at a second, subsequent time point. The two levels are compared and an increase in the level of the peptide of SEQ ID NO: 2 with time indicates progression of hyperthyroidism, and a decrease in level of the peptide of SEQ ID NO: 2 with time indicates regression of hyperthyroidism.

In another embodiment, the present disclosure also provides a method for monitoring hyperthyroidism in an afflicted feline, which comprises determining a first level of nucleic acid encoding the peptide of SEQ ID NO: 2 in a biological sample from the subject feline, followed by determining a second level of nucleic acid encoding the peptide of SEQ ID NO: 2 in a biological sample from the subject feline at a second, later time point. The two values are compared and an increase in the level of the nucleic acid encoding the peptide of SEQ ID NO: 2 with time indicates progression of hyperthyroidism, and a decrease in level of the level of the nucleic acid encoding the peptide of SEQ ID NO: 2 with time indicates regression of hyperthyroidism.

The present disclosure also provides kits useful in these methods. In one embodiment, the present disclosure provides a kit comprising means for measuring the level of expression of the feline NIS gene in a biological sample from a subject feline. The means used for this determination can comprise at least one indicator selected from the group consisting of nucleic acid probes, antibodies, antibody fragments, and aptamers, in which the indicator is capable of detecting expression of the feline NIS gene in a biological sample from the subject feline, using methods described herein as well as those known in the art. In one aspect of this embodiment, the kit includes instructions for using the above means to measure expression the feline NIS gene in the biological sample from said feline. In particular aspects of this embodiment, the means employed include an antibody or an antibody fragment that specifically recognizes the peptide of SEQ ID NO:2. In another aspect of this embodiment, the means employed comprises a first and a second oligonucleotide, in which the first oligonucleotide specifically hybridizes to the noncoding strand of the nucleic acid of SEQ ID NO:1 and wherein the second oligonucleotide specifically hybridizes to the coding strand of the nucleic acid of SEQ ID NO:1. The combination of these two oligonucleotides can be used for PCR amplification of a portion of the DNA molecule of SEQ ID NO:1 encoding the peptide of SEQ ID NO:2.

Additional diagnostic methods, kits, and compositions, based upon the presently disclosed nucleic acid and peptide sequences can be developed using the reagents and procedures described in co-owned application Ser. No. 12/600,064 and application Ser. No. 13/054,745, both of which are hereby incorporated by reference in their entireties.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

Functional Gene Profile

The present disclosure provides isolated genes and methods using those genes for the rational design of compositions useful for improving the health of a feline companion animal afflicted with hyperthyroidism Nutritional genomics ("nutrigenomics") is a relatively new branch of genomic research in humans that has emerged as the interface between nutritional environment and cellular and genetic processes. Nutrigenomics seeks to provide a genetic understanding for how dietary components and/or nutrition affect the balance between health and disease, for example by altering the expression and/or structure of an individual's genetic makeup. Some dietary components have been shown to alter gene expression in a number of ways. For example, they may act as ligands for proteins such as transcription factors or receptors, may be metabolized by primary or secondary metabolic pathways, thereby altering concentrations of substrates or intermediates, or may be involved in signal pathways.

Functional genomic profile: The term "phenotype" as used herein refers to the totality, or any part thereof, of observable characteristics, whether functional or otherwise, of an organism as determined by the genotype of the organism. The term "genotype" refers to the total genetic constitution of an organism, or any part thereof. The genotype comprises genetic information carried both in chromosomes and extrachromosomally.

The phrase "functional gene profile" as it used herein refers to the whole or any part of the functional consequences of expression of defined gene sequences, including the production and function of mRNAs, proteins and metabolites related to the activity of the specific genes. A functional gene profile (FGP) can be established using genomic, proteomic or metabolomic approaches, or any combination of these.

The functional gene profile of each of the gene disclosed herein, the feline NIS gene, therefore can be defined by its expression and activity, as reflected in its transcribed mRNA, the amount of the encoded protein, the biological activity of that protein and metabolites produced by its activity. Each of these indicators can be measured using methods disclosed herein as well as those known in the art. These gene profiles are established in both healthy felines as well as those afflicted with hyperthyroidism, allowing a correlation between gene expression and the presence and severity of hyperthyroidism in felines. These gene profiles are also established in both healthy felines as well as those afflicted with hyperthyroidism with and without administration of a bioactive dietary component.

The data underlying the functional gene profile can be generated from biofluid and/or tissue samples by any technique known in the art of functional genomics. Examples of techniques useful in generating functional genomic analysis include, without limitation, the following techniques that can be used individually or in combination: (a) single and multicolor gene and protein arrays and microarrays in low and high density formats, for example on glass, silica, plastic, membrane or bead supports or combinations thereof, including for example Northern blot analysis and Western blot analysis; (b) mass spectrometry techniques using quadrupole, time of flight, quadrupole ion trap or Fourier-transform ion cyclotron resonance mass spectrometers or combinations thereof, with various ionization sources including without limitation matrix-assisted laser desorption ionization, electrospray ionization, nanospray ionization and surface-enhanced laser desorption ionization; (c) polymerase chain reaction (PCR) techniques including single and multiplexed quantitative real-time PCR techniques; (d) gel electrophoresis (single or multidimensional) including two-color 2D gel methodologies, SDS-polyacrylamide gel electrophoresis (SDS-PAGE), and 2D PAGE; and (e) liquid chromatography (single or multidimensional) by itself or in tandem with mass spectrometry techniques.

The functional gene profile can be generated from raw image, numerical and/or text data sets, typically after normalization and pre-processing to reduce or remove data noise. Techniques that can be used to recognize the functional gene profile include without limitation nearest neighbor pattern recognition, neural networks, hidden Markov models, Bayesian networks, genetic algorithms, support vector machines, and combinations thereof.

The functional gene profile of the feline genes disclosed herein, which can be measured in healthy felines, felines afflicted with mild hyperthyroidism, felines afflicted with severe hyperthyroidism, or an animal model, or of a tissue or cell thereof, can therefore be in a "normal" or "extranormal" state. A "normal" functional gene profile for the disclosed genes is that determined in an animal exhibiting a state of wellness as defined herein, and generally indicative of such a state. Typically a "normal" functional gene profile is associated with homeostasis, i.e., a tendency to stability in bodily functions arising, for example, from internal control systems activated by negative feedback. An "extranormal" functional gene profile is one that is outside the range identified as "normal," and that can be correlated with the presence of hyperthyroidism in the felines tested. Such an "extranormal" functional gene profile can be associated with a breakdown in homeostasis; thus there is often a tendency for an "extranormal" functional gene profile to drift further from normality with the passage of time and progression of the hyperthyroidism, e.g., from mild to severe, absent intervention (for example by a method of the present invention) to halt or reverse such drift. If unchecked, this progressive drift away from normality can ultimately lead to death. An "extranormal" functional gene profile is therefore often indicative of and associated with a state adverse to wellness, for example a state of disease or physiological disorder, in an animal, which, in the present context, is hyperthyroidism. Such a state can be outwardly evident, or can be latent (i.e., asymptomatic). An "extranormal" functional gene profile can, in some situations, indicate a predisposition, whether hereditary or otherwise, to disease, e.g., hyperthyroidism, and in such situations a shift in functional gene profile towards a more normal state (for example by a method of the present invention) can be effective in disease prevention or prophylaxis.

In certain embodiments, a subpopulation of felines can be identified, e.g., as mildly or as severely afflicted with hyperthyroidism, at least in part by physiological condition. The term "physiological condition" herein refers to any one or combination of physical, pathological, behavioral and biochemical attributes of an animal including its size, weight, age, activity level, disposition, and state of wellness or disease, e.g., as defined by the levels of either or both of triiodothyronine ($T_3$) and tetraiodothyronine (thyroxine or $T_4$). Physiological condition is a product of interaction of the genotype with the environment of the animal.

Biofluid and Tissue Samples: A biofluid or tissue sample useful herein can be any such sample that is amenable to gene, proteomic and/or metabolomic analysis. For gene analysis, the sample must provide DNA in a quantity that may or may not need amplification, for example through PCR techniques. Samples lacking DNA or RNA, as is often the case, for example, with urine samples, can nonetheless provide useful proteomic and/or metabolomic information.

Biofluids that can be sampled include excreta (feces and urine), blood, saliva, amniotic fluid, etc. Tissue samples can be obtained post mortem from any part of the body of an animal, but for the present purposes more usefully from living animals, for example by biopsy, by surgical removal (e.g., during surgery being conducted for other purposes), by cheek swab or by pulling a few hairs.

First Data Set: The systems and methods of the disclosure, as set forth above, involve at least two data sets, referenced herein as a "first" (or sample) and a "second" (or test) data set. These data sets are typically stored in digital form and are organized in one to a plurality of databases, which are held on user-interfaceable media such as any computer or peripheral memory or data storage device. A database can be "virtual," i.e., existing only through networking of a plurality of devices.

The first and second data sets can be parts of a single database or can be in separate databases. Either or both of the first and second data sets can, if desired, be configured in more than one database, so long as the data can be accessed for processing as discussed more fully below.

The first data set (sample data set) comprises data derived from functional gene analysis of a multiplicity of biofluid and/or tissue samples obtained from animals representing a wide range of feline genotypes and phenotypes or physiological conditions, including healthy animals (typically exhibiting a "normal" functional gene profile) and animals in a variety of disease states, e.g., mildly or severely hyperthyroid, and therefore, exhibiting an "extranormal" functional gene profile with respect to the feline NIS gene. The data are configured relationally, i.e., in such a way as to permit correlation of functional gene parameters with genotypic and phenotypic attributes. In this way, the first data set can be used to define a functional gene profile not only for healthy felines but also for those mildly and severely afflicted with hyperthyroidism, i.e., for particular subpopulations having genotype and physiological condition embraced by the data set. As the first data set increases in extensiveness, a number of beneficial outcomes can be realized: (1) the range of subpopulations, e.g. defined by the severity of the hyperthyroid condition, embraced as the data set becomes more comprehensive; (2) functional gene profile data for those particular subpopulations become more reliable; and (3) the data can be used with greater confidence to develop a predicted functional gene profile for a subpopulation not specifically represented in the data, among other advantages. In this manner, variations in the expression of the feline NIS gene as a consequence of variables other than the presence and degree of hyperthyroidism, can be identified and allowed for when defining aspects of the functional gene profile that are correlated with the presence and severity of the condition, e.g., feline hyperthyroidism.

Functional gene analysis of the gene disclosed herein in each sample, as reflected in the first data set, can include analysis with respect to one or more of DNA, RNA (for example mRNA), proteins, metabolites and biomarkers such as enzymes.

Data that can be used to develop a predicted functional gene profile for the feline NIS gene disclosed herein may come from, or be supplemented with information and data from sources other than from functional gene analysis of biofluid and/or tissue samples as described above. For example, in some embodiments, the data can come from studies published in the literature. In certain embodiments, the data can be obtained from publicly or commercially accessible data banks, for example, accessible through a website. In some embodiments the data can come from mining the genome of the species of the subject animal, and in still other embodiments, homologous functional genomic data can be obtained from species other than the subject animal, such as human, rat or mouse. In certain embodiments, data can be obtained through mining of genomes of species other than that of the subject animal.

In certain embodiment, where the method is focused on a comparatively narrow target, e.g., hyperthyroidism in felines, the data set can be established using a relatively small number of samples. Thus, the first data set, in one series of embodiments, is derived from samples collected from a multiplicity of animals representative of a range of genotypes and physiological conditions that is sufficiently broad to embrace the subpopulation of interest, e.g., felines afflicted with hyperthyroidism.

In certain embodiments, the first data set enables normal and extranormal functional gene profiles for the genes disclosed herein to be identified for animals having ranges of genotype and physiological condition that encompass the genotype and physiological condition respectively of an animal subject for which input data are submitted. With respect to physiological conditions in the present context, the word "encompass" means that animals individually and collectively having similar physiological conditions to the subject are represented in the data set, even if the subject's particular combination of physiological conditions are not found in a single animal in the data set. Similarly, the ranges of genotype and physiological condition represented in the first data set are considered herein to "encompass" the genotype and physiological condition of a subject if such genotype and physiological condition are independently found in the data set, even if not in a single animal.

Each sample from an individual animal, to be useful, must be associated with a provenance record that becomes part of the first data set. The provenance record comprises zoographical data relevant to defining the genotype and physiological condition, at the time the sample is collected, of the animal that provided the sample.

The term "zoographical data" herein refers to any and all information, whether quantitative or qualitative, that is gathered on an animal providing a biofluid or tissue sample, from sources other than analysis or experimentation on the sample itself. Sources of zoographical data can include the knowledge base of the owner, captured for example as responses to a questionnaire, veterinary records including those indicative of past and present states of wellness or disease, the animal's pedigree if it has one, biometrics (height, weight, etc.) at time of sample acquisition, etc.

Zoographical data included in the first data set can comprise one or more data items relating to genotype. Examples of such data items include without limitation: the breed of the animal, whether pedigreed, registered by a body such as the AKC or otherwise; the pedigree if known; in the case of animals of mixed breed, the breed heritage of the animal including the breed(s) of its parents and, if available, ancestors of earlier generations; sex; and coat type (e.g., long, short, wiry, curly, smooth) and coloration; evident hereditary conditions and disorders including but not limited to hyperthyroidism.

Zoographical data included in the first data set can comprise one or more data items relating to physiological condition. Examples of such data items include without limitation: age (chronological and, if determinable, physiological); weight; dimensions (e.g., height at shoulder, length of legs, length of back, etc.); veterinary medical history; reproductive history, including whether neutered, number and size of litters; present wellness or disease state and any recent changes therein, including any condition or disorder diagnosed, and any symptoms whether or not diagnosis has been made; presence of parasites, including fleas; appetite and any recent changes therein; physical activity level; mental acuity; behavioral abnormalities; and disposition (e.g., timid, aggressive, obedient, nervous). Such data may facilitate identification of variations in the expression of either the feline NIS gene that are influenced or affected by variables other than the presence and degree of hyperthyroidism, as well as the identification of phenotypic traits that may be correlated with the presence or severity of hyperthyroidism.

The "chronological age" of an animal is the actual time elapsed (e.g., in years or months) since birth. The "physiological age" of an animal is an estimate of the average chronological age of animals of similar breed exhibiting the same age-related physiological condition (mobility, mental acuity, dental wear, etc.) as the animal.

Zoographical data can further relate to aspects of the environment in which the tested animals live. Such aspects include without limitation climate, season, geographical location, and habitation. For example, it can be material to developing a food composition for an animal to know whether the animal lives in a warm or dry climate, or an arid or humid climate; whether it is currently spring, summer, autumn or winter; whether the animal is housed indoors or outdoors; whether the animal is in a home, a boarding kennel, a place of work (e.g., in the case of guard dogs, police dogs, etc.) or some other habitat; whether it is housed alone or with other animals; whether it lives in an urban or rural area; zip code, state and/or country of occupancy; whether and to what extent its habitat is affected by pollutants (e.g., tobacco smoke); and so on.

Second Data Set: The second data set (test data set) comprises data on effects of bioactive dietary components (BDCs), alone and in combinations, on functional gene expression, i.e., on functional gene expression of the genes disclosed herein. These data can include publicly or commercially available information from any source and/or results of studies conducted for the express purpose of building the second data set.

Historically, gross effects of particular bioactive dietary components on wellness have been determined by feeding studies using live animals of the species of interest, for example, dogs or cats. According to the present invention, effects of bioactive dietary components at the subcellular level, i.e., on the functional gene expression of the genes disclosed herein of cells, can be determined by controlled experiments wherein an animal model is exposed to different levels of, and/or different durations of exposure to, one or more bioactive dietary components. "Different levels" of a bioactive dietary component in the present context include a zero level of the bioactive dietary component. If multiple levels of a bioactive dietary component are included in a test, it may be possible to elucidate a dose response.

In certain embodiments, the animal model can be a live animal of the species of interest. However, an extensive data set can be more rapidly and economically assembled by use of one or more alternative testing models as exemplified below.

In one embodiment, the alternative testing model is a vertebrate model, for example a small species well adapted to functional genomic studies such as mice, rats, guinea pigs, rabbits or chickens. In another embodiment, the alternative testing model is an invertebrate model, for example an invertebrate species such as the roundworm *Caenorhabditis elegans* or the fruit fly *Drosophila melanogaster*, the genome of which has been substantially elucidated. In a further embodiment, the alternative testing model can be established is a non-animal model, particularly a genetically engineered model based on, for example yeast such as *Candida albicans*, or *Saccharomyces cerevisiea*, or a bacterium, such *Escherichia coli*. Another alternative testing model is a cell culture model, for example using primary and/or immortalized cell lines from the feline species of interest or from another species, including human. In another embodiment, the alternative testing model is an ex vivo model using tissue explants obtained from an animal and maintained outside the body of the animal.

Without being bound by theory, at the cellular level, a bioactive dietary component may act as a ligand for a protein such as a transcription factor or a receptor, may be metabolized by primary or secondary metabolic pathways, thereby altering concentrations of substrates and/or intermediates involved in gene regulation or cell signaling, or may alter signal transduction pathways and signaling by positively or negatively affecting signal pathways.

The second data set can include data not only on chemical or biological entities known as bioactive dietary components but on a variety of materials not previously known to have nutritional, nutraceutical or pharmacological effect. All such materials are considered bioactive dietary components herein if a useful effect on expression of at least one gene, function of at least one protein, or production of at least one metabolite is found for the feline NIS gene. In one embodiment, bioactive dietary components of interest herein are materials having GRAS (generally regarded as safe) or equivalent status under U.S. FDA (Food and Drug Administration) regulations or counterpart regulations in other countries, or are eligible for such status. In other embodiments a bioactive dietary component can be a therapeutically or pharmacologically effective compound, e.g., a drug or herbal medicine.

Many bioactive dietary components are chemical entities, generally naturally occurring in foods from which they can be extracted. Bioactive dietary components can, in many cases, also be prepared by microbiological (e.g., fermentation) or synthetic processes. Examples of that are chemical entities which include without limitation: amino acids; simple sugars; complex sugars; medium-chain triglycerides (MCTs); triacylglycerides (TAGs); n-3 (omega-3) fatty acids including α-linolenic acid (ALA), eicosapentaenoic acid (EPA) and docosahexaenoic acid (DHA); n-6 (omega-6) fatty acids including linoleic acid (LA), γ-linolenic acid (GLA) and arachidonic acid (ARA); choline sources such as lecithin; fat-soluble vitamins including vitamin A and precursors thereof such as carotenoids (e.g., β-carotene), vitamin D sources such as vitamin $D_2$ (ergocalciferol) and vitamin $D_3$ (cholecalciferol), vitamin E sources such as tocopherols (e.g. α-tocopherol) and tocotrienols, and vitamin K sources such as vitamin $K_1$ (phylloquinone) and vitamin $K_2$ (menadione); water-soluble vitamins including B vitamins such as riboflavin, niacin (including nicotinamide and nicotinic acid), pyridoxine, pantothenic acid, folic acid, biotin and cobalamin; and vitamin C (ascorbic acid); antioxidants, including some of the vitamins listed above, especially vitamins E and C; also bioflavonoids such as catechin, quercetin and theaflavin; quinones such as ubiquinone; carotenoids such as lycopene and lycoxanthin; resveratrol; and α-lipoic acid; L-carnitine; D-limonene; glucosamine; S-adenosylmethionine; and chitosan.

With respect to the inclusion of amino acids in the above illustrative list of bioactive dietary components, almost all foods contain protein, which typically supplies all essential amino acids. However, the protein content of a food does not necessarily supply essential amino acids in proportions that are optimal for wellness of particular animal subpopulations, thus supplementation with one or more amino acids, or with protein sources rich in such amino acids, can be desirable.

Similar considerations apply in the case of simple and complex sugars that are bioactive dietary components and may or may not be components of the carbohydrate fraction of a food, and certain fatty acids, including n-3 and n-6 fatty acids, which are bioactive dietary components and may or may not be components of the lipid fraction of a food.

Otherwise the macronutrients required in a balanced animal diet (protein, carbohydrate, fat and fiber) are considered separately from bioactive dietary components such as those listed above in designing a nutritional formula, as will be discussed below.

Certain biological materials, especially botanical materials, can be considered bioactive dietary components and can, if desired, be included in the second data set. In many of these, a bioactive chemical entity has been identified; even where a bioactive component is known other, unknown, bioactive components may be present and contribute to the bioactive effect of the biological material.

Illustrative botanicals that can be useful as bioactive dietary components include, without limitation, aloe vera, dong quai, echinacea, evening primrose, flaxseed, garlic, ginger, *ginkgo biloba*, ginseng, green tea, soy, turmeric, wheat grass and verba mate.

The second data set thus comprises data relating functional gene profile effects in an animal model to bioactive dietary components tested in the model. From this data set, by use of a suitable algorithm, a bioactive dietary component or combination of bioactive dietary components can be selected having a desired effect on functional gene profile, e.g., either or both of expression and activity of the feline NIS gene.

Input Data: The input data processed according to methods of the disclosure comprise data that define the genotype and physiological condition of the subpopulation for which a diet is to be designed, a nutritional formula prescribed or a food composition prepared. The input data can comprise zoographical data, including any of the types of zoographical data mentioned above as part of the provenance record of samples in the first data set. In certain embodiments, input data for an animal subject include functional gene profile data derived from one or more tissue and/or biofluid samples provided by the subject. According to these embodiments, the input data can indicate a functional gene profile in a normal or extranormal range.

A computer-aided system of the invention typically comprises a user interface enabling entry of the input data.

Entry of zoographical input data to the system can be made by an interface operator based on a hard-copy or electronic questionnaire filled out by an owner of an animal subject. Alternatively, entry of such data can be effected at an interface directly by the owner.

The user interface for entry of zoographical data can be remote from a main processor (where the input data are processed according to a method of the invention) but linked thereto via a network such as the internet. Alternatively the user interface can be local (e.g., hard-wired) to a main processor, for example at a retail store or veterinarian's office. In various embodiments the user interface can, illustratively and without limitation, comprise a keyboard and monitor; a personal computer, for example in the owner's home; a touch-screen terminal; a touch-tone telephone; or a voice-activated system. Alternatively, the zoographical data can be pre-entered into a computer-readable medium such as printed barcodes or computer-readable alphanumeric characters; floppy disk; CD-ROM; memory card; chip; etc., and scanned or uploaded at a terminal equipped to read from such a medium. The medium can, in some embodiments, be attachable to the subject animal, for example on a collar, ear-tag or collar-attached dog-tag, or, in the case of certain types of chip, surgically implanted under the animal's skin. As yet another option, the zoographical data can be pre-entered into the computer-aided system itself and stored in a database, whence it can be retrieved by entry of a code unique to the subject animal for which the zoographical data are originally entered. Such a code can be entered via any interface type and on any suitable medium, including those indicated above.

Processing Input Data to Derive a Nutritional Formula: Processing of the input data for a subpopulation (which can, as stated above, be a single animal subject, e.g., feline afflicted with hyperthyroidism), is accomplished by means of an algorithm, herein sometimes referred to as a "first" algorithm, that draws on the first and/or second data sets described above to derive from the input data a nutritional formula that promotes wellness of one or more animals of the subpopulation.

The algorithm, at least for embodiments of the invention wherein the algorithm draws on both a first and a second data set as described above, can illustratively be embodied in a computer program that incorporates at least the following tasks. Processing does not necessarily occur in the sequence presented below. A computer-aided system of the invention can optionally employ parallel processing, wherein two or more tasks are handled simultaneously.

In one task, input data from a subject are read into memory. In another, a search is conducted of the first data set for zoographical and/or functional gene profile data that corresponds as closely as possible to the input data. Searching and statistical techniques known in the art can be used to establish one to a plurality of "hits" that collectively provide a best fit to the genotype and physiological condition of the subject. Where a functional gene profile is provided as part of the input data for the subject, the algorithm again identifies any departure from a normal state. In a further task, a search is conducted of the second data set for test data pertaining to a functional gene profile as established above for the subject. Test data indicating a bioactive dietary component or combination of bioactive dietary components that are effective to maintain such a functional gene profile in a normal state, or shift such a functional gene profile from an extranormal state towards greater normality, are retrieved, for example using searching and statistical techniques known in the art to provide a best fit to the a functional gene profile of the subject. In another task, a nutritional formula is computed incorporating effective amounts of one or more bioactive dietary components identified as described above. The nutritional formula can be computed in the form of a complete diet, incorporating basic energy, protein and fiber requirements (which can be readily established from the input zoographical data) together with the identified bioactive dietary components. Alternatively, the nutritional formula can be computed in the form of a dietary supplement, excluding basic energy, protein and fiber requirements.

Optionally, the nutritional formula can be output via a user interface such as a computer video screen, printer, voice synthesizer, etc. A code representing the nutritional formula can be downloaded to a user-readable or computer-readable medium, for example a printed barcode, a printed numerical code, the data strip of a card, a memory device, a disk, a chip, etc. In one embodiment such a code is downloaded to a chip adapted for implantation in an animal, particularly a companion animal.

In embodiments where the nutritional formula is further processed, for example, to generate a food composition, no output of the nutritional formula itself may be required.

In certain embodiments, a food composition is formulated directly by amalgamating the first algorithm with a second (formulation) algorithm as described below. According to such embodiments, computation of a nutritional formula as an intermediate step may or may not occur.

Where a nutritional formula is output, bioactive dietary components and other components can be expressed in any suitable form. For example, components can be expressed in terms of their content in a food composition (e.g., in % or in mg/g, usually on a dry matter basis), in terms of a daily dosage or allowance (e.g., in g/day), optionally on a live weight basis (e.g., in mg/kg/day).

Overview of an Illustrative Method of the Invention: FIG. 3 is a flow chart showing an illustrative method for designing a nutritional formula. According to this illustrative method, a key step is the processing of input data, shown as a diamond in FIG. 3, to generate the nutritional formula, for example as described immediately above. Three subsystems feed into the processing step.

In a first subsystem, starting at the top left of FIG. 3, animals in various states of wellness and disease are identified, i.e., healthy felines and those afflicted with either mild or severe hyperthyroidism. As suggested above, it is often desirable that this set of animals be as large as possible, and includes as broad as possible a range of states of disease and physiological disorder as well as a broad range of genotypes. A set of zoographical data is collected for each animal. Each animal is a source of one to a plurality of tissue and/or biofluid samples. Each sample is subjected to functional gene analysis (including one or more of gene expression, proteomic and metabolomic analysis), for example, using an established microarray technique, to establish a functional gene profile for the animal that provided the sample, reflecting the genotype and physiological condition of the animal at the time the sample was collected, with respect to the feline genes disclosed herein, viz, the feline NIS gene. Data defining the functional gene profile become part of the first data set as defined herein, in association with the zoographical data relating to the animal.

In a second subsystem, starting at the top right of FIG. 3, bioactive dietary components are tested in one or more animal models as described above. The more bioactive dietary components that are tested, the better; and the more dosages of each bioactive dietary component tested, the better. Testing can include combinations of bioactive dietary components as well as individual bioactive dietary components. From all this testing, bioactive dietary components effects on functional gene expression of the animal model can be established. The test results go to make up the second data set as defined herein.

The first and second data sets are typically organized in one or more relational databases that are adapted for search and retrieval of information by the first algorithm as it processes input data.

In a third subsystem, in the lower left portion of FIG. 3, input data are entered for an animal subject or subpopulation. As indicated above, the input data typically include zoographical data and may or may not include functional gene profile data. Processing the input data to generate a nutritional formula requires the processing algorithm to access the first and second data sets as shown in FIG. 3. The nutritional formula generated is one that the data stored in the system shows or suggests will promote wellness of the subject animal or one or more animals of the subpopulation, e.g., will be useful for treatment of felines afflicted with hyperthyroidism. Some aspects of "promoting wellness" are described in more detail herein. Optionally (not shown in FIG. 3), input data that comprise both zoographical and functional gene profile data are added to the first data set, and can be accessible in future iterations of the method.

In one embodiment, such input data are associated with an identifier or code for the specific animal to which they relate. If the same animal is the subject of a subsequent iteration of the method, the data processing algorithm can be programmed to retrieve prior functional gene profile data for that animal. In this way, trends and changes in functional gene profile of the animal can be tracked. Among other benefits, such tracking can enable periodic monitoring of the effectiveness of the nutritional formula in maintaining a normal functional gene profile, in shifting an extranormal functional gene profile towards greater normality, and/or in any aspect of the promotion of wellness as more fully described herein.

Iterative use of the method for a specific animal can form a basis for a nutritional plan that is monitored throughout all or a substantial part of the life of the animal. Corrective action can be taken by adjusting the nutritional formula whenever the animal's state of wellness declines or its functional gene profile moves into an extranormal state, indicative of, e.g., progression of the hyperthyroid condition.

Preparing a Food Composition: The end-product of one embodiment of the invention is the nutritional formula derived as set forth above. For example, a veterinary physician or dietician can prescribe a nutritional formula for a subject animal by a method as herein described. A nutritional formula can be designed to provide a total solution to a state of disease or physiological disorder, or it can be adapted for use in conjunction with pharmaceutical (e.g., administration of a drug or other medication), as described below, or surgical intervention.

In another embodiment, the nutritional formula is used as the basis for preparing a food composition, which becomes the end-product of this embodiment. A second or formulating algorithm can be used to derive a food composition from the nutritional formula. As mentioned above, such an algorithm can be integrated with the first algorithm to generate a food composition directly by processing the input data. Disclosure herein of a nutritional formula as an intermediate stage in generating a food composition does not limit the present invention to methods and systems wherein such a stage is identifiable.

Algorithms for formulating food compositions based on a nutritional formula are well known in the art. Such algorithms access a data set having analysis of various food ingredients and draw on that data set to compute the amounts of such ingredients in a food composition having the desired nutritional formula.

Optionally the data set on which the second algorithm draws further includes cost data for the various food ingredients, and the second algorithm incorporates a routine to include cost as a criterion in selection of ingredients. This can enable a food composition to be prepared at reduced cost, for example at lowest cost consistent with providing the desired nutritional formula.

Other criteria can be built in if desired. For example, ingredients can be identified as "organic" or otherwise, so that if an "organic" food product is desired only "organic" ingredients are selected.

In one embodiment, the food composition can be selected, from a range of pre-existing options, e.g., an existing pet food product line, to best fit or match the nutritional formula derived by practice of the invention. For example, an algorithm can be used that compares a computed food composition or nutritional formula with those of available products, and selects the product coming closest to matching that composition or formula.

In another embodiment, a pet food is manufactured according to the composition derived as set forth above. Such a pet food is accordingly customized to an individual animal providing the input data, or to an animal subpopulation represented by an animal providing the input data. Such manufacture can be offline, i.e., not controlled by a computer-aided system. Alternatively, such manufacture can be in part or in whole under the control of, and/or driven by, an extension of the computer-aided system that generates the nutritional formula and computes a composition for the food as described above.

The product thus manufactured can be a complete food or a supplement adapted for addition to or mixing with a base food to form a complete food. The product can be liquid, semi-solid or solid; if solid, it can be moist (e.g., a retortable moist pet food), semi-moist or dry (e.g., a kibble). A supplement can be designed for use, for example, as a gravy to accompany a base food, or as a coating for a base kibble.

Suitable computer-controlled apparatus for manufacturing a food product having a defined composition is known in the art.

Optionally, the food, once prepared according to a method of the invention, is packaged in a suitable container. For example, a moist food can be packaged in a can, a jar or a sealed pouch; a dry food can be packaged in a bag, a box, or a bag in a box. This step can, if desired, also be under control of a computer-aided system.

A computer-aided system of the invention can be further harnessed to print a label or package insert for the food product, having any or all information required by governmental regulations and by customary commercial practice. For example, the label or package insert can include a list of ingredients and/or a guaranteed analysis.

Food manufacture, including packaging and labeling, can occur at a conventional manufacturing site such as a factory. Alternatively, it can be convenient to arrange for manufacture of the food to take place more locally to the end-user, for example at a point of sale at a distributor's or retailer's premises, such as a pet food store. In one embodiment the food composition is prepared at a distribution site and delivered to the end-user, for example in response to an order placed by the end-user, such as by telephone or via a website accessed through the internet.

The food composition is, in one embodiment, prepared by a compounder on receipt of a prescription from a veterinary physician or dietician setting forth the nutritional formula derived by the first algorithm.

In another embodiment, an end-user at a point of sale terminal enters a code representing a nutritional formula previously selected for a specific animal, for example by swiping a card or scanning a chip containing such a code. A computer-aided mixing apparatus, for example a mixing and vending apparatus located at the point of sale, then prepares a food composition based on the nutritional formula thus encoded, and delivers it to the end-user.

A food composition prepared by a method of any embodiment of the present invention is itself a further embodiment of the invention.

In one embodiment, a method of the invention is repeated at intervals for one or more individual animals of a subpopulation, the nutritional formula being adjusted as needed for changes in physiological condition or functional gene profile over time. Such changes can be brought about at least in part by the nutritional formula (s) of food composition(s) prepared by previous iteration(s) of the method. An iterative method can provide a feeding plan, for example to transition from remediation of a wellness problem to prevention of recurrence of the problem.

Data Bank: The term "data bank" herein refers to a physical embodiment of a collection of data comprising one to a plurality of data sets that can be configured in one to a plurality of databases. A data bank thus comprises a medium wherein or whereon such data are stored. A data bank can comprise more than one such medium; however, in such a case the media are functionally linked. Media useful herein can be user-readable, as in the case of a printed spreadsheet, but typically, and especially in view of the large volume of data presently contemplated, such media are computer-readable.

A data bank of the invention can comprise one to a plurality of media residing on or linked electronically to a computer, the media having stored therein or thereon data relating functional genomic profile of an animal species or model to at least one of (a) genotype and/or physiological condition of an animal providing one or more tissue and/or biofluid samples from which said functional genomic profile is determined; and (b) exposure of the animal species or model to one or more bioactive dietary components. The data are configured as one to a plurality of databases. On submission of a query relating to functional genomic profile and/or bioactive dietary components via the computer, information in pertinent response to the query is retrievable from the one or more databases.

According to one embodiment, such a query requests output of functional genomic profile data relevant to input data on genotype and/or physiological condition of an animal subject. According to another embodiment, such a query requests output of bioactive dietary component data relevant to input data on functional genomic profile of an animal subject. The information retrievable in pertinent response to such a query can be expressible as a nutritional formula for the animal subject.

In a typical data bank of the invention, the data comprise a first data set relating functional genomic profile to genotype and/or physiological condition of an animal providing one or more tissue and/or biofluid samples from which said functional genomic profile is determined; and a second data set relating functional genomic profile to exposure of an animal model to one or more bioactive dietary components. According to this embodiment, information is retrievable in pertinent response to a query requesting output of a nutritional formula for an animal subject appropriate to input data on genotype and/or physiological condition of the subject.

The data in such a data bank optionally further comprises a third data set comprising content of bioactive dietary components in ingredients for a food composition. According to this embodiment, information is retrievable in pertinent response to a query requesting output of a food composition for an animal subject appropriate to input data on genotype and/or physiological condition of the subject.

According to a related embodiment, the third data set further comprises cost of ingredients, and information is retrievable is retrievable in pertinent response to a query requesting output of a cost-optimized food composition for an animal subject appropriate to input data on genotype and/or physiological condition of the subject.

In a data bank of a further embodiment, information is retrievable in pertinent response to a query requesting output relating input data on functional genomic profile of an animal subject to a normal functional genomic profile.

In a data bank of a still further embodiment, information is retrievable in pertinent response to a query requesting output of a nutritional formula for an animal subject effective (a) to maintain a normal functional genomic profile or (b) to modify an extranormal functional genomic profile to a more normal state.

Further embodiments of the invention are those listed below. One such embodiment is a method of selecting a food composition for an animal subject, preferably a companion animal subject. The method comprises (a) accessing a database populated with normal and extranormal functional genomic data; (b) by reference to said data, evaluating the functional gene profile of the subject relative to a normal profile; (c) from a database populated with test results on functional gene profile in an animal model exposed to at least one bioactive dietary component, identifying one or more bioactive dietary components tending to shift functional gene profile to a more normal state; and (d) selecting a food composition comprising said one or more bioactive dietary components.

In one aspect of the invention, the food composition is selected with reference to a database populated with data on costs of food ingredients and bioactive dietary components. In another, the food composition is effective to shift functional gene profile to a more normal state and is formulated at or below a target cost. In another, the databases are stored on one or more media. In another, a computer capable of accessing the one or more media is used to evaluate functional genomic data. In a further aspect, the method further comprises feeding the composition to the animal subject to prevent development of a disease state in the subject, to enhance the subject's health, to shift the subject's functional gene profile from an extranormal to a normal state, or to effect a change in the subject's functional gene profile. In another, the normal and extranormal functional genomic data are derived from analysis of tissues and/or biofluids of a population of animals in states of wellness and disease.

Such a population can be defined at least in part by phenotypic parameters, including the severity of hyperthyroidism.

Another embodiment is a method of formulating a food composition for an animal subject. The method comprises (a) accessing a first data set containing data that relate the subject's functional gene profile for either the feline NIS gene as determined from one or more tissue and/or biofluid samples to a normal functional gene profile; (b) accessing a second data set containing information on effects of individual bioactive dietary components and/or combinations thereof on a functional gene profile in one or more model test systems; and (c) computing a formulation comprising a bioactive dietary component or combination thereof effective when used as a food composition to reverse or attenuate displacement of the subject's functional gene profile from the normal functional gene profile.

In one embodiment, the formulation is effective to promote a transition of the subject's functional gene profile to a normal functional gene profile. In another, the method further comprises accessing a data set containing information relating to the subject's phenotype. Such information can, for example, be selected from the group consisting of age, coat type, size and weight. In a further aspect, the method further comprises accessing a data set containing information on source and cost of an active form, precursor or metabolite of each bioactive dietary component in the formulation. In another, the formulation computed by such a method is cost efficient. In another, the normal functional gene profile is established from analysis of tissues and/or biofluids from a population of animals. Such a population can again be defined at least in part by genotypic parameters, at least in part by phenotypic parameters. In a further aspect, at least one of the data sets is stored on one or more media. In another, a computer capable of accessing the one or more media is used to compute the formulation.

Design of Animal Food Compositions for Hyperthyroid Cats

In one embodiment, the present disclosure describes a method of designing an animal food composition. One aspect of this embodiment involves selection of a target disease or condition of a companion animal and identification of proteins and polypeptides involved in or underlying that disease or condition, including but not limited to, the feline NIS gene. This is followed by a determination of whether an increase or decrease in expression or activity one or more of those proteins and polypeptides would be expected to ameliorate, modulate, or eliminate the target disease or condition. By screening components (macronutrients) of pet food compositions as described herein, it has been possible to identify bioactive dietary components that can be fed to a companion animal for treatment of the target disease or condition, e.g., by effectively decreasing expression or activity of the feline NIS gene.

Accordingly, in one embodiment, the present disclosure provides a method for design of a food composition suitable for treating a disease or condition in an animal, which method comprises: (a) identifying a target disease or condition, (b) identifying a polypeptide involved in the etiology underlying that disease, e.g., the feline NIS gene, (c) determining whether an increase or a decrease in activity or expression of said identified polypeptide would ameliorate the target disease or condition, (d) performing at least one multivariate analysis to identify bioactive dietary components capable of modulating activity or expression of said identified polypeptide in a manner required to ameliorate the target disease or condition, and (e) formulating a food composition comprising the bioactive dietary component. In the present context, for example, hyperthyroidism can be associated with substantial increases in the level of expression of the feline NIS gene The present disclosure provides methods and reagents for identification of dietary ingredients that reduce iodine uptake by the thyroid gland and that inhibit synthesis of thyroid hormone. The methods disclosed herein involve the use of an isolated gene fragment, which encodes a portion of the feline sodium/iodine symporter protein (NIS protein), to develop gene expression profile data in the presence and absence of test materials. Using those methods, it has been possible to identify materials that can be included in the diet of a feline afflicted with hyperthyroidism in order to treat that condition.

The present disclosure also provides a method for design of a pet food composition suitable for administration to a feline companion animal afflicted with hyperthyroidism, the method comprising: (a) accessing at least one first database that comprises a first data set relating a functional gene profile of a biofluid or tissue sample from an animal to physiological condition and optionally genotype of the animal, wherein the functional gene profile is that of the feline NIS gene, (b) accessing at least one second database that comprises a second data set relating effects of bioactive dietary components on the functional gene profile of step (a); (c) using a first algorithm drawing on the first and second data sets, processing input data defining physiological condition and optionally genotype of the subpopulation, e.g., felines afflicted with hyperthyroidism, to derive a nutritional formula useful for selecting and preparing a food composition for that animal subpopulation; and (d) preparing a food composition based on the nutritional formula; wherein that food composition is suitable for administration to a feline companion animal afflicted with hyperthyroidism.

The present invention also relates to compositions and methods for diagnosing hyperthyroidism in felines as well as methods for identifying materials and formulating food compositions containing those materials that will be useful for treatment of hyperthyroidism in felines.

In certain aspects of this embodiment, the first data set is derived from samples collected from a multiplicity of individual animals representative of a range of genotypes and physiological conditions that includes feline companion animals afflicted with hyperthyroidism. In one aspect, each such sample from an individual animal is associated with a provenance record that comprises zoographical data relevant to defining the genotype and physiological condition, at the time the sample is collected, of the individual animal. In another aspect of this embodiment, the zoographical data comprise one or more data items relating to genotype, selected from the group consisting of breed, breed(s) of parents, pedigree, sex, coat type, and evident hereditary conditions and disorders, particularly hyperthyroidism. In another aspect of this embodiment, the zoographical data comprise one or more data items relating to physiological condition, selected from the group consisting of age, weight, veterinary medical history, reproductive history, present wellness or disease state, appetite, physical activity level, mental acuity, behavioral abnormalities and disposition, and, in particular, the presence and degree of affliction with hyperthyroidism.

In a specific aspect of this method, the first data set comprises data relating to analysis of the sample with respect to one or more components selected from the group consisting of DNA, RNA, proteins, metabolites and biomarkers, while the second data set is derived from controlled experiments comprising exposing an animal model to different levels of one or more bioactive dietary components.

In another specific aspect of this method, the input data comprises zoographical data relevant to defining the genotype and physiological condition of feline companion animals afflicted with hyperthyroidism. In still another aspect of this method, the input data comprises analytical data from a biofluid or tissue sample obtained from feline companion animals not afflicted with hyperthyroidism. In other specific aspects of this method, the input data comprises analytical data from a biofluid or tissue sample obtained from feline companion animals afflicted with mild hyperthyroidism as well as from feline companion animals afflicted with severe hyperthyroidism.

The present disclosure is also directed to food compositions prepared by the above method for design of a pet food composition, illustrative examples of which are described hereinbelow, which are useful for administration to feline companion animals afflicted with hyperthyroidism.

Accordingly, provided herein are methods for design of a food composition for an animal afflicted with a disease or condition, comprising identification of bioactive dietary components useful in ameliorating the effects of a disease or condition with which the animal is afflicted. In a particular, illustrative aspect of this embodiment, the disease or condition is hyperthyroidism and the afflicted animal is a feline companion animal.

In one embodiment, the present disclosure provides a method of treatment of hyperthyroidism in a companion animal. In one aspect, this disclosure provides a method for treatment of hyperthyroidism in a feline companion animal.

In another embodiment, the present disclosure provides compositions useful in a method of treatment of hyperthyroidism in a companion animal. In one aspect, this disclosure provides compositions useful in a method for treatment of hyperthyroidism in a feline companion animal.

In particular aspects of these embodiments, the hyperthyroid companion animal that is in need of treatment is fed a pet food composition that comprises an effective amount of a bioactive dietary component, that is sufficient to suppress expression or activity of at least one polypeptide required for biosynthesis, transport, or activity of either of both of thyroxine and triiodothyronine, such as, but not limited to, the activity of the feline NIS gene described herein.

In certain embodiments, the polypeptide inhibited by the bioactive dietary components is selected from the group consisting of thyroid peroxidase, sodium/iodide symporter (NIS), thyroid oxidase, intrathyroidal type I 5'-deiodinase, thyroid stimulating hormone receptor, pendrin, monocarboxylate transporter 8, and combinations thereof.

Also provided is a method for design of a food composition suitable for treating a disease or condition in an animal.

Probes

The probes useful in the practice of the invention and which are utilized in the identification of the feline biomarkers in the feline samples comprise 10 to 50, 15 to 40, 20 to 30 consecutive nucleotides of SEQ ID NO:1 or its complement. In particular embodiments, the probe comprises about 25 nucleotides consecutive nucleotides of SEQ ID NO:1 or its complement. The probe sequences correspond to the probe identification number used in the proprietary feline gene chip manufactured by Affymetrix, identified as Affymetrix Feline GeneChip®, as more fully described in this specification. HP06947_at corresponds to SEQ ID NO. 1, which is useful in hybridizing to the feline NIS gene mRNA sequence.

Biomarkers

A biomarker useful in the practice of the present invention is the feline NIS gene fragment of SEQ ID NO:1 and the encoded peptide thereof of SEQ ID NO:2, as more fully described below and in the sequence listings appended to this specification.

In a certain embodiments of the present invention, the feline may have normal thyroid function, as defined by art-recognized clinical measurements, and the methods of the invention may be used to predict, detect and diagnose in such feline a change from a normal state to an abnormal state leading to a hyperthyroid condition.

In another embodiment, the method of the invention can be practiced by using an array that detects gene expression changes, e.g., changes in the level of expression of the NIS gene. In one method, such array is a DNA microarray. The level of activity or expression may be determined by measuring the expression product of that gene which may be a polynucleotide or a polypeptide or protein.

In another embodiment, the method of the invention can be practiced by using an array that detects gene expression changes, or the level of activity of one or more genes, or their expression products, selected from the group consisting of: sodium/iodide transporter (NIS), thyroid peroxidase (TPO), thyroid stimulating hormone receptor (TSHR), iodide transporter (IT; Pendrin), thyroid oxidase (ThOX), $T_4$ thyroxine deiodinase (e.g., intrathyroidal type I 5'-deiodinase), monocarboxylate transporter (e.g., monocarboxylate transporter-8), and a thyroid hormone receptor activator molecule. In one aspect of this method, such array is a DNA microarray. The level of activity or expression of one or more genes may be determined by measuring the expression product of such genes which may be a polynucleotide or a polypeptide or protein.

In one aspect, the invention includes contacting a tissue sample or bodily fluid specimen with an agent that detects in a feline one or more genes or the expression product of such one or more genes selected from the group consisting of: sodium/iodide transporter (NIS), thyroid peroxidase (TPO), thyroid stimulating hormone receptor (TSHR), iodide transporter (IT; Pendrin), thyroid oxidase (ThOX), $T_4$ thyroxine deiodinase (e.g., intrathyroidal type I 5'-deiodinase), monocarboxylate transporter (e.g., monocarboxylate transporter-8), and a thyroid hormone receptor activator molecule. The agent can be an antibody or a nucleic acid probe used in conjunction with conventional assay means such as immobilization on a solid phase, microtiter wells, tubes, dipsticks or other conventional means.

In another aspect, the invention includes contacting a tissue sample or bodily fluid specimen with an agent that detects in a feline one or more genes or the expression product of such one or more genes selected from the group consisting of: sodium/iodide transporter (NIS), thyroid peroxidase (TPO), thyroid stimulating hormone receptor (TSHR), iodide transporter (IT; Pendrin), thyroid oxidase (ThOX), $T_4$ thyroxine deiodinase (e.g., intrathyroidal type I 5'-deiodinase), monocarboxylate transporter (e.g., monocarboxylate transporter-8), and a thyroid hormone receptor activator molecule. The agent can be an antibody or a nucleic acid probe used in conjunction with conventional assay means such as immobilization on a solid phase, microtiter wells, tubes, dipsticks or other conventional means.

Another embodiment of the method of the invention encompasses use of conventional assay means to determine gene expression in a feline either alone or in conjunction with gene expression array displays employing polypeptides and/or polynucleotides, such conventional assay means comprising one or more of ELISA, RIA, immunoblot assays, in situ hybridization, Northern blot analysis, Western blot analysis and Luminex X-Map® analysis.

In a further aspect, the invention relates to compositions comprising one or more nucleic acid probes that specifically hybridize to a nucleic acid, or fragment thereof, encoding a biomarker of the present invention, e.g., SEQ ID NO:1. In a specific aspect of this embodiment, the nucleic acid probe specifically hybridizes to a coding sequence (or the complement thereof) of SEQ ID NO:1, i.e., encodes a peptide sequence encompassed by that of SEQ ID NO:2. In another aspect of this embodiment, the disclosure provides compositions comprising one or more of such nucleic acid probes that specifically hybridize to a nucleic acid, or fragment thereof, encoding the NIS protein, or a portion thereof.

In an additional aspect, the present disclosure provides compositions comprising antibodies that specifically bind to a polypeptide encoded by a gene expressing a biomarker of the present invention. In particular, the present disclosure provides compositions comprising antibodies that selectively bind the feline NIS protein as compared to, e.g., the human or canine homologs thereof. In another aspect, the present disclosure provides compositions comprising antibodies that selectively bind the peptide sequence of SEQ ID NO:2, as compared, e.g., to the human or canine homologs thereof.

It is further contemplated herein that the methods of the present invention may be used in combination with traditional diagnostic techniques that are able to detect the physical and morphological characteristics of hyperthyroidism.

A further aspect of the disclosure is a method for diagnosis and/or prognosis of hyperthyroidism in a feline, wherein the method comprises the steps of: obtaining at least one tissue sample or bodily fluid specimen from the animal; determining the amount of one or more biomarkers, e.g., that of the NIS gene, in said at least one sample or specimen obtained from the animal, wherein said biomarker is a polypeptide, protein, RNA, DNA, polynucleotide or metabolite thereof.

Other and further objects, features, and advantages of the present invention will be readily apparent to those skilled in the art.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248, 6,309,822 and 6,344,316. Genotyping and uses therefore are shown in U.S. Ser. No. 60/319,253, Ser. No. 10/013,598, and U.S. Pat. Nos. 5,856,092, 6,300,063, 5,858, 659, 6,284,460, 6,361,947, 6,368,799 and 6,333,179. Other uses are embodied in U.S. Pat. Nos. 5,871,928, 5,902,723, 6,045,996, 5,541,061, and 6,197,506.

Those skilled in the art will recognize that the products and methods embodied in the present invention may be applied to a variety of systems, including commercially available gene expression monitoring systems involving nucleic acid probe arrays, membrane blots, microwells, beads and sample tubes, constructed with various materials using various methods known in the art. Accordingly, the present invention is not limited to any particular embodiment, and the following description of specific embodiments of the present invention is for illustrative purposes only.

The gene expression monitoring system, in a preferred embodiment, may comprise a nucleic acid probe array (including an oligonucleotide array, a cDNA array, a spotted array, and the like), membrane blot (such as used in hybridization analysis such as Northern, Southern, dot, and the like), or microwells, sample tubes, beads or fibers (or any solid support comprising bound nucleic acids). The gene expression monitoring system may also comprise nucleic acid probes in solution.

The present invention also contemplates sample preparation involving amplification. A genomic sample may be amplified by a variety of mechanisms, some of which may employ PCR. The sample may be amplified on the array. See, for example, U.S. Pat. No. 6,300,070 and U.S. patent application Ser. No. 09/513,300.

Other suitable amplification methods include the ligase chain reaction (LCR) (e.g., Wu and Wallace, Genomics 4, 560 (1989), Landegren et al., Science 241, 1077 (1988) and Barringer et al. Gene 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517 and 6,063,603, each of which is incorporated herein by reference). Other amplification methods that may be used are described in, U.S. Pat. Nos. 5,242,794, 5,494,810, 4,988, 617, 6,344,316 and in U.S. Ser. No. 09/854,317, each of which is incorporated herein by reference.

Additional methods of sample preparation and techniques are described in Dong et al., *Genome Research* 11, 1418 (2001), in U.S. Pat. Nos. 6,361,947, 6,391,592 and U.S. patent application Ser. Nos. 09/916,135, 09/920,491, 09/910,292 and 10/013,598.

The gene expression monitoring system according to the present invention may be used to facilitate a comparative analysis of expression in different cells or tissues, different subpopulations of the same cells or tissues, different physiological states of the same cells or tissue, different developmental stages of the same cells or tissue, or different cell populations of the same tissue. In a preferred embodiment, the proportional amplification methods of the present invention can provide reproducible results (i.e., within statistically significant margins of error or degrees of confidence) sufficient to facilitate the measurement of quantitative as well as qualitative differences in the tested samples.

Polynucleotide hybridization assays are well known in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y, 1989);

Berger and Kimmel Methods in Enzymology, Vol. 152, Guide to Molecular Cloning Techniques (Academic Press, Inc., San Diego, Calif., 1987); Young and Davis, P.N.A.S. 80: 1194 (1983). Methods and apparatus for carrying out repeated and controlled hybridization reactions have been described in U.S. Pat. Nos. 5,871,928, 5,874,219, 6,045,996, 6,386,749 and 6,391,623 each of which are incorporated herein by reference. Signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803 and 6,225,625, in U.S. Patent application 60/364,731 and in PCT Application PCT/US99/06097 (published as WO99/47964), each of which also is hereby incorporated by reference in its entirety for all purposes. Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Design of Animal Food Compositions

Provided herein are methods for design of a food composition for an animal afflicted with a disease or condition, comprising identification of bioactive dietary components useful in ameliorating the effects of a disease or condition with which the animal is afflicted. In a particular, illustrative aspect of this embodiment, the disease or condition is hyperthyroidism and the afflicted animal is a feline companion animal. The methods described herein and as set forth in the Examples provide methods and materials for identifying bioactive dietary components. Also described herein are illustrative pet food compositions comprising those bioactive dietary components, which compositions can be administered to felines afflicted with hyperthyroidism to treat that disease.

Therapeutic Pet Food Compositions for Hyperthyroid Cats

In one illustrative embodiment of a food composition for afflicted animals, feline companion animals diagnosed as hyperthyroid are identified and basal levels of T4. In addition, thyroid biopsies of each are taken and basal expression levels are determined for each of sodium/iodide transporter (NIS), thyroid peroxidase (TPO), thyroid stimulating hormone receptor (TSHR), iodide transporter (IT; Pendrin), thyroid oxidase (ThOX), $T_4$ thyroxine deiodinase (e.g., intrathyroidal type I 5'-deiodinase), monocarboxylate transporter (e.g., monocarboxylate transporter-8), and a thyroid hormone receptor activator molecule. A series of food compositions are formulated and fed to each of the animals for an appropriate period of time and blood samples taken for determination of thyroid stimulating hormone (TSH) levels. Food compositions are prepared and data are reviewed using principal component analysis, i.e., a form of multivariate analysis, to identify food macronutrients that are correlated with an increase in thyroid stimulating hormone (TSH), indicative of a decrease in circulating $T_4$ thyroxine and $T_3$ triiodothyronine levels. Treated animals displaying a substantial increase in thyroid stimulating hormone (TSH) levels are biopsied and expression levels are determined for each of sodium/iodide transporter (NIS), thyroid peroxidase (TPO), thyroid stimulating hormone receptor (TSHR), iodide transporter (IT; Pendrin), thyroid oxidase (ThOX), $T_4$ thyroxine deiodinase (e.g., intrathyroidal type I 5'-deiodinase), monocarboxylate transporter (e.g., monocarboxylate transporter-8), and a thyroid hormone receptor activator molecule. Pet food components (macronutrients) correlated with a decrease in expression of one or more of TSH, TPO, TSHR, IT/Pendrin, ThOX, $T_4$ thyroxine deiodinase (e.g., intrathyroidal type I 5'-deiodinase), monocarboxylate transporter (e.g., monocarboxylate transporter-8), are referred to herein as bioactive dietary components.

Each of a vegetable blend, millet, and tomato pomace are identified as comprising bioactive dietary components that lead to decreased expression of the sodium/iodide transporter (NIS). That is, in another aspect of this embodiment, bioactive dietary components as above, are refined or fractionated to identify one or more molecules or sub-components with an increased specific activity with respect to modulation of the activity of a target molecule. In still another aspect, whole-animal testing can be supplemented, augmented, or possibly replaced using in vitro tissue culture systems employing appropriate cell lines. Such cell lines or indicator systems, for example, may have been genetically-engineered to provide easily-measured signals upon inhibition or stimulation of the expression levels or activity of one or more genes and their encoded proteins. In a particular aspect, the bioactive dietary component is extracted and/or fractionated to provide a preparation that is tested for its ability to alter gene expression, e.g., alter feline NIS gene expression in tissue culture cells.

In certain embodiments, a hyperthyroid companion animal is administered a food composition comprising an effective amount of a first biologically effective nutrient sufficient to suppress expression or activity of a first polypeptide required for biosynthesis, transport, or activity of either or both of thyroxine and triiodothyronine. In another aspect of this embodiment, the food composition further comprises an effective amount of a second biologically effective nutrient sufficient to suppress expression or activity of a second polypeptide required for biosynthesis, transport, or activity of either or both of thyroxine and triiodothyronine. In additional aspects of these embodiments, the food composition comprises limiting amounts of either or both of iodide and selenium salts. In a still further aspect, the afflicted companion animal is also administered an antithyroid agent, which, e.g., may be selected from among methimazole, propylthiouracil, carbimazole, and combinations thereof.

In some embodiments, therefore, the food compositions of the invention comprise from about 0.1 to less than about 1 mg/kg iodine on a dry matter basis. In some such embodiments, the food compositions comprise from about 0.1 to about 0.5 mg/kg iodine on a dry matter basis. In other such embodiments, the food compositions of the invention comprise from about 0.1 to about 0.3 mg/kg iodine on a dry matter basis. In yet other such embodiments, the food compositions of the invention comprise from about 0.15 to about 0.25 mg/kg iodine on a dry matter basis. And in further such embodiments, the food compositions of the invention comprise from, about 0.1 to about 0.2 mg/kg iodine on a dry matter basis. As discussed above, iodine is a constituent of $T_3$ and $T_4$. Iodine as used herein refers to the iodine atom without reference to its molecular or ionic form, and includes iodine present in one or more chemical forms such as, for example, iodide, iodate, and periodate.

In still other embodiments, the food compositions of the invention comprises from about 0.1 to less than about 1 mg/kg selenium on a dry matter basis. In some such embodiments, the food compositions comprise from about 0.1 to about 0.8 mg/kg selenium on a dry matter basis. In other such embodiments, the food compositions comprise from about 0.15 to about 0.65 mg/kg selenium on a dry matter basis. In yet other such embodiments, the food compositions comprise from about 0.4 to about 0.7 mg/kg selenium on a dry matter basis. In further such embodiments, the food compositions comprise from about 0.3 to about 0.65 mg/kg selenium on a dry matter basis. As noted above, selenium has a role in maintaining normal thyroid and iodine metabolism, particularly through the control of the deiodinase enzymes that regulate the conversion of $T_4$ to $T_3$. Selenium as used herein refers to the selenium atom without reference to its molecular or ionic form, and includes selenium present in one or more chemical forms such as, for example, selenide, selenite, and selenate.

In still further embodiments, the food compositions of the invention comprise from about 0.1 to less than about 1 mg/kg iodine on a dry matter basis and from about 0.1 to less than about 1 mg/kg selenium on a dry matter basis. In some such embodiments, the food compositions comprise from about 0.1 to about 0.5 mg/kg iodine on a dry matter basis and from about 0.1 to about 0.8 mg/kg selenium on a dry matter basis. In other such embodiments, the food compositions comprise from about 0.1 to about 0.3 mg/kg iodine on a dry matter basis and from about 0.15 to about 0.65 mg/kg selenium on a dry matter basis. In further such embodiments, the food compositions comprise (1) from about 0.1, about 0.15, or about 0.2 to about 0.25, about 0.3, or about 0.5 mg/kg iodine on a dry matter basis, and (2) from about 0.1, about 0.15, about 0.3, or about 0.4 to about 0.65, about 0.7, or about 0.8 mg/kg selenium on a dry matter basis.

As noted above, an animal, especially a hyperthyroid companion feline, may also be administered an antithyroid agent. Antithyroid agents suitable for the methods of treatment discussed above include, for example, thioureylenes, aniline derivatives, polyhydric phenols, and lithium salts. In some embodiments, the method comprises administering to the feline an antithyroid agent that comprises a thioureylene. In some embodiments, the method comprises administering an antithyroid agent comprising methimazole. In some embodiments, the method comprises administering to a feline an antithyroid agent comprising propylthiouracil. In some embodiments, the method comprises administering an antithyroid agent comprising carbimazole. In some embodiments, the method comprises administering a therapeutically-effective amount of an antithyroid agent in conjunction with feeding the feline a pet food composition of the invention. In some embodiments, the pet food composition fed to a feline comprises the antithyroid agent administered to the feline. In some such embodiments, the method comprises feeding the feline a food composition of the invention that comprises a therapeutically-effective amount of an antithyroid agent. Antithyroid agents can be administered, for example, in the form of salts derived from inorganic or organic acids. Depending on the particular compound, a salt of the compound may be advantageous due to one or more of the salt's physical properties, for example, enhanced pharmaceutical stability in differing temperatures and humidities, or a desirable solubility in water or oil. The salt preferably is a pharmaceutically-acceptable salt.

The preferred total daily dose of the antithyroid agent (administered in single or divided doses) is typically from about 0.001 to about 100 mg/kg body weight, more preferably from about 0.01 to about 30 mg/kg body weight, and even more preferably from about 0.01 to about 10 mg/kg body weight. Dosage unit compositions can contain such amounts and submultiples thereof to make up the daily dose.

In many instances, the administration of the antithyroid agent will be repeated a plurality of times. Multiple doses per day typically may be used to increase the total daily dose, if desired. Factors affecting the preferred dosage regimen include, for example, the age, weight, and condition of the feline; the severity of the disease; the route of administration; pharmacological considerations, such as the activity, efficacy, pharmacokinetic, and toxicology profiles of the particular antithyroid agent used; whether a drug delivery system is utilized; and whether the antithyroid agent is administered as part of a drug combination. Thus, the dosage regimen can vary widely, and therefore, can differ from the preferred dosage regimen discussed above.

In particular embodiments, the method of treatment can be tailored to the severity of the disease and the rate of recovery of the afflicted animal. For example, with respect to treatment of a hyperthyroid companion feline, such tailoring can take into account selections of one or more of the bioactive dietary components disclosed herein, the concentration of each in the food composition, the levels of iodine and selenium in the food composition, and whether or not the afflicted animal is also administered an antithyroid compound. This is particularly apparent in light of synergism to be expected through the use of the present methods which provide multiple points of intervention that are each expected to ameliorate, modulate, or remove one or more underlying factors that contribute to the development of a hyperthyroidism in a companion feline.

Accordingly, the methods of treatment of the invention are convenient and easy to practice. In some embodiments, it is sufficient to feed a composition of the invention to a feline diagnosed with hyperthyroidism. In some such embodiments, the composition does not contain any antithyroid agents nor are such agents administered to the feline in conjunction with feeding the feline the composition. Thus, such methods provide cost-effective alternatives to treatment with antithyroid agents. In addition, such methods do not cause the side effects attributed to treatment with antithyroid agents, for example, kidney damage. Finally, such methods result in better compliance because one need only feed a feline a composition of the invention rather than administer, for example, an oral or topical antithyroid drug. As discussed above, in some embodiments, the methods of treatment of the invention comprise feeding the feline a composition comprising an antithyroid agent. Such methods of treatment are more convenient and easier to practice because they eliminate the need for, for example, oral or topical administration of antithyroid agents. In some embodiments, the methods of treatment of the invention allow for administering less antithyroid agent than would be administered in a drug only treatment because the administration of an antithyroid agent in conjunction with feeding the feline a composition of the invention results in a synergistic cooperation between the antithyroid agent administered to the feline and the composition of the invention fed to the feline. In addition, one skilled in the art would know that either a single composition of the invention can be fed to the feline or that different compositions of the invention can be fed to the feline for varying time intervals.

In one embodiment, the methods of the present invention comprise feeding a feline afflicted with hyperthyroidism a composition comprising an effective amount of a bioactive dietary component sufficient to suppress expression or activity of at least one polypeptide required for biosynthesis, transport, or activity of either or both of thyroxine or triiodothyronine, which comprises:

(a) from about 0.1% to about 20%, from about 0.25% to about 15%, from about 0.75% to about 12.5%, from about 1% to about 10%, from about 2% to about 8% from about 3% to about 7%, from about 4% to about 6%, or about 5% of a vegetable blend;

(b) from about 10% to about 50%, from about 15% to about 45%, from about 20% to about 40%, or from about 25% to about 35% protein;

(c) from about 10% to about 50%, from about 15% to about 45%, from about 20% to about 40%, or from about 25% to about 35% fat; and (d) from about 10% to about 60%, from about 20% to about 50%, from about 25% to about 45%, or from about 30% to about 40% carbohydrate.

In a specific embodiment, the methods of the present invention comprise feeding a feline afflicted with hyperthyroidism a composition comprising about 5% of a vegetable blend, about 30% protein, about 27%, fat, and about 35% carbohydrate.

In another specific embodiment, the methods of the present invention comprise feeding a feline afflicted with hyperthyroidism a composition comprising about 5% of a vegetable blend, about 35% protein, about 20%, fat, and about 35% carbohydrate.

In still another specific embodiment, the methods of the present invention comprise feeding a feline afflicted with hyperthyroidism a composition comprising about 5% of a vegetable blend, about 20% protein, about 15%, fat, and about 57% carbohydrate.

In another embodiment, the methods of the present invention comprise feeding a feline afflicted with hyperthyroidism a composition comprising an effective amount of a bioactive dietary component sufficient to suppress expression or activity of at least one polypeptide required for biosynthesis, transport, or activity of either or both of thyroxine or triiodothyronine, which comprises:

(a) from about 0.1% to about 20%, from about 0.25% to about 15%, from about 0.75% to about 12.5%, from about 1% to about 10%, from about 2% to about 8% from about 3% to about 7% from about 4% to about 6%, or about 5% of tomato pomace;

(b) from about 10% to about 50%, from about 15% to about 45%, from about 20% to about 40%, or from about 25% to about 35% protein;

(c) from about 10% to about 50%, from about 15% to about 45%, from about 20% to about 40%, or from about 25% to about 35% fat; and (d) from about 10% to about 60%, from about 20% to about 50%, from about 25% to about 45%, or from about 30% to about 40% carbohydrate.

In a specific embodiment, the methods of the present invention comprise feeding a feline afflicted with hyperthyroidism a composition comprising about 5% of tomato pomace, about 30% protein, about 27%, fat, and about 35% carbohydrate.

In another specific embodiment, the methods of the present invention comprise feeding a feline afflicted with hyperthyroidism a composition comprising about 5% of tomato pomace, about 35% protein, about 20%, fat, and about 35% carbohydrate.

In still another specific embodiment, the methods of the present invention comprise feeding a feline afflicted with hyperthyroidism a composition comprising about 5% of tomato pomace, about 20% protein, about 15%, fat, and about 57% carbohydrate.

In one embodiment, the methods of the present invention comprise feeding a feline afflicted with hyperthyroidism a composition comprising an effective amount of a bioactive dietary component sufficient to suppress expression or activity of at least one polypeptide required for biosynthesis, transport, or activity of either or both of thyroxine or triiodothyronine, which comprises:

(a) from about 0.1% to about 20%, from about 0.25% to about 15%, from about 0.75% to about 12.5%, from about 1% to about 10%, from about 2% to about 8% from about 3% to about 7% from about 4% to about 6%, or about 5% of millet;

(b) from about 10% to about 50%, from about 15% to about 45%, from about 20% to about 40%, or from about 25% to about 35% protein;

(c) from about 10% to about 50%, from about 15% to about 45%, from about 20% to about 40%, or from about 25% to about 35% fat; and (d) from about 10% to about 60%, from about 20% to about 50%, from about 25% to about 45%, or from about 30% to about 40% carbohydrate.

In a specific embodiment, the methods of the present invention comprise feeding a feline afflicted with hyperthyroidism a composition comprising about 5% millet, about 30% protein, about 27%, fat, and about 35% carbohydrate.

In another specific embodiment, the methods of the present invention comprise feeding a feline afflicted with hyperthyroidism a composition comprising about 5% millet, about 35% protein, about 20%, fat, and about 35% carbohydrate.

In still another specific embodiment, the methods of the present invention comprise feeding a feline afflicted with hyperthyroidism a composition comprising about 5% millet, about 20% protein, about 15%, fat, and about 57% carbohydrate.

In one embodiment, the methods of the present invention comprise feeding a feline afflicted with hyperthyroidism a composition comprising an effective amount of a bioactive dietary component sufficient to suppress expression or activity of at least one polypeptide required for biosynthesis, transport, or activity of either or both of thyroxine or triiodothyronine, which comprises:

(a) from about 0.1% to about 20%, from about 0.25% to about 15%, from about 0.75% to about 12.5%, from about 1% to about 10%, from about 2% to about 8% from about 3% to about 7% from about 4% to about 6%, or about 5% of a vegetable blend, and from about 0.1% to about 20%, from about 0.25% to about 15%, from about 0.75% to about 12.5%, from about 1% to about 10%, from about 2% to about 8% from about 3% to about 7% from about 4% to about 6%, or about 5% of soybean meal.

(b) from about 10% to about 50%, from about 15% to about 45%, from about 20% to about 40%, or from about 25% to about 35% protein;

(c) from about 10% to about 50%, from about 15% to about 45%, from about 20% to about 40%, or from about 25% to about 35% fat; and (d) from about 10% to about 60%, from about 20% to about 50%, from about 25% to about 45%, or from about 30% to about 40% carbohydrate.

In a specific embodiment, the methods of the present invention comprise feeding a feline afflicted with hyperthyroidism a composition comprising about 5% of a vegetable blend, about 5% soybean meal, and about 30% protein, about 27%, fat, and about 35% carbohydrate.

In another specific embodiment, the methods of the present invention comprise feeding a feline afflicted with hyperthyroidism a composition comprising about 5% of a vegetable blend, about 5% soybean meal, about 35% protein, about 20%, fat, and about 35% carbohydrate.

In still another specific embodiment, the methods of the present invention comprise feeding a feline afflicted with hyperthyroidism a composition comprising about 5% of a vegetable blend, about 5% soybean meal, about 20% protein, about 15%, fat, and about 57% carbohydrate.

In another embodiment, the methods of the present invention comprise feeding a feline afflicted with hyperthyroidism a composition comprising an effective amount of a bioactive dietary component sufficient to suppress expression or activity of at least one polypeptide required for biosynthesis, transport, or activity of either or both of thyroxine or triiodothyronine, which comprises:

(a) from about 0.1% to about 20%, from about 0.25% to about 15%, from about 0.75% to about 12.5%, from about 1% to about 10%, from about 2% to about 8% from about 3% to about 7% from about 4% to about 6%, or about 5% of tomato pomace; and from about 0.1% to about 20%, from about 0.25% to about 15%, from about 0.75% to about 12.5%, from about 1% to about 10%, from about 2% to about 8% from about 3% to about 7% from about 4% to about 6%, or about 5% of soybean meal;

(b) from about 10% to about 50%, from about 15% to about 45%, from about 20% to about 40%, or from about 25% to about 35% protein;

(c) from about 10% to about 50%, from about 15% to about 45%, from about 20% to about 40%, or from about 25% to about 35% fat; and (d) from about 10% to about 60%, from about 20% to about 50%, from about 25% to about 45%, or from about 30% to about 40% carbohydrate.

In a specific embodiment, the methods of the present invention comprise feeding a feline afflicted with hyperthyroidism a composition comprising about 5% tomato pomace, about 5% soybean meal, about 30% protein, about 27%, fat, and about 35% carbohydrate.

In another specific embodiment, the methods of the present invention comprise feeding a feline afflicted with hyperthyroidism a composition comprising about 5% tomato pomace, about 5% soybean meal, about 35% protein, about 20%, fat, and about 35% carbohydrate.

In still another specific embodiment, the methods of the present invention comprise feeding a feline afflicted with hyperthyroidism a composition comprising about 5% tomato pomace, about 5% soybean meal, about 20% protein, about 15%, fat, and about 57% carbohydrate.

In one embodiment, the methods of the present invention comprise feeding a feline afflicted with hyperthyroidism a composition comprising an effective amount of a bioactive dietary component sufficient to suppress expression or activity of at least one polypeptide required for biosynthesis, transport, or activity of either or both of thyroxine or triiodothyronine, which comprises:

(a) from about 0.1% to about 20%, from about 0.25% to about 15%, from about 0.75% to about 12.5%, from about 1% to about 10%, from about 2% to about 8% from about 3% to about 7% from about 4% to about 6%, or about 5% of millet; and from about 0.1% to about 20%, from about 0.25% to about 15%, from about 0.75% to about 12.5%, from about 1% to about 10%, from about 2% to about 8% from about 3% to about 7% from about 4% to about 6%, or about 5% of soybean meal;

(b) from about 10% to about 50%, from about 15% to about 45%, from about 20% to about 40%, or from about 25% to about 35% protein;

(c) from about 10% to about 50%, from about 15% to about 45%, from about 20% to about 40%, or from about 25% to about 35% fat; and (d) from about 10% to about 60%, from about 20% to about 50%, from about 25% to about 45%, or from about 30% to about 40% carbohydrate.

In a specific embodiment, the methods of the present invention comprise feeding a feline afflicted with hyperthyroidism a composition comprising about 5% millet, about 5% soybean meal, about 30% protein, about 27%, fat, and about 35% carbohydrate.

In another specific embodiment, the methods of the present invention comprise feeding a feline afflicted with hyperthyroidism a composition comprising about 5% millet, about 5% soybean meal, about 35% protein, about 20%, fat, and about 35% carbohydrate.

In still another specific embodiment, the methods of the present invention comprise feeding a feline afflicted with hyperthyroidism a composition comprising about 5% millet, about 5% soybean meal, about 20% protein, about 15%, fat, and about 57% carbohydrate.

In another embodiment, the methods of the present invention comprise feeding a feline afflicted with hyperthyroidism a composition comprising an effective amount of a bioactive dietary component sufficient to suppress expression or activity of at least one polypeptide required for biosynthesis, transport, or activity of either or both of thyroxine or triiodothyronine, which comprises:

(a) from about 0.1% to about 20%, from about 0.25% to about 15%, from about 0.75% to about 12.5%, from about 1% to about 10%, from about 2% to about 8% from about 3% to about 7% from about 4% to about 6%, or about 5% of a vegetable blend, and from about 0.1% to about 20%, from about 0.25% to about 15%, from about 0.75% to about 12.5%, from about 1% to about 10%, from about 2% to about 8% from about 3% to about 7% from about 4% to about 6%, or about 5% of potato concentrate.

(b) from about 10% to about 50%, from about 15% to about 45%, from about 20% to about 40%, or from about 25% to about 35% protein;

(c) from about 10% to about 50%, from about 15% to about 45%, from about 20% to about 40%, or from about 25% to about 35% fat; and (d) from about 10% to about 60%, from about 20% to about 50%, from about 25% to about 45%, or from about 30% to about 40% carbohydrate.

In a specific embodiment, the methods of the present invention comprise feeding a feline afflicted with hyperthyroidism a composition comprising about 5% of a vegetable blend, about 5% potato concentrate, and about 30% protein, about 27%, fat, and about 35% carbohydrate.

In another specific embodiment, the methods of the present invention comprise feeding a feline afflicted with hyperthyroidism a composition comprising about 5% of a vegetable blend, about 5% potato concentrate, about 35% protein, about 20%, fat, and about 35% carbohydrate.

In still another specific embodiment, the methods of the present invention comprise feeding a feline afflicted with hyperthyroidism a composition comprising about 5% of a vegetable blend, about 5% potato concentrate, about 20% protein, about 15%, fat, and about 57% carbohydrate.

In another embodiment, the methods of the present invention comprise feeding a feline afflicted with hyperthyroidism a composition comprising an effective amount of a bioactive dietary component sufficient to suppress expression or activity of at least one polypeptide required for biosynthesis, transport, or activity of either or both of thyroxine or triiodothyronine, which comprises:

(a) from about 0.1% to about 20%, from about 0.25% to about 15%, from about 0.75% to about 12.5%, from about 1% to about 10%, from about 2% to about 8% from about 3% to about 7% from about 4% to about 6%, or about 5% of tomato pomace; and from about 0.1% to about 20%, from about 0.25% to about 15%, from about 0.75% to about 12.5%, from about 1% to about 10%, from about 2% to about 8% from about 3% to about 7% from about 4% to about 6%, or about 5% potato concentrate;

(b) from about 10% to about 50%, from about 15% to about 45%, from about 20% to about 40%, or from about 25% to about 35% protein;

(c) from about 10% to about 50%, from about 15% to about 45%, from about 20% to about 40%, or from about 25% to about 35% fat; and (d) from about 10% to about 60%, from about 20% to about 50%, from about 25% to about 45%, or from about 30% to about 40% carbohydrate.

In a specific embodiment, the methods of the present invention comprise feeding a feline afflicted with hyperthyroidism a composition comprising about 5% tomato pomace, about 5% potato concentrate, about 30% protein, about 27%, fat, and about 35% carbohydrate.

In another specific embodiment, the methods of the present invention comprise feeding a feline afflicted with hyperthyroidism a composition comprising about 5% tomato pomace, about 5% potato concentrate, about 35% protein, about 20%, fat, and about 35% carbohydrate.

In still another specific embodiment, the methods of the present invention comprise feeding a feline afflicted with hyperthyroidism a composition comprising about 5% tomato pomace, about 5% potato concentrate, about 20% protein, about 15%, fat, and about 57% carbohydrate.

In one embodiment, the methods of the present invention comprise feeding a feline afflicted with hyperthyroidism a composition comprising an effective amount of a bioactive dietary component sufficient to suppress expression or activity of at least one polypeptide required for biosynthesis, transport, or activity of either or both of thyroxine or triiodothyronine, which comprises:

(a) from about 0.1% to about 20%, from about 0.25% to about 15%, from about 0.75% to about 12.5%, from about 1% to about 10%, from about 2% to about 8% from about 3% to about 7% from about 4% to about 6%, or about 5% of millet; and from about 0.1% to about 20%, from about 0.25% to about 15%, from about 0.75% to about 12.5%, from about 1% to about 10%, from about 2% to about 8% from about 3% to about 7% from about 4% to about 6%, or about 5% potato concentrate;

(b) from about 10% to about 50%, from about 15% to about 45%, from about 20% to about 40%, or from about 25% to about 35% protein;

(c) from about 10% to about 50%, from about 15% to about 45%, from about 20% to about 40%, or from about 25% to about 35% fat; and (d) from about 10% to about 60%, from about 20% to about 50%, from about 25% to about 45%, or from about 30% to about 40% carbohydrate.

In a specific embodiment, the methods of the present invention comprise feeding a feline afflicted with hyperthyroidism a composition comprising about 5% millet, about 35% potato concentrate, about 30% protein, about 27%, fat, and about 35% carbohydrate.

In another specific embodiment, the methods of the present invention comprise feeding a feline afflicted with hyperthyroidism a composition comprising about 5% millet, about 5% potato concentrate, about 35% protein, about 20%, fat, and about 35% carbohydrate.

In still another specific embodiment, the methods of the present invention comprise feeding a feline afflicted with hyperthyroidism a composition comprising about 5% millet, about 5% potato concentrate, about 20% protein, about 15%, fat, and about 57% carbohydrate.

The vegetable blend described above may comprise material prepared from any or all of the following vegetables: brussel sprouts, cabbage, cauliflower, kale, kohlrabi, rutabaga, turnips, radishes, and combinations thereof. In one aspect of this embodiment, the vegetable blend may further comprise mustard, peaches, peanuts, and strawberries.

In other embodiments, the present invention is directed to a food composition, that is suitable for use in a method for treating hyperthyroidism in a companion animal, the composition comprising an effective amount of bioactive dietary component sufficient to suppress expression or activity of at least one polypeptide required for biosynthesis, transport, or activity of either of both of thyroxine and triiodothyronine. Accordingly, the food compositions include each of the compositions described above that are useful in the preceding methods.

In still other embodiments, as noted above, the composition of the invention is a pet food composition (i.e., the composition can comprise one or more food compositions). In some such embodiments, the composition meets the AAFCO's minimum nutrient, level requirements for reproduction or maintenance. See AAFCO Official Publication, pages 159-162 (2005). In other such embodiments, the pet food composition comprises less than the AAFCO's minimum requirements for reproduction or maintenance (e.g., the pet food composition comprises less iodine and/or selenium than the amount recommended by the AAFCO). In some embodiments, the pet food composition is formulated as a dry food. In some embodiments, the pet food composition is formulated as a semi-moist food. In some embodiments, the pet food composition is formulated as a moist food. In some embodiments, the pet food composition is formulated and prepared as a supplement, treat, snack, or partially or fully edible toy. In some embodiments, the pet food composition comprises a mixture of two or more foods.

In certain aspects of these embodiments, the pet food compositions of the disclosure also may comprise additional ingredients, including essential amino acids and nutrients. In one embodiment "essential amino acids" as used herein refers to those amino acids that cannot be synthesized de novo by an organism and thus must be supplied in the diet. It is understood by one of skill in the art that the essential amino acids varies from species to species, depending upon the organism's metabolism. For example, it is generally understood that the essential amino acids for dogs and cats, are phenylalanine, leucine, methionine, lysine, isoleucine, valine, threonine, tryptophan, histidine and arginine. In other embodiments, the pet food compositions disclosed here are also supplemented with the amino acid lysine.

In another embodiment the pet food compositions disclosed herein may also comprise "essential nutrients," which, as used herein refers to nutrients required for normal body functioning that cannot be synthesized by the body. Categories of essential nutrients include vitamin dietary minerals, fatty acid, and amino acid. It is understood by one of skill in the art that the nutrients deemed essential varies from species to species, depending upon the organism's metabolism. For example, essential nutrients for dogs and cats include Vitamins A, D, E, K, $B_1$, $B_6$, $B_{12}$, riboflavin, niacin, pantothenic acid, folic acid, calcium, phosphorous, magnesium, sodium, potassium, chlorine, iron, copper, zinc, manganese, selenium and iodine. As noted above, the amounts of iodine and selenium in the pet food compositions disclosed herein may be lower than the recommended levels set forth by AAFCO.

Choline, generally regarded as a B complex vitamin, may be included among the semi-essential nutrients. In addition, taurine, while technically not an amino acid but a derivative of cysteine, is an essential nutrient for cats. In still another aspect, the pet food compositions of the present disclosure may also comprise carnitine, also known as L-carnitine, (levocarnitine), which is a quaternary ammonium compound synthesized from the amino acids lysine and methionine and is responsible for the transport of fatty acids from the cytosol into the mitochondria.

Accordingly, in one certain embodiment, a pet food composition useful in the disclosed method for treating hyperthyroidism may contain one or more of the above-identified bioactive dietary components in the amounts disclosed, as well as iodine and selenium (e.g., as calcium iodate, iodized salt, and sodium selenite) at the above-identified levels and may further comprise: pork liver, chicken, pork by-products, brewers rice, corn starch, glucose, chicken fat (preserved with mixed tocopherols and citric acid), potassium citrate, calcium carbonate, fish oil, calcium sulfate, DL-methionine, choline chloride, taurine, vitamin E supplement, L-cysteine, glycine, thiamine mononitrate, ascorbic acid, zinc oxide, ferrous sulfate, niacin, beta carotene, manganous oxide, copper sulfate, pyridoxine hydrochloride, calcium pantothenate, vitamin B12 supplement, riboflavin, biotin, vitamin D3 supplement, and folic acid.

In another embodiment, a pet food composition useful in the disclosed method for treating hyperthyroidism may contain one or more of the above-identified bioactive dietary components in the amounts disclosed, as well as iodine and selenium (e.g., as calcium iodate, iodized salt, and sodium selenite) at the above-identified levels and may further comprise: water, pork liver, chicken, pork by-products, brewers rice, corn starch, glucose, chicken fat (preserved with mixed tocopherols and citric acid), potassium citrate, calcium carbonate, fish oil, calcium sulfate, DL-methionine, choline chloride, taurine, vitamin E supplement, L-cysteine, glycine, thiamine mononitrate, ascorbic acid, zinc oxide, ferrous sulfate, niacin, beta carotene, manganous oxide, copper sulfate, pyridoxine hydrochloride, calcium pantothenate, vitamin B12 supplement, riboflavin, biotin, vitamin D3 supplement, and folic acid.

In another certain embodiment, a pet food composition useful in the disclosed method for treating hyperthyroidism may contain one or more of the above-identified bioactive dietary components in the amounts disclosed, as well as iodine and selenium (e.g., as calcium iodate, iodized salt, and sodium selenite) at the above-identified levels and may further comprise: chicken by-product meal, corn gluten meal, brewers rice, animal fat (preserved with mixed tocopherols and citric acid), L-lysine, lactic acid, chicken liver flavor, potassium chloride, choline chloride, vitamin E supplement, calcium sulfate, vitamins (L-ascorbyl-2-polyphosphate (source of vitamin C), vitamin E supplement, niacin, thiamine mononitrate, vitamin A supplement, calcium pantothenate, riboflavin, biotin, vitamin B12 supplement, pyridoxine hydrochloride, folic acid, vitamin D3 supplement), taurine, natural flavor, calcium carbonate, fish oil, minerals (ferrous sulfate, zinc oxide, copper sulfate, manganous oxide), L-carnitine, preserved with mixed tocopherols and citric acid, phosphoric acid, beta-carotene, and rosemary extract.

In still another certain embodiment, a pet food composition useful in the disclosed method for treating hyperthyroidism may contain one or more of the above-identified bioactive dietary components in the amounts disclosed, as well as iodine and selenium (e.g., as calcium iodate, iodized salt, and sodium selenite) at the above-identified levels and may further comprise: chicken by-product meal, animal fat (preserved with mixed tocopherols and citric acid), chicken liver flavor, lactic acid, corn gluten meal, potassium chloride, L-lysine, choline chloride, vitamin E supplement, vitamins (L-ascorbyl-2-polyphosphate (source of vitamin C), vitamin E supplement, niacin, thiamine mononitrate, vitamin A supplement, calcium pantothenate, biotin, vitamin B12 supplement, pyridoxine hydrochloride, riboflavin, folic acid, vitamin D3 supplement), calcium carbonate, dicalcium phosphate, minerals (ferrous sulfate, zinc oxide, copper sulfate, and manganous oxide), L-tryptophan, taurine, glucosamine hydrochloride, L-carnitine, preserved with mixed tocopherols and citric acid, chondroitin sulfate, phosphoric acid, beta-carotene, and rosemary extract.

Examples of suitable protein sources that may be included in the compositions described herein encompass but are not to be limited to, animal sources such as meat protein isolate, whey protein isolate, mixtures thereof, and the like, as well as vegetable sources, such as corn gluten meal, wheat gluten, mixtures thereof, and the like. Examples of suitable sources of fat that may be included in the compositions described herein include but are not limited to, poultry fat, beef tallow, lard, choice white grease, soybean oil, corn oil, canola oil, sunflower oil, mixtures thereof, and the like. The fat may be incorporated completely within the food composition, deposited on the outside of the food composition, or a mixture of the two methods. Examples of suitable carbohydrate sources that may be included in the compositions described herein encompass, but are not to be limited to a component of another ingredient, such as the protein source, as well as starches and grains, such as corn, wheat, sorghum, barley, rice, mixtures thereof, and the like.

In particular embodiments, the pet food compositions useful in the methods disclosed herein may also contain a fiber supplement, generally comprising from about 1% to about 5% of the composition. Suitable sources of such fiber include, but are not to be limited to, whole grain corn, oat fiber, psyllium seed husk, guar gum, flaxseed, soybean mill run, and combinations thereof.

Illustrative embodiments of the disclosed methods of treatment and pet food compositions are set forth in the following paragraphs.

In one embodiment, the present disclosure provides a method for treating hyperthyroidism in a companion animal, the method comprising feeding a companion animal in need thereof a pet food composition comprising an effective amount of a bioactive dietary component sufficient to suppress expression or activity of at least one polypeptide required for biosynthesis, transport, or activity of either of both of thyroxine and triiodothyronine.

In one aspect of this embodiment, the polypeptide is a biosynthetic enzyme selected from the group consisting of thyroid peroxidase, sodium/iodide symporter, thyroid oxidase, and intrathyroidal type I 5' deiodinase, and combinations thereof.

In one aspect of this embodiment, the polypeptide is selected from the group consisting of thyroid stimulating hormone, thyroid stimulating hormone receptor, a thyroid hormone receptor activator molecule, pendrin, and monocarboxylate transporter 8, and combinations thereof.

In one aspect of this embodiment, the companion animal is a feline.

In one aspect of this embodiment, the administered pet food composition comprises a bioactive dietary component selected from the group consisting of tomato pomace, vegetable blend, millet, soybean meal, potato concentrate, and combinations thereof. In one aspect of this embodiment, the biologically active material comprises from about 0.1% to about 20% of the pet food composition on a dry matter basis. In another aspect of this embodiment, the biologically active material comprises from about 1% to about 10% of the pet food composition on a dry matter basis.

In one aspect of this embodiment, the administered pet food composition comprises from about 15 to about 45% protein, from about 15 to about 45% fat, from about 20 to 50% carbohydrate on a dry matter basis, and from about 2 to about 8% biologically active material on a dry matter basis.

In one aspect of this embodiment, the administered pet food composition comprises from about 25 to about 35% protein, from about 25 to about 35% fat, from about 30 to 40% carbohydrate, and from about 2 to about 8% biologically active material on a dry matter basis.

In one aspect of this embodiment, the administered pet food composition comprises 0.1 to less than about 1 mg/kg iodine on a dry matter basis.

In one aspect of this embodiment, the administered pet food composition comprises 0.1 to about 1 mg/kg selenium on a dry matter basis.

In one aspect of this embodiment, the method further comprises administration of a therapeutically effective amount of an antithyroid agent, e.g., wherein the antithyroid agent is selected from the group consisting of methimazole, propylthiouracil, carbimazole, and combinations thereof.

In another embodiment, the present disclosure provides a pet food composition, wherein the pet food composition is suitable for use in a method for treating hyperthyroidism in a companion animal, the composition comprising an effective amount of a bioactive dietary component sufficient to suppress expression or activity of at least one polypeptide required for biosynthesis, transport, or activity of either of both of thyroxine and triiodothyronine.

In one aspect of this embodiment, the polypeptide is a biosynthetic enzyme selected from the group consisting of thyroid peroxidase, sodium/iodide symporter, thyroid oxidase, and intrathyroidal type I 5' deiodinase, and combinations thereof.

In one aspect of this embodiment, the polypeptide is selected from the group consisting of a thyroid hormone receptor activator molecule, thyroid stimulating hormone receptor, pendrin, monocarboxylate transporter 8, and combinations thereof.

In one aspect of this embodiment the companion animal is a feline.

In one aspect of this embodiment, the bioactive dietary component is selected from the group consisting of tomato pomace, vegetable blend, millet, soybean meal, potato concentrate, and combinations thereof.

In one aspect of this embodiment, the biologically active material comprises from about 0.1% to about 20% of the pet food composition on a dry matter basis.

In one aspect of this embodiment, the biologically active material comprises from about 1% to about 10% of the pet food composition on a dry matter basis.

In another aspect of this embodiment, the composition comprises from about 15 to about 45% protein, from about 15 to about 45% fat, from about 20 to 50% carbohydrate, and from about 2 to about 8% biologically active material on a dry matter basis.

In another aspect of this embodiment, the composition comprises from about 25 to about 35% protein, from about 25 to about 35% fat, from about 30 to 40% carbohydrate, and from about 2 to about 8% biologically active material on a dry matter basis.

In another aspect of this embodiment, the composition comprises from about 0.1 to less than about 1 mg/kg iodine on a dry matter basis.

In another aspect of this embodiment, the composition comprises from about 0.1 to about 1 mg/kg selenium on a dry matter basis.

In another aspect of this embodiment, the composition comprises a therapeutically effective amount of an antithyroid agent, wherein the antithyroid agent is selected from the group consisting of methimazole, propylthiouracil, carbimazole, and combinations thereof.

The present disclosure therefore encompasses a method for design of a food composition suitable for treating a disease or condition in an animal, the method comprising: (a) identifying a target disease or condition; (b) identifying a polypeptide involved in the etiology underlying that disease; (c) determining whether an increase or a decrease in activity or expression of said identified polypeptide would ameliorate the target disease or condition; (d) performing at least one multivariate analysis to identify bioactive dietary components capable of modulating activity or expression of said identified polypeptide in a manner required to ameliorate the target disease or condition; and (e) formulating a food composition comprising the bioactive dietary component.

The invention is not limited to the particular methodology, protocols, and reagents described herein because they may vary. Further, the terminology used herein is for the purpose of describing particular embodiments only and is not intended to limit the scope of the present invention.

All patents, patent applications, publications, and other references cited or referred to herein are incorporated herein by reference to the extent allowed by law. The discussion of those references is intended merely to summarize the assertions made therein.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

EXAMPLES

Example 1

Identification of Genes with Altered Expression in Hyperthyroid Felines (Cats)

In the examples that follow, reporting on cats for which gene expression data is obtained by DNA microarray analysis, selection criteria are established in order to identify certain genes and expressed proteins as suitable biological markers of hyperthyroidism in felines (cats). A skilled worker can select among a number of algorithms for analyzing gene chip data. These include MASS statistical algorithm, probe logarithmic intensity error estimation (PLIER) and robust multi-chip analysis (RMA). Processing algorithms are discussed in detail in the following references: Li, C. Mo, 2001, Model-based analysis of oligonucleotide arrays: expression index computation and outlier detection, *Proc. Acad. Sci. USA, Vol.* 98:31-36; Irizarry R. A. et al., Exploration, normalization and summaries of high density oligonucleotide array probe level data, *Biostatistics*, 2003, Vol. 4:249-264; Irizarry et al., Summaries of Affymetrix GeneChip probe level data, *Nucleic Acid Res.*, 2003, Vol. 31(4): e15; and Fan, W., A. et al., A class of models for analyzing GeneChip gene expression analysis array data, *BMC Genomics*, 2005, Vol. 16: 6-16; Zhou, L. et al., An expression index for Affymetrix GeneChips based on the generalized logarithm, *Bioinformatics*, 2005, Vol. 21(21): 3983-3989 and Hein A. K. et al., BGX: a fully Bayesian integrated approach to the analysis of Affymetrix GeneChip data, *Biostatistics*, 2005, Vol. 6: 349-373.

The raw data in the following examples is analyzed using GeneSpring version 7.0 (GS) software (Agilent Corporation) and validated using the R-Bioconductor (RB) freeware. Both software packages are used to compute probe intensities from the CEL files generated by the Affymetrix Instrument. The Present/Absent/Marginal calls per probe and P-values are computed using the R-Bioconductor and GeneSpring software separately.

The gene expression data is determined to be either "up" or "down" regulated for any given analysis. The decision on whether a gene is "up" or "down" is based on the fold change, which is calculated as treatment intensity/control intensity for each individual probe. The fold change is considered down-regulated if its value is reduced by a value of about 10%, about 15%, about 20%, about 25%, about 30%, about 35%, about 40%, about 45%, or about 50% or more and is upregulated if it is increased by a value of about 10%, about 15%, about 20%, about 25%, about 30%, about 35%, about 40%, about 45%, or about 50% or more. Also, a probe is considered significant for further scrutiny if it is called as present in only one of the conditions being compared (treatment or control) and is "absent" or "marginal" in the other and the fold change is significant according to the software used.

Example 2

Blood Sample Collection and RNA Isolation

Blood is collected and processed according to the manufacturers' instructions in the PAXgene manual. The PAXgene tubes are stored at −20° C. before RNA is isolated. RNA is isolated from the PAXgene RNA blood tubes (VWR, p/n 77776-026) using the PAXgene Blood RNA Isolation Kit (Qiagen, p/n 762164) according to the manufacturer's instructions. The RNA quantity and quality is determined using the Agilent 2100 Bioanalyzer (Agilent Technologies) and the RNA 6000 Nano chip kit (Agilent, p/n 5067-1511) according to the manufacturer's instructions. RNA integrity is determined by 28S:18S ribosomal RNA ratio and RNA integrity number (RIN; Agilent 2100 RIN Beta Version Software). Purified RNA samples are stored at −80° C.

Example 3

RNA Isolation from Tissue

Tissues are collected from felines and are dissected into small pieces, placed into cryogenic vials and immediately frozen in liquid nitrogen. Tissue samples are homogenized using Tissue Lyser (SOP Number.Version: LAB-LS-028.3). RNA is isolated with the RNeasy RNA Isolation Kit according to the manufacturers' instructions. All extracted RNA samples are quantified by absorbance readings at 260 and 280 nm with a NanoDrop 1000 spectrophotometer (Thermo Scientific). The RNA quality is determined with a 2100 Bioanalyzer (Agilent Technologies) according to the manufacturer's instructions. RNA integrity is determined by 28S:18S ribosomal RNA ratio and RNA integrity number (RIN; Agilent 2100 RIN Beta Version Software). Purified RNA samples are stored at −80° C.

Example 4

Probe Preparation

Labeling and amplification reagents are obtained from NuGEN Technologies, Inc. (San Carlos, Calif., USA) and include the Ovation RNA Amplification System V2 (p/n 3100-A01), Ovation® Whole Blood Solution (p/n 1300-A01) and Encore Biotin Module (p/n 4200-A01). Biotinylated cDNA targets are prepared according to manufacturer's instructions. Double-stranded cDNA is synthesized from 50 ng total RNA, followed by a linear isothermal amplification (SPIA Amplification™) step to produce single-stranded cDNA. Fragmentation is followed by a direct labeling process that attached biotin to the amplified probe. Probe purifications is performed using RNAClean XP, a magnetic bead product that is used to purify and clean the synthesized cDNA (Beckman Genomics, p/n A63987).

Example 5

Array Hybridization and Processing

After pre-hybridization for 10 minutes at 45° C., 4.4 μg of each target cDNA is mixed with Affymetrix hybridization controls (Affymetrix, p/n 900454) in hybridization buffer and hybridized with an Affymetrix Feline-2 GeneChip® for 16-18 hours at 45° C. After the hybridization cocktails are removed, the GeneChips® is washed in a fluidics station with low-stringency buffer (6× standard saline phosphate with EDTA, 0.01% Tween 20) and high stringency buffer (100 mM N-morpholino-ethanesulfonic acid (MES), 0.1 M NaCl, and 0.01% Tween 20) and stained with SAPE (streptavidin phycoerythrin, Invitrogen, p/n S-866). This process is followed by incubation with normal goat IgG and biotinylated mouse anti-streptavidin antibody (Vector Lab, BA-0500) followed by re-staining with SAPE. The chips are scanned in a GeneChip® Scanner 3000 7G (Affymetrix Inc., Santa Clara, Calif.) to detect hybridization signals. Image inspection is performed manually immediately following each scan (GeneChip® Expression Analysis Technical Manual. P/N 702232 Rev. 3, Chapter II and III).

Example 6

Data Analysis

The Partek® GS (Partek Inc., St. Charles, Mo.) for Gene Expression Data software (Partek Incorporated, 12747 Olive Blvd., Suite 205, St. Louis, Mo. 63141, U.S.A. http://www.partek.com/partekgs_geneexpression) is used for data analysis. The Robust Multichip Average (RMA) algorithm (Rafael. A. Irizarry, Benjamin M. Bolstad, Francois Collin, Leslie M. Cope, Bridget Hobbs and Terence P. Speed (2003), Summaries of Affymetrix GeneChip probe level data Nucleic Acids Research 31(4):e15) is used for background adjustment, normalization, and probe-level summarization of the GeneChip® samples. The ANOVA analysis is performed to find significant differentially expressed genes between any two groups with a minimal FDR control at 0.1 and a fold change of 1.25 in each direction. Empirical studies reveal that the Feline-2 GeneChips® have an associated background noise level of 1.3 fold. Therefore, all analyses presented report employ a +/−1.25 fold cut-off. Furthermore, the false discovery rate threshold of 0.1 (means that 10% of observations are due to chance) is chosen as the minimum level of acceptable statistical significance.

Example 7

Detailed RNA Isolation Procedures

Materials and Methods. The following general procedures may be used to isolate RNA from tissue samples of felines and felines for gene expression profiling utilizing gene chips as further described in the Examples of this specification. It will be apparent to a person of ordinary skill in the art that these procedures or modifications thereof, as recognized within the art, can be applied to isolate RNA from tissue or body fluid samples for further gene expression analysis using a variety of analytical procedures available to a person of ordinary skill in the art, in particular microarray technologies.

Isolation of Ribonucleic Acid (RNA) from Tissue. Tissue samples may be collected, frozen in liquid nitrogen, thawed and then, ground in a mortar and pestle, homogenized and transferred to a 50 ml conical flask. The homogenized tissue sample is then processed using a TRIzol® RNA extraction method according to the manufacturer's instructions (Invitrogen) to produce good quality RNA which is then subjected to further genomic analysis.

Materials: ice, liquid nitrogen, frozen feline tissue, TRIzol® lysis reagent, chloroform minimum 99%, isopropyl alcohol, 70% ethanol (prepared with ethanol, absolute and deionized, RNase-free water), RNase Zap®, deionized water, RNA Storage Solution®, from Ambion.

Equipment: Ultra-Turrax T25 Power Homogenizer, Beckman Coulter Allegra 25R Centrifuge, Eppendorf Centrifuge, forceps, scalpel, hard cutting surface, i.e. cutting board, 1.5 mL DNase and RNase free/sterile microcentrifuge tubes, 50 mL DNase and RNase free/sterile disposable polypropylene tubes, P1000, P200, P20, P10 and P2 Rainin Pipetman pipettes, filter pipette tips for P1000, P200, P20, P10 and P2 pipettes, DNase and RNase free/sterile, and lint free wipes.

Preparations: Prepare 50 mL polypropylene tubes with 4 mL TRIzol® (one tube for each tissue selected for RNA isolation).

Tissue Homogenization: Fill a container capable of holding liquid nitrogen with 3-4 scoops of liquid nitrogen. Place a piece of frozen tissue immediately into the aforementioned container (the tissue should be about the size of a pea) and place the tissue into the appropriate labeled 50 mL polypropylene tube (that already contains 4 mL TRIzol®). Immediately begin homogenization using the Ultra-Turrax T25 Power Homogenizer. Homogenize on the highest setting (6) for 10-15 seconds. Cool the sample on ice for another 10-15 seconds and then repeat. Continue until the tissue is fully homogenized and the solution is cloudy. Upon complete homogenization, cap the 50 mL tube and return to the ice. Incubate the homogenized tissues at room temperature for 5 minutes before proceeding with the isolation procedure.

Example 8

RNA Preparation Procedures

RNA Isolation: The procedures given in the Invitrogen instructions provided with the TRIzol® reagent are generally followed. Separate the homogenized sample into four 1 mL aliquots in four 1.5 mL microcentrifuge tubes. Add 200 μL of chloroform to each 1 mL aliquot. Cap the tubes, vortex for 15 seconds and then shake up and down. The result should be a pink milky liquid. Incubate the tubes at room temperature for 2-3 minutes. Centrifuge the tubes for 15 minutes at 14,000 rpm and 4° C. Transfer the aqueous phase (top layer) to a sterile 1.5 mL microcentrifuge tube. The typical volume of the aqueous phase which should be transferred to the new tube is about 500 μL. Be sure not to transfer any of the intermediate or lower phases. Precipitate the RNA from solution by adding 500 μL of Isopropyl Alcohol to each microcentrifuge tube containing the aqueous layer. Shake the tubes up and down for at least 20 seconds. Incubate the samples at room temperature for 10 minutes. Centrifuge the samples for 10 minutes, 14,000 rpm at 4° C. Remove the supernatant carefully by aspirating off the liquid being sure not to lose the pellet. Add 1 mL of 70% ethanol to wash the pellet. Dislodge the pellet by flicking the tube (or tapping the tube on the bench top) and shake to mix. Centrifuge for 5 minutes, 8,200 rpm at 4° C. Remove the supernatant carefully by aspirating off the liquid being sure not to lose the pellet. Using a lint free wipe to carefully soak up excess ethanol to make sure the pellet is dry. Resuspend each pellet into 30 μL of RNA Storage Solution. Mix gently by pipetting until the RNA goes back into solution and then store at −80° C. It may be necessary to vortex the sample for a few seconds at a low speed to facilitate the resuspension of the RNA. If this is necessary, spin down the samples, using the microcentrifuge, prior to freezing.

Example 9

RNA Cleaning: Procedures According to the RNeasy® Mini Handbook

RNA Isolation from Cells Cultured in OptiCell Chambers Using the RNeasy Mini Kit. Cells cultured from mammalian cell lines are used to isolate good quality RNA which is then used for future downstream genomic analysis. All work related to the culturing of the cells is to be done under strict aseptic conditions.

Reagents: 10× PBS, deionized H2O, absolute ethanol, RNA Storage Solution, β-Mercaptoethanol, RNase Zap®, Buffer RLT, and Buffer RW1 and Buffer RPE (provided in the RNeasy Mini Kit).

Equipment/Materials: RNeasy Mini Kit, QIAshredder spin columns, OptiCell knife, 20 mL sterile syringe, OptiCell tips, Cell scraper, P1000 Pipetman pipette, Rainin, P200 Pipetman pipette, Rainin, 100-100 μL filtered pipette tips, 1-200 μL filtered pipette tips, sterile transfer pipettes, 55 mL sterile solution basin, 1.5 mL sterile microcentrifuge tubes, and Eppendorf Microcentrifuge.

Solutions: Buffer RLT (stock provided in RNeasy Mini Kit); Add 100 μL of β-Mercaptoethanol per 10 mL of Buffer RLT prior to beginning protocol. 70% Ethanol: Make 50 mL of 70% ethanol by adding 35 mL absolute ethanol to 15 mL deionized, RNase-free water. 1× PBS: RNase-free water. Filter the solution using a 0.22 μm filter.

Procedure: Removing Cells from the OptiCell Chamber (proceed one OptiCell at a time). Check the cells under a microscope to ensure that the cells are alive before isolating RNA. Remove and discard the cell culture medium. Using the OptiCell knife, cut away the top membrane exposing the cells on the lower membrane. Wash the membrane to which the cells are attached three times with 1× PBS. Pipette 600 μL of the Buffer RLT solution (containing β-Mercaptoethanol) onto the center of the membrane to which the cells are attached. Using the cell scraper, gently spread the Buffer RLT over the entire surface of the membrane, and then collect the liquid in one corner. Pipette off the entire volume of Buffer RLT and place into a QIAshredder spin column.

RNA Isolation: Centrifuge the QIAshredder spin columns at 14,000 rpm for 2 minutes. Discard the spin column but keep the collection tube and its contents. Add 600 μL of 70% ethanol to the collection tube and mix well by pipetting (the total volume now=1.2 mL). Transfer 600 μL of the cell lysate to an RNeasy mini column and centrifuge for 15 seconds at 14,000 rpm. Discard the flow through but keep the collection tube and the spin column. Transfer the remaining volume of cell lysate (~600 μL) to the spin column and repeat the centrifugation. Discard the flow through but keep the collection tube and the spin column. Add 700 μL Buffer RW1 to the spin column. Centrifuge for 15 seconds at 14,000 rpm to wash the column. Discard the flow through and the collection tube. Transfer the spin column to a new 2 mL collection tube and add 500 μL Buffer RPE to the column. Centrifuge for 15 seconds at 14,000 rpm. Discard the flow through, keep the collection tube/column. Add another 500 μL Buffer RPE to the column. Centrifuge for 2 minutes at 14,000 rpm. Transfer the spin column to a 1.5 mL collection tube. Add 30 μL of RNA Storage Solution directly to the silica gel membrane and centrifuge for 1 minute at 14,000 rpm to elute the RNA. Store the final RNA at −70° C.

RNA 6000 Nano Assay. Using the Agilent 2100 Bioanalyzer and the RNA 6000 Nano Assay, analyze RNA isolated from cultured mammalian cells, lymphocytes or tissues for quality.

Reagents: RNA 6000 Nano gel matrix, RNA 6000 Nano dye concentrate, RNA 6000 Nano Marker, (all of the above reagents are contained in the RNA 6000 Nano Assay kit, Agilent), RNA 6000 ladder, RNase Zap, and RNase-free water, from Ambion.

Equipment/Other Materials: Agilent Chip Priming Station, Agilent, RNA 6000 chip, Agilent, electrode cleaners, P2, P10, P200, and P1000 Rainin Pipetman pipettes, sterile, DNase/RNase free filtered pipette tips, 1.5 mL microcentrifuge tubes, sterile, vortex, IKA vortex mixer, microcentrifuge, and heating block.

Procedure: The procedure is given in the Reagent Kit Guide, RNA 6000 Nano Assay, Edition November 2003, by Agilent Technologies. The procedures are followed as given in the Guide, with the following modifications: Preparing the Gel, pg. 17—rather than separating the filtered gel into aliquots of 65 μL each, keep the stock filtered gel in the original microcentrifuge tube and aliquot the 65 μL as needed. Loading the RNA 6000 Nano Marker, pg. 22—add 1 uL of RNase-free water (instead of RNA 6000 Nano Marker) to each sample well that will not contain sample. Not only will this conserve the amount of Marker used but also serves as a negative control to see that none of the reagents are contaminated, including the RNase-free water. Loading the Ladder and Samples, pg. 23—heat denature the samples and RNA 6000 Ladder for an additional 30 seconds (total of 2.5 minutes) at 71° C. Starting the Chip Run, pg. 26—choose the "Eukaryote Total RNA Nano" option from the assay menu.

Example 10

Affymetrix GeneChip Expression Analysis

Gene expression is analyzed using a proprietary Affymetrix Feline GeneChip®. Total RNA is reverse transcribed into cDNA. The cDNA is used to generate cRNA which is fragmented and used as probes for GeneChip hybridization. The gene chip is washed and the hybridization signal is measured with an Affymetrix laser scanner. The hybridization data are then validated and normalized for further analysis in accordance with instructions from the manufacturer.

Equipment: Eppendorf microcentrifuge, 1.5 mL DNase and RNase free/sterile microcentrifuge tubes, 50 mL DNase and RNase free/sterile disposable polypropylene tubes, P1000, P200, P20, P10 and P2 Rainin Pipetman pipettes, Filter pipette tips for P1000, P200, P20, P10 and P2 pipettes, DNase and RNase free/sterile, and Peltier Thermal Cycler PTC-200.

Procedure: follow all procedures exactly as described in GeneChip Expression Analysis Technical Manual (Affymetrix Copyright 1999-2003). Use 5 microgram of total RNA for the first strand cDNA synthesis. Use either Peltier Thermal Cycler PTC-200 or heat block for temperature control on reactions and probe denaturing. The quality control is performed using RNA NanoDrop chips with BioAnalyer 2100. Use 100 Format (Midi Array) for the feline genechip.

Example 11

Gene Expression in Hyperthyroid Felines

Studies are conducted in accordance with the previous Examples using felines afflicted with mild and severe hyperthyroidism to determine the underlying gene expression differences between these animals and normal felines. Procedures as described in the Examples of this specification are used to prepare tissue and bodily fluid samples from a statistically relevant number of felines that are healthy, that are afflicted with mild hyperthyroidism, and that are afflicted with severe hyperthyroidism. These studies involve measurement of gene expression data comparing the normal felines with the afflicted felines with respect to expression of one or more of, inter alia, sodium/iodide transporter (NIS), thyroid peroxidase (TPO), thyroid stimulating hormone receptor (TSHR), iodide transporter (IT; Pendrin), thyroid oxidase (ThOX), $T_4$ thyroxine deiodinase (e.g., intrathyroidal type I 5'-deiodinase), monocarboxylate transporter (e.g., monocarboxylate transporter-8), and a thyroid hormone receptor activator molecule, i.e., including but not limited to the genes identified in FIG. 1. In a particular embodiment, these studies involve measurement of gene expression data comparing the normal felines with the afflicted felines with respect to expression of the feline NIS gene.

Example 12

Cell Culture Methods for Identification of Bioactive Dietary Components

Bioactive dietary components are food components that can alter expression of one or more genes in a manner that leads to reduction in the levels of thyroid hormone or other biological effects that reduce the effects of hyperthyroidism. These bioactive dietary components can be identified, for example, by contacting appropriate cells in tissue culture with, e.g., extracts of food components and measuring the level of expression of one or more genes involved in, inter alia, the production, transport, or utilization of thyroid hormones, including, but not limited to sodium/iodide transporter (NIS), thyroid peroxidase (TPO), thyroid stimulating hormone receptor (TSHR), iodide transporter (IT; Pendrin), thyroid oxidase (ThOX), $T_4$ thyroxine deiodinase (e.g., intrathyroidal type I 5'-deiodinase), monocarboxylate transporter (e.g., monocarboxylate transporter-8), and a thyroid hormone receptor activator molecule, i.e., including but not limited to the genes identified in FIG. 1. In the present disclosure, expression of the feline NIS gene is measured and three bioactive dietary components are identified using the gene expression methodology set forth above.

Seeding New Cell Lines

REAGENTS: Complete Media (specific to each individual cell line); 70% ethanol, prepared in house; 70% propanol, prepared in house. One (1) stock aliquot of canine or feline cells, ATCC (or an aliquot of frozen cells from a previous pass)

MATERIALS/EQUIPMENT: Laminar flow hood; Serological Pipettes, sterile, VWR Automatic pipet-aid; OptiCell units, BioCrystal 1004-01; OptiCell tips, BioCrystal 1011-01; OptiCell rack, BioCrystal 1006-01; Solution basins, sterile, VWR; 50 mL sterile conical tubes, VWR 21008-736; Water bath at 37° C.; Permanent marker.

PROCEDURE: Prepare the appropriate type of medium for the cell line to be seeded. Warm the media in a 37° C. water bath for 25-30 minutes. Sterilize the laminar flow hood and all reagents/equipment that will be used during the procedure with 70% propanol. Label OptiCell units with the cell line, cell type, date, and pass number. Remove the vial containing the cells from the liquid nitrogen tank and thaw rapidly (approximately 2 minute thaw time) in a 37° C. water bath. Place the vial containing the cells in a beaker containing a small amount of 70% ethanol in order to cleanse the outside and remove any bacteria and/or other contaminants. Remove the vial from the 70% ethanol and allow to air dry under the laminar flow hood. Mix the thawed aliquot of cells with the appropriate amount of complete medium to fill the OptiCell units to the maximum capacity of 10 mL each. Example: If the volume of cells is 1.5 mL (and the cells will be seeded into two OptiCell units) add the cells to 18.5 mL of complete medium in a sterile 50 mL tube. Mix thoroughly, but carefully, and inject 10 mL of the cell/medium mixture into each of the two OptiCell units. Remove the excess air from each of the OptiCell units. Wipe off the external ports of the OptiCell units with 70% propanol and place into the OptiCell rack. Place the OptiCell rack into the incubator under the correct temperature and CO2 conditions.

Cell Culture Using OptiCell Chambers

MATERIALS: OptiCell units, BioCrystal 1004-01; OptiCell rack, BioCrystal 1006-01; OptiCell tips, sterile, BioCrystal 1011-01; 10 cc/20 cc sterile syringes, VWR 53548-006/53548-008; Serological pipettes, sterile, VWR; Waste Container; Solution basins, sterile, VWR 21007-972; 50 mL sterile conical tubes; 2 mL sterile cryogenic vials, VWR 66021-944; tube racks, both for 50 mL and 2 mL tubes; Complete Medium; Trypsin-EDTA, Gibco 25200-056; 1× PBS, Gibco 20012-027; 70% alcohol, prepared in-house; Water bath, 37° C.; Beckman Coulter Allegra 25R Centrifuge, SN AJC01J015; Accujet automated pipet-aid; Vi-Cell XR Cell Viability Analyzer, Beckman Coulter, SN AH391.

PROCEDURE: Changing Medium: Attach a new OptiCell tip to a sterile syringe and fill with 10 mL of air. Inject the air into the OptiCell chamber and, without removing the tip, invert the chamber and remove the medium. Discard the medium in an appropriate waste container. Using a new OptiCell tip, fill a new syringe with 10 mL of complete medium and inject into the OptiCell chamber. Without removing the tip, invert the chamber and remove any air. Store the OptiCell chambers in an OptiCell rack in a 37° C. incubator under the appropriate $CO_2$ conditions.

Harvesting/Seeding

Attach a new OptiCell tip to a syringe and fill with 10 mL of air. Inject the air into the OptiCell chamber. Without removing the tip, invert the OptiCell chamber and remove the medium. Discard the medium. Using a new OptiCell tip and new syringe, inject 10 mL of sterile 1× PBS (at room temperature) into the OptiCell chamber. Without removing the tip, invert the chamber several times to wash the cells and then remove the PBS. Discard the PBS. Using a new OptiCell tip and new syringe, inject 4 mL of Trypsin-EDTA into the OptiCell chamber. Remove the tip and invert the chamber several times to coat the cells. Place the OptiCell chamber back into the storage rack. Incubate the OptiCell chambers at 37° C. for 2-2.5 minutes. Verify that all cells have detached using a microscope. It may be necessary to gently shake the chamber(s) to help with the detachment of the cells. Using a new OptiCell tip and syringe, inject 10 mL of complete medium into the OptiCell chamber. Without removing the tip, invert the chamber several times to neutralize the effects of the Trypsin-EDTA, and then remove the cell suspension. Place the suspension into a sterile 50 mL conical tube. After all cells have been removed from all of the OptiCell chambers, make sure that the volume in each of the 50 mL tubes is equal and then centrifuge at 800×g for 5 minutes at room temperature. Carefully remove the supernatant and resuspend the cell pellet in complete medium. Using the cell counter, determine the total number of cells harvested and the # viable cells/mL. Seed the appropriate number of cells into new OptiCell chambers. Note that the amount of medium used to resuspend the cells in steps above is variable and will dependent upon the assay to be performed.

Harvesting, Freezing, and Subculturing of Canine and Feline Cells

MATERIALS: Complete Media (specific for each cell line); 70% alcohol, prepared in-house; Trypsin-EDTA, Gibco 25200-056; Dimethylsulfoxide, Fisher; Cultured canine and/or feline cell lines, ATCC; Laminar flow hood; Serological Pipettes, sterile (50 mL, 25 mL, 10 mL, 5 mL and 2 mL), VWR; Automatic pipet-aid; 50 mL sterile conical tubes, VWR 21008-736; 2 mL sterile cryogenic vials, VWR 66021-944; 150 $cm^2$ sterile culture flasks, VWR 15705-074; Water bath, 37° C.; Beckman Coulter Allegra 25R Centrifuge, SN AJC01J015; 50 mL tube rack; cryo-vial tube rack; and Permanent marker.

PROCEDURE: Cell Harvesting. Warm the appropriate complete medium and trypsin-EDTA in a 37° C. water bath for 25-30 minutes before continuing with the protocol. Remove the complete medium from each of the flasks containing the cells to be harvested and put into a waste container. Add 7 mL of trypsin-EDTA to each of the flasks. Make sure that the trypsin-EDTA covers the bottom of the flask (the surface where the cells are attached) and place into a 37° C. incubator for 2.5 minutes. Remove the flasks from the incubator and examine under the microscope to determine the progress of detachment. "Spank" each flask and reexamine under the microscope. Continue "spanking" until all of the cells have been detached from the bottom of the flask. Remove the trypsin-EDTA/cell suspension from each flask and place into 50 mL conical tube(s). Fill the 50 mL tube(s) to volume with complete medium to neutralize the effects of the trypsin-EDTA. Centrifuge each of the 50 mL tubes at 800×g for 5 minutes at room temperature. Remove the supernatant and resuspend the cellular pellet in 48 mL of complete medium. Only resuspend those cells that will be used for subculturing in complete medium. For those cells that will be frozen and stored for later use, follow the "Freezing" procedure.

Freezing: Prepare a 5% dimethylsulfoxide (DMSO) in complete medium solution (most cell lines require a 5% solution but it is important to check the individual requirements for each cell line). Resuspend the cell pellets to be frozen (from step 1.10) in 2 mL of the 5% DMSO in media solution. Separate the DMSO/cell mixture into 1.5 mL aliquots in 2 mL cryogenic vials. Place these aliquots into the Styrofoam® cooler in the −70° C. freezer overnight. Remove the aliquots from the −70° C. freezer the next morning and transfer into liquid nitrogen.

Subculturing: Determine the appropriate subculture ratio for the cell line and label the correct number of flasks. (This protocol is designed for a 1:8 subculture ratio and all volumes reflect that ratio). Add 14 mL of complete medium to each of the aforementioned flasks while in the vertical position. Add 6 mL of the cellular suspension (step 1.10) to each of the flasks while still in the vertical position. Do not "drop" the cellular suspension into the flask—instead allow the suspension to trickle down the side of the flask. Make sure that the media/cell mixture completely covers the bottom of the flask. Do not get medium into the neck of the flask. Place the flasks into a 37° C. incubator under the appropriate conditions. Proper Labeling for Cell Culture Flasks will include the following information: Cell Line, Cell Type, Date, Pass number, Media and $CO_2$ requirements. Proper Labeling for Cryogenic Vials: will include the following identifying information: Cell Line, Cell Type, Date, Pass number, and Worker's initials.

Solubilization and Extraction of Ingredients for Testing in Cell Cultures

The methods below are illustrative approaches for solubilizing ingredients at specific concentrations for testing in cell culture. In general, ingredients are received either as dry chemicals, liquids, or grains. The active component of each ingredient is extracted using a specified solvent. The solvents used in the process may include, e.g., Millipore $H_2O$, buffered Millipore $H_2O$, DMSO, 0.1% DMSO (in Millipore $H_2O$), methanol, and ethanol. Dry chemicals are added directly to the specified solvent and visually inspected to insure they have completely dissolved at the desired stock concentration. Liquids of known concentration are added directly to the specified solvent to obtain the final desired stock concentration. Grains are ground, using a coffee grinder, sonicated (level: 008 Watts), and filtered (0.45 μm) at the desired stock concentration.

MATERIALS/EQUIPMENT: Vortex; AT200 Mettler Balance; AR15 Accumet pH Meter; VirSonic 100 Sonicator; Coffee grinder (Krups); 20 mL Sterile Syringe (Norm-Ject); VWR 53548-008; Syringe tips, 18 G, 1½" needle, sterile, VWR BD305196; Acrodisc 25 mm Syringe Filter (w/0.45 μm HT Tuffryn Membrane), VWR 28144-007; 50 mL centrifuge tube (Corning), Fisher 06-443-19; P10, P20, P100, P200, P1000 Rainin pipettes; Filter pipet tips, sterile, USA Scientific.

SOLUTIONS: Millipore $H_2O$, Milli-Q Synthesis A10; DMSO, EMD MX1458-6; 0.1% DMSO (in Millipore $H_2O$); 1M HEPES buffer solution, Gibco 15630-080; Buffered Millipore $H_2O$ (pH:7); Methanol (99.93% HPLC grade), Sigma-Aldrich 439193; Ethanol (200 Proof), Sigma-Aldrich E7023; NOTE: pure $H_2O$ should be buffered to a pH of 7, using the 1M HEPES buffer solution.

PROCEDURE:

Solubility Testing: Dry Chemical. Place a 50 mL centrifuge tube on the Mettler balance. Tare the balance, once you have obtained a weight. To the centrifuge tube weighed in the first step, add small amount of the dry chemical to be tested and place the tube w/cap back on the balance. Write down the weight of dry chemical added. Add the specified solvent to obtain your desired stock concentration (mg/mL). Vortex and visually inspect for complete dissolution.

Solubility Testing: Liquid Ingredient. Add the desired amount of liquid ingredient to 50 mL Centrifuge tube, using the necessary. Rainin pipet. Add the solvent to bring to desired stock concentration ($C_1V_1=C_2V_2$). Vortex to mix thoroughly and check that the solution is uniform.

Solubility Testing: Grains. Thoroughly grind any amount of the grain to be tested in the coffee grinder. Check for the presence of any large pieces and regrind, if necessary. Place a 50 mL centrifuge tube w/cap on the Mettler balance. Tare the balance, once you have obtained a weight. To the centrifuge tube weighed in the second step, add the desired amount of ground up ingredient and place the tube w/cap back on the balance. Record the weight of ingredient. Add the specified solvent to obtain your desired stock concentration (mg/mL). Sonicate for 30-60 s at a reading: 008 Watts. Filter sonicated solution using 20 mL syringe and 0.45 μm filter into a new 50 mL centrifuge tube. If the sonicated solution does not filter through the 0.45 μm, use the ultracentrifuge to pellet out smaller pieces of ingredient and decant the supernatant.

Results

Three food ingredients that comprise bioactive dietary components are identified using the methods described above. They include tomato pomace, vegetable blend and millet. The probes used in the analysis, which are carried by the gene chips employed, include a set of 25-mer oligonucleotides derived from the nucleotide sequence of SEQ ID NO: 1. Changes in expression levels of the feline NIS gene upon exposure of cells in tissue culture to extracts of each are presented in the following table:

TABLE 1

| Ingredient | % Change In NIS Gene Expression |
| --- | --- |
| Tomato Pomace -1 (II) | −1% |
| Tomato Pomace -2 (LB) | +15% |
| Tomato Pomace -3 (WE) | −37% |
| Tomato Pomace E1 | −30% |
| Vegetable Blend (M2707) | −10% |
| Vegetable Blend (M2707) (8Ctl_Vs_16Trt) | −22% |
| Vegetable Blend (M2707) EtOH | −119% |
| Vegetable Blend (M2707) (8Ctl_Vs_16Trt) | −49% |
| Millet (M0019) | −45% |

The data of Table 2 demonstrate that the methods disclosed herein can be used to identify bioactive dietary components that can reduce expression of the feline gene and therefore would be useful for treating feline hyperthyroidism. These data also illuminate the variability in composition of particular food ingredients and extracts thereof. Notwithstanding that variability, the extraction and assays methods disclosed herein can be used, e.g., to "assay" a given ingredient lot for the amount and concentration of bioactive dietary component. With that data, feline pet food compositions can be formulated to include an amount of food ingredient to provide an effective amount of the bioactive dietary component. Although the pet food compositions disclosed herein describe varying levels of the bioactive dietary components, the actual amount included preferably would be the amounts recited are for illustrative purposes; the actual amount would be the therapeutically-effective amount determined according to the methods disclosed herein.

In other aspects, the methods and reagents disclosed above could be used more extensive extraction, fractionation, isolation, and purification of the food ingredients to allow the definition of the molecular species responsible for the observed activity. Those identified compound(s) could then be more precisely incorporated into a pet food composition or a dietary supplement to be used for treatment of feline hyperthyroidism.

In still further aspects, a therapeutically-effective amount of the food ingredients comprising the bioactive dietary components, or the isolated and purified agents, per se, are formulated into pet food compositions comprising low levels of iodide formulations, to provide an improved food with additional protection against extraneous iodine consumption by the animal under treatment for hyperthyroidism.

In another aspect, a therapeutically-effective amount of the food ingredients comprising the bioactive dietary components, or the isolated and purified agents, per se, are formulated into pet food compositions designed to treat a disease or condition other than hyperthyroidism to provide a diet useful for the treatment of hyperthyroidism as well as a second identified disease or condition.

In a still further aspect, the disclosure provides a pet food composition or food supplement comprising at least additive, and in certain embodiments, synergistic amounts of more than one bioactive dietary component, or more than one isolated and purified agent, per se, to provide a pet food composition or pet food supplement useful for reducing thyroid hormone production and/or for treatment of hyperthyroidism.

Illustrative examples of such feline pet food compositions provided below; though amounts of the bioactive dietary components specified, those levels can and should be adjusted to achieve required, or "standardized" units or biological activity levels, using the above methods and procedures to measure the level of the biologically active materials.

It is contemplated that the invention described herein is not limited to the particular methodology, protocols, and reagents described as these may vary. It is also to be understood that the terminology used herein is for the purpose of describing particular embodiments only, and is not intended to limit the scope of the present invention in any way.

In the specification there have been disclosed typical, illustrative, and preferred embodiments of the invention and, although, specific terms are employed, they are used in a generic and descriptive sense only and not for purposes of limitation, the scope of the invention being set forth in the claims. Many modifications and variations of the invention are possible in light of the above teachings. It is therefore to be understood that within the scope of the appended claims the invention may be practiced otherwise than as specifically described.

What is claimed is:

1. An isolated cDNA molecule comprising (a) a nucleotide sequence that encodes a protein having the amino acid sequence of SEQ ID NO:2, or (b) a nucleotide sequence that is completely complementary to the nucleotide sequence of (a).

2. An isolated cDNA molecule comprising at least 70 contiguous nucleotides of SEQ ID NO:1 or at least 70 contiguous nucleotides completely complementary to the nucleotide sequence of SEQ ID NO:1.

3. The isolated cDNA molecule of claim 2, wherein the 70 contiguous nucleotides are within a coding sequence of the feline sodium/iodide symporter protein (NIS protein).

4. A recombinant DNA vector comprising an insert, wherein the insert comprises the cDNA molecule of claim 1.

5. A transformed cell comprising the recombinant DNA vector of claim 4.

6. The recombinant DNA vector of claim 4, further comprising a nucleic acid sequence encoding a reporter polypeptide.

7. The recombinant DNA vector of claim 6, further comprising a thyroid response element, wherein the thyroid response element is in operative association with the reporter polypeptide.

8. The cDNA molecule of claim 1, further comprising a labeling moiety.

9. The cDNA molecule of claim 2, further comprising a labeling moiety.

10. The cDNA molecule of claim 3, further comprising a labeling moiety.

11. The cDNA molecule of claim 8, wherein the labeling moiety is a fluorophore or streptavidin.

12. The cDNA molecule of claim 9, wherein the labeling moiety is a fluorophore or streptavidin.

13. The cDNA molecule of claim 10, wherein the labeling moiety is a fluorophore or streptavidin.

* * * * *

SEQUENCE LISTING

```
<160> NUMBER OF SEQ ID NOS: 2

<210> SEQ ID NO 1
<211> LENGTH: 946
<212> TYPE: DNA
<213> ORGANISM: Felis catus

<400> SEQUENCE: 1
ccctcactgt gtagatgaga aaactgaagc ccagagaagg gcagaggctt gccagggcac      60
ccagtgggtc attactgagc ccgagattgg gacccatcag tgtctccctt ccccctccct     120
gtgcttggtc tccagttctc tttgccctgt cactaaatgc ccccatttcc ctcaggcccc     180
accaagcgca gtgccttggg tcctgggctg ctgtggtggg accttgcacg acagacagca     240
tcggtggccc ccaaggaaga agtggctacc ttggatgaca gcttggggaa gggtgctgag     300
gagctgcccc ctggagccaa gaggcctcct gacttcttgc ccagtgatga ggaccgtccg     360
ctcttcctgg ggcagaagga ggtggaggga gccggctccc agaccccag cagtggacat      420 gaccatggcc aggaccttcg ggagacccac ctctgagcca gcaggcgact gaccactgaa     480
ccccgcaggt tcctgggatg gaacctcagg gtgggccact cccaggccac aggagcatag     540
ccttgggctc cgattggctg gactgtgtcc tatgcaaatg agtttgggac tgaatgtccc     600
gccctacgga aagaggtgaa gccctgcctt taggaggtca ttttatccag ccccttctt      660 ccagccagtc cctagtctta ggtgctgcac ccttgcccgc tcccccaaaa tgaagccaga     720 ttttctcca cgttcaatgg aaagatgttg gagtcccctc tggacaacac gggaaaactc      780
caggcccaag atgagggtct gagaaagtct ccggggctcc tctggaacat gtctgaacct     840
```

```
tagcaaggat tttcaaggtc ctcaggcaca accccctgca ccccatttca cagatggggg    900
aaagtgaggt ctggaaaggg acaacaactt tgaccaaggt cacaga                   946
```

<210> SEQ ID NO 2
<211> LENGTH: 94
<212> TYPE: PRT
<213> ORGANISM: Felis catus

<400> SEQUENCE: 2

```
Ser Gly Pro Thr Lys Arg Ser Ala Leu Gly Pro Gly Leu Leu Trp Trp
1               5                   10                  15

Asp Leu Ala Arg Gln Thr Ala Ser Val Ala Pro Lys Glu Glu Val Ala
            20                  25                  30

Thr Leu Asp Asp Ser Leu Gly Lys Gly Ala Glu Glu Leu Pro Pro Gly
        35                  40                  45

Ala Lys Arg Pro Pro Asp Phe Leu Pro Ser Asp Glu Asp Arg Pro Leu
    50                  55                  60

Phe Leu Gly Gln Lys Glu Val Glu Gly Ala Gly Ser Gln Thr Pro Ser
65                  70                  75                  80

Ser Gly His Asp His Gly Gln Asp Leu Arg Glu Thr His Leu
                85                  90
```